(12) United States Patent
Goodall et al.

(10) Patent No.: US 10,772,507 B2
(45) Date of Patent: *Sep. 15, 2020

(54) SYSTEMS, DEVICES AND METHODS FOR MONITORING BREASTFEEDING

(71) Applicant: Elwha LLC, Bellevue, WA (US)

(72) Inventors: Eleanor V. Goodall, Seattle, WA (US); Roderick A. Hyde, Redmond, WA (US); Wayne R. Kindsvogel, Seattle, WA (US); Elizabeth A. Sweeney, Seattle, WA (US); Charles Whitmer, North Bend, WA (US)

(73) Assignee: Elwha LLC, Bellevue, WA (US)

( * ) Notice: Subject to any disclaimer, the term of this patent is extended or adjusted under 35 U.S.C. 154(b) by 552 days.

This patent is subject to a terminal disclaimer.

(21) Appl. No.: 15/422,040

(22) Filed: Feb. 1, 2017

(65) Prior Publication Data

US 2018/0214026 A1    Aug. 2, 2018

(51) Int. Cl.
*A61B 5/00* (2006.01)
*A61B 5/107* (2006.01)

(52) U.S. Cl.
CPC .......... *A61B 5/0091* (2013.01); *A61B 5/1073* (2013.01); *A61B 5/1079* (2013.01);
(Continued)

(58) Field of Classification Search
CPC ... A61B 5/0091; A61B 5/1073; A61B 5/1079; A61B 5/4312; A61B 5/6804;
(Continued)

(56) References Cited

U.S. PATENT DOCUMENTS

| 4,384,288 A | 5/1983 | Walton |
| 7,630,591 B2 | 12/2009 | Allen et al. |

(Continued)

OTHER PUBLICATIONS

Chawla et al.; "An Overview of Passive RFID"; IEEE Applications & Practice; Sep. 2007; pp. 11-17; IEEE.
(Continued)

*Primary Examiner* — Lindsey G Wehrheim
(74) *Attorney, Agent, or Firm* — Daniel J. Honz; Advent, LLP

(57) ABSTRACT

Breast monitoring systems are described including a breast sensor device having a substrate fabricated to substantially conform to one or more breasts of a subject, dynamically bendable optical fibers, and a connector; a light source configured to operably couple with the optical fibers through the connector; a photodetector configured to operably couple with the optical fibers through the connector and positioned to detect light transmission through the optical fibers; a reporting device; and a microcontroller including a microprocessor and circuitry, the circuitry including input circuitry configured to receive a first set of signals and at least one second set of signals from the photodetector; calculation circuitry configured to calculate a curvature delta value based on a comparison of the first and at least one second set of signals, and calculate a breast volume delta value from the calculated curvature delta value; and reporting circuitry.

44 Claims, 18 Drawing Sheets

(52) U.S. Cl.
CPC .......... *A61B 5/4312* (2013.01); *A61B 5/6804* (2013.01); *A61B 5/6823* (2013.01); *A61B 2562/0266* (2013.01); *A61B 2562/046* (2013.01); *A61B 2562/164* (2013.01)

(58) Field of Classification Search
CPC .......... A61B 5/6823; A61B 2562/0266; A61B 2562/046; A61B 2562/164
See application file for complete search history.

(56) References Cited

U.S. PATENT DOCUMENTS

| | | | |
|---|---|---|---|
| 7,833,177 | B2 | 11/2010 | Long et al. |
| 8,280,493 | B2 | 10/2012 | Kolberg et al. |
| 8,521,272 | B2 | 8/2013 | Kapon et al. |
| 8,801,658 | B2 | 8/2014 | Harari et al. |
| 9,057,603 | B2 | 6/2015 | Oyamada |
| 2003/0044155 | A1 | 3/2003 | Maiden |
| 2010/0217148 | A1 | 8/2010 | Binder |
| 2012/0277636 | A1 | 11/2012 | Blondheim et al. |
| 2013/0109963 | A1 | 5/2013 | Zhu |
| 2018/0214066 | A1* | 8/2018 | Goodall ............ A41D 1/002 |

OTHER PUBLICATIONS

Chen et al.; "Optical bend sensor for vector curvature measurement based on Bragg grating in eccentric core polymer optical fibre"; 20th International Conference on Optical Fibre Sensors; bearing a date of Oct. 23, 2013; pp. 1-4; vol. 7503.

El-Oteify et al; "Assessment of the breast volume by a new simple formula"; Indian Journal of Plastic Surgery; bearing a date of Aug. 8, 2016; pp. 13-16; vol. 39, Issue 1.

Finkenzeller, Klaus; "Fundamental Operating Principles"; RFID Handbook: Fundamentals and Applications in Contactless Smart Cards and Identification; uploaded on Jan. 31, 2017; pp. 29-59; John Wiley & Sons, Ltd.

Fujiwara et al.; "Flexible Optical Fiber Bending Transducer for Application in Glove-Based Sensors"; IEEE Sensors Journal; Oct. 2014; pp. 3631-3636; vol. 14—No. 10; IEEE.

Ghosh et al.; "Development of a sensor-embedded flexible textile structure for apparel or large area applications"; Indian Journal of Fibre & Textile Research; Mar. 2005; pp. 42-48; vol. 30.

Krebber Katerina; "Smart Technical Textiles Based on Fiber Optic Sensors"; Current Developments in Optical fiber Technology; uploaded Jan. 31, 2017; pp. 319-344.

Roberts, Andy; "Curvature Attributes and their Application to 3D Interpreted Horizons"; Enterprise Oil Norge Ltd.; uploaded Jan. 31, 2017; pp. 1-14.

Roberts et al.; "Ultimate low loss of hollow-core photonic crystal fibres"; Optics Express; Jan. 10, 2005; pp. 236-244; vol. 13, No. 1; Optical Society of America.

T100/FBG Sensing Array; Technica Fiber Technology to Sense the World; uploaded Nov. 8, 2016; 1 page; Technica Optical Components.

To et al.; "Highly Stretchable Optical Sensors for Pressure, Strain, and Curvature Measurement"; 2015 IEEE/RSJ International Conference on Intelligent Robots and Systems (IROS); Sep. 28-Oct. 2, 2015; pp. 5898-5903; vol. 15; IEEE.

Vallan et al.; "Design and Characterization of Curvature Sensors Based on Plastic Optical Fibers for Structural Monitoring"; uploaded Jan. 31, 2017; 5 pages.

Vallan et al.; "Static Characterization of Curvature Sensors Based on Plastic Optical Fibers"; IEEE Transactions on Instrumentation and Measurement; Jan. 24, 2014; pp. 1-8; IEEE.

* cited by examiner

Fig. 2

| 100 Wearable Breast Monitor |
|---|

| 110 Flexible Substrate |
|---|
| 200 Flexible Strip    202 Flexible Sleeve    204 Flexible Garment |

| 120 One or more Optical Fibers |
|---|
| 206 Plastic Optical Fibers    208 Polymer Optical Fibers |
| 210 Acrylic Optical Fibers    212 Glass Optical Fibers |
| 214 Photonic Crystal Fibers |

| 130 At least one Light Source | 140 At least one Photodetector |
|---|---|
| 216 Light Emitting Diode | 220 Photodiode |
| 218 Laser Diode | |

| 150 Reporting Device |
|---|
| 222 Haptic Reporting Device    224 Audio Reporting Device    226 Optical Reporting Device    228 Transmission Unit |

| 160 Microcontroller |
|---|
| 170 Microprocessor |
| 180 Circuitry |
| 182 Input Circuitry    184 Calculation Circuitry    186 Reporting Circuitry |

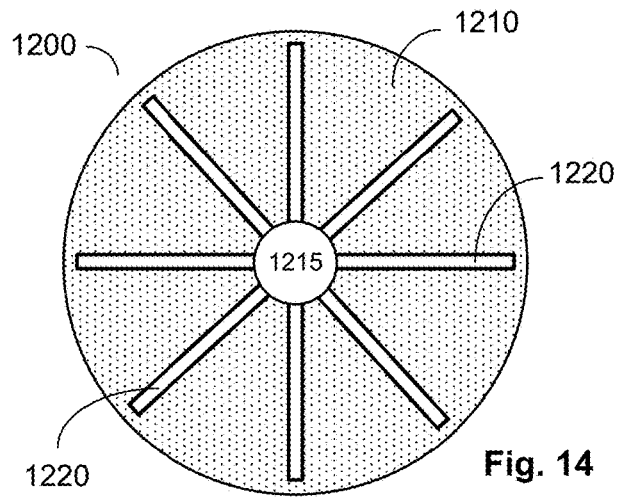
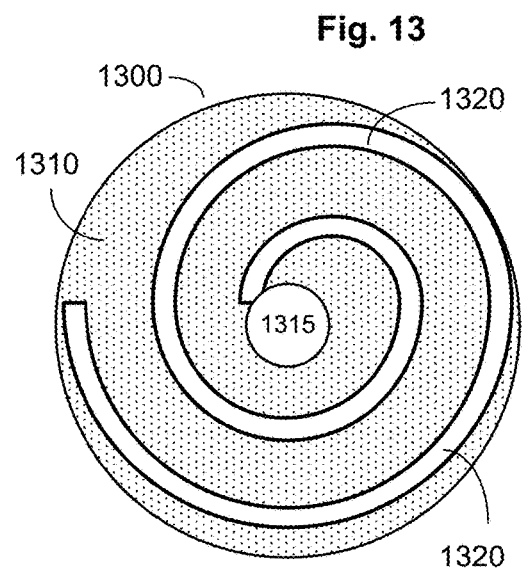
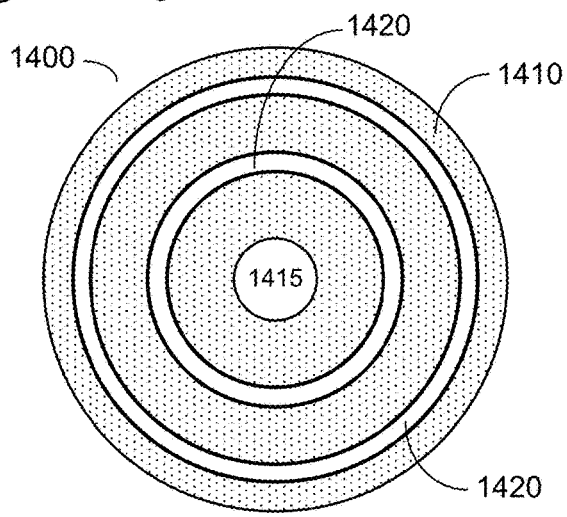
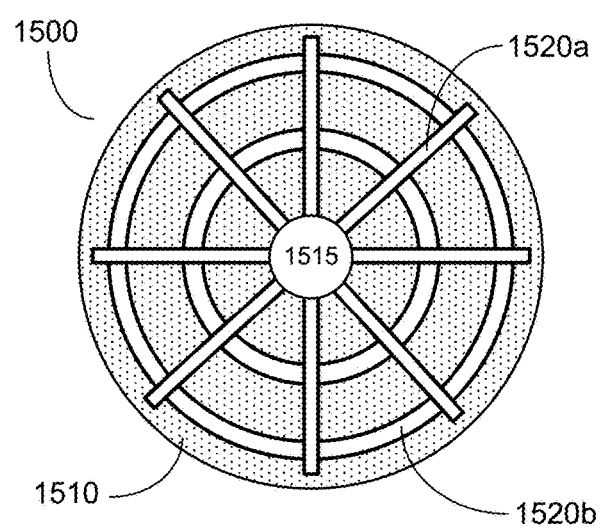
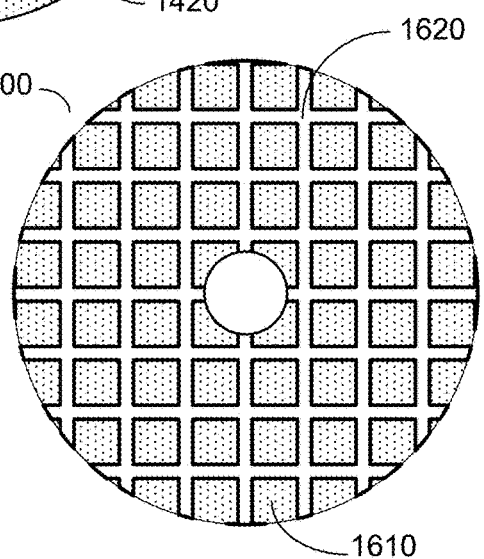

s = arc-length along the surface
$\mathcal{R}(s)$ = inverse curvature (radius of curvature)
θ = local slope angle

2210
Receiving a first set of signals at a first time point from at least one photodetector positioned to detect light reception from one or more optical fibers associated with a flexible substrate of a wearable breast monitor

2220
Receiving at least one second set of signals at at least one second time point from the at least one photodetector positioned to detect light reception from the one or more optical fibers associated with the flexible substrate of the wearable breast monitor

2230
Calculating a curvature delta value based on comparing the received first set of signals and the received at least one second set of signals

2240
Calculating a breast volume delta value from the calculated curvature delta value

2250
Transmitting one or more signals having information regarding the calculated breast volume delta value to a reporting device

2310
Measuring curvature of a breast during a breastfeeding event at a first time point and at at least one second time point with one or more optical fibers associated with a flexible substrate of a wearable breast monitor

2320
Calculating a change in curvature of the breast during the breastfeeding event between the first time point and the at least one second time point

2330
Correlating the calculated change in curvature of the breast during the breastfeeding event with a volume of milk expressed between the first time point and the at least one second time point

2340
Reporting the volume of milk expressed during the breastfeeding event between the first time point and the at least one second time point to a user

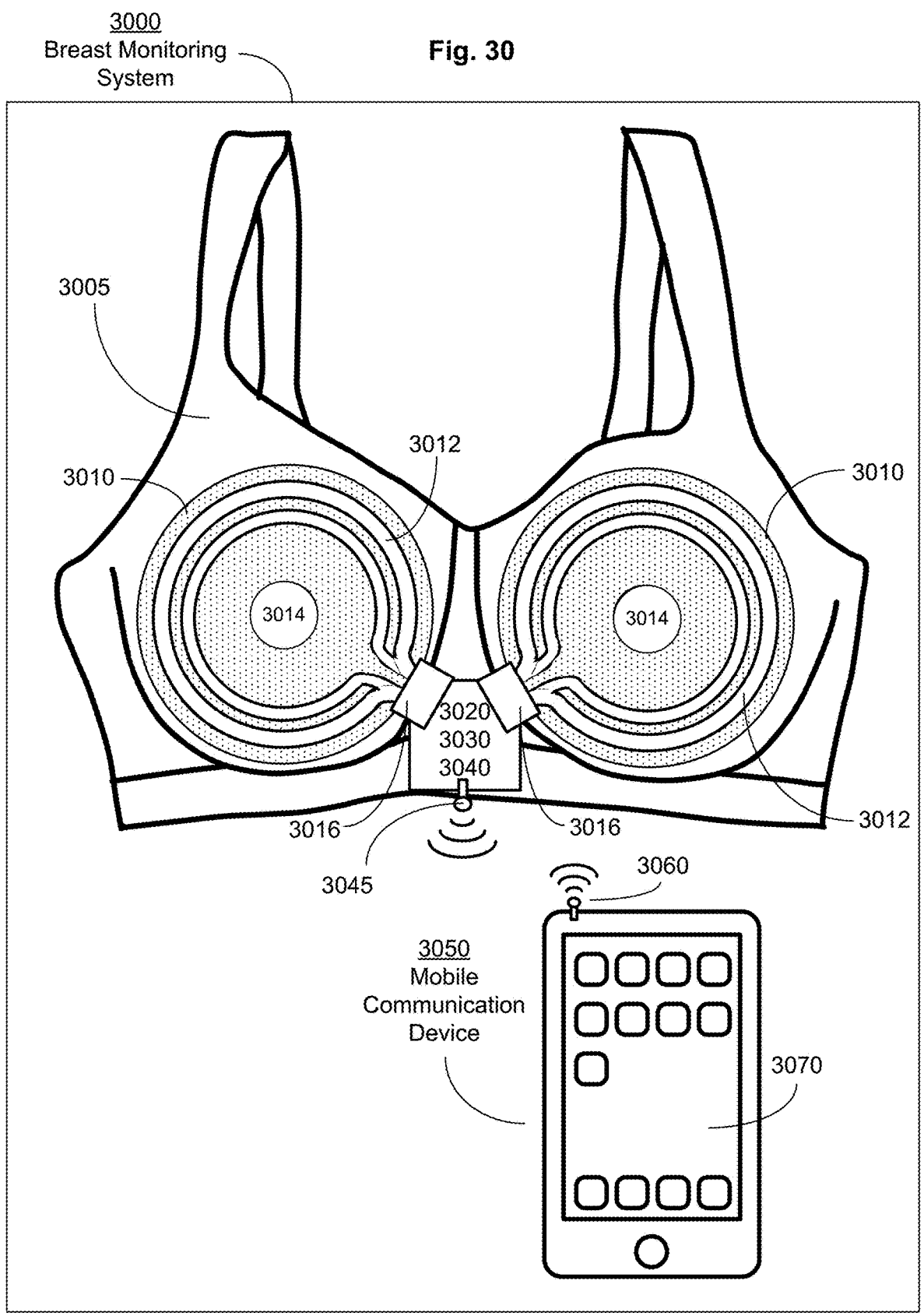

SYSTEMS, DEVICES AND METHODS FOR MONITORING BREASTFEEDING

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an embodiment, a wearable breast monitor includes, but is not limited to, a flexible substrate fabricated to substantially conform to external contours of at least a portion of one or more breasts of a subject; one or more optical fibers associated with the flexible substrate, wherein the one or more optical fibers are dynamically bendable; at least one light source operably coupled to the one or more optical fibers; at least one photodetector positioned to detect light reception from the one or more optical fibers; a reporting device; and a microcontroller including a microprocessor and circuitry, wherein the circuitry includes input circuitry configured to receive a first set of signals from the at least one photodetector, and receive at least one second set of signals from the at least one photodetector; calculation circuitry configured to calculate a curvature delta value based on a comparison of the received first set of signals and the received at least one second set of signals from the at least one photodetector, and calculate a breast volume delta value from the calculated curvature delta value; and reporting circuitry configured to transmit a signal to the reporting device based on the calculated breast volume delta value. In addition to the foregoing, other aspects of a wearable breast monitor are described in the claims, drawings, and text forming a part of the present disclosure.

In an embodiment, a breast monitoring system includes, but is not limited to, a flexible substrate fabricated to substantially conform to external contours of at least a portion of one or more breasts of a subject; one or more optical fibers associated with the flexible substrate, wherein the one or more optical fibers are dynamically bendable; at least one light source operably coupled to the one or more optical fibers; at least one photodetector positioned to detect light reception from the one or more optical fibers; a reporting device; and a microcontroller including a microprocessor and circuitry, wherein the circuitry includes input circuitry configured to receive a first set of signals from the at least one photodetector, and receive at least one second set of signals from the at least one photodetector; calculation circuitry configured to calculate a curvature delta value based on a comparison of the received first set of signals and the received at least one second set of signals from the at least one photodetector, and calculate a breast volume delta value from the calculated curvature delta value; and reporting circuitry configured to transmit a signal to the reporting device based on the calculated breast volume delta value. In addition to the foregoing, other system aspects are described in the claims, drawings, and text forming a part of the present disclosure.

In an embodiment, a breast monitoring system includes, but is not limited to, a wearable breast monitor including a flexible substrate fabricated to substantially conform to external contours of at least a portion of one or more breasts of a subject, one or more optical fibers associated with the flexible substrate, wherein the one or more optical fibers are dynamically bendable, at least one light source operably coupled to the one or more optical fibers; at least one photodetector positioned to detect light reception from the one or more optical fibers; and a transmission unit including an antenna and operably coupled to the at least one photodetector, the transmission unit configured to transmit signals, the transmitted signals including light reception information from the at least one photodetector; and a computing device including a receiver and a microprocessor with circuitry, the circuitry including input circuitry configured to receive a first set of transmitted signals from the transmission unit of the wearable breast monitor, and receive at least one second set of transmitted signals from the transmission unit of the wearable breast monitor; calculation circuitry configured to calculate a curvature delta value based on a comparison of the received first set of transmitted signals and the received at least one second set of transmitted signals from the transmission unit of the wearable breast monitor, and to calculate a breast volume delta value from the calculated curvature delta value; and reporting circuitry configured to report the calculated breast volume delta value. In addition to the foregoing, other system aspects are described in the claims, drawings, and text forming a part of the present disclosure.

In an embodiment, a method for monitoring breastfeeding includes, but is not limited to, measuring a curvature of a breast during a breastfeeding event at a first time point and at at least one second time point with one or more optical fibers associated with a flexible substrate of a wearable breast monitor; calculating a change in curvature of the breast during the breastfeeding event between the first time point and the at least one second time point; correlating the calculated change in curvature of the breast during the breastfeeding event with a volume of milk expressed between the first time point and the at least one second time point; and reporting the volume of milk expressed during the breastfeeding event between the first time point and the at least one second time point to a user. In addition to the foregoing, other method aspects are described in the claims, drawings, and text forming a part of the present disclosure.

In an embodiment, a method for monitoring breastfeeding includes, but is not limited to, receiving a first set of signals at a first time point from at least one photodetector positioned to detect light reception from one or more optical fibers associated with a flexible substrate of a wearable breast monitor; receiving at least one second set of signals at at least one second time point from the at least one photodetector positioned to detect light reception from the one or more optical fibers associated with the flexible substrate of the wearable breast monitor; calculating a curvature delta value based on comparing the received first set of signals and the received at least one second set of signals; calculating a breast volume delta from the calculated curvature delta value; and transmitting one or more signals having information regarding the calculated breast volume delta to a reporting device. In addition to the foregoing, other method aspects are described in the claims, drawings, and text forming a part of the present disclosure.

In an embodiment, a breast monitoring system includes, but is not limited to, a breast sensor device including a flexible substrate fabricated to substantially conform to external contours of at least a portion of one or more breasts of a subject; one or more optical fibers associated with the flexible substrate, wherein the one or more optical fibers are dynamically bendable; and at least one connector operably coupled to the one or more optical fibers; at least one light source configured to operably couple with a first end of the one or more optical fibers of the breast sensor device through the at least one connector; at least one photodetector configured to operably couple with a second end of the one or more optical fibers of the breast sensor device through the at least one connector, the at least one photodetector positioned to detect light transmission through at least one of the one or more optical fibers from the at least one light source; a reporting device; and a microcontroller including a microprocessor and circuitry, wherein the circuitry includes input circuitry configured to receive a first set of signals from the at least one photodetector, and receive at least one second set of signals from the at least one photodetector; calculation circuitry configured to calculate a curvature delta value based on a comparison of the received first set of signals and the received at least one second set of signals from the at least one photodetector, and calculate a breast volume delta value from the calculated curvature delta value; and reporting circuitry configured to transmit a signal to the reporting device based on the calculated breast volume delta value. In addition to the foregoing, other system aspects are described in the claims, drawings, and text forming a part of the present disclosure.

In an embodiment, a breast sensor device includes, but is not limited to, a flexible substrate fabricated to substantially conform to external contours of at least a portion of one or more breasts of a subject; one or more optical fibers associated with the flexible substrate, wherein the one or more optical fibers are dynamically bendable; and at least one connector operably coupled to the one or more optical fibers. In addition to the foregoing, other device aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2 is a block diagram showing aspects of a wearable breast monitor such as depicted in FIG. 1.

FIG. 12 shows an embodiment of an optical fiber pattern on a flexible substrate of a wearable breast monitor.

FIG. 13 shows an embodiment of an optical fiber pattern on a flexible substrate of a wearable breast monitor.

FIG. 14 shows an embodiment of an optical fiber pattern on a flexible substrate of a wearable breast monitor.

FIG. 15 shows an embodiment of an optical fiber pattern on a flexible substrate of a wearable breast monitor.

FIG. 16 shows an embodiment of an optical fiber pattern on a flexible substrate of a wearable breast monitor.

FIG. 22 shows a block diagram of a method for monitoring breastfeeding.

FIG. 23 shows a block diagram of a method for monitoring breastfeeding.

FIG. 30 illustrates an embodiment of a breast monitoring system including a breast sensor device.

DETAILED DESCRIPTION

Figure 1:
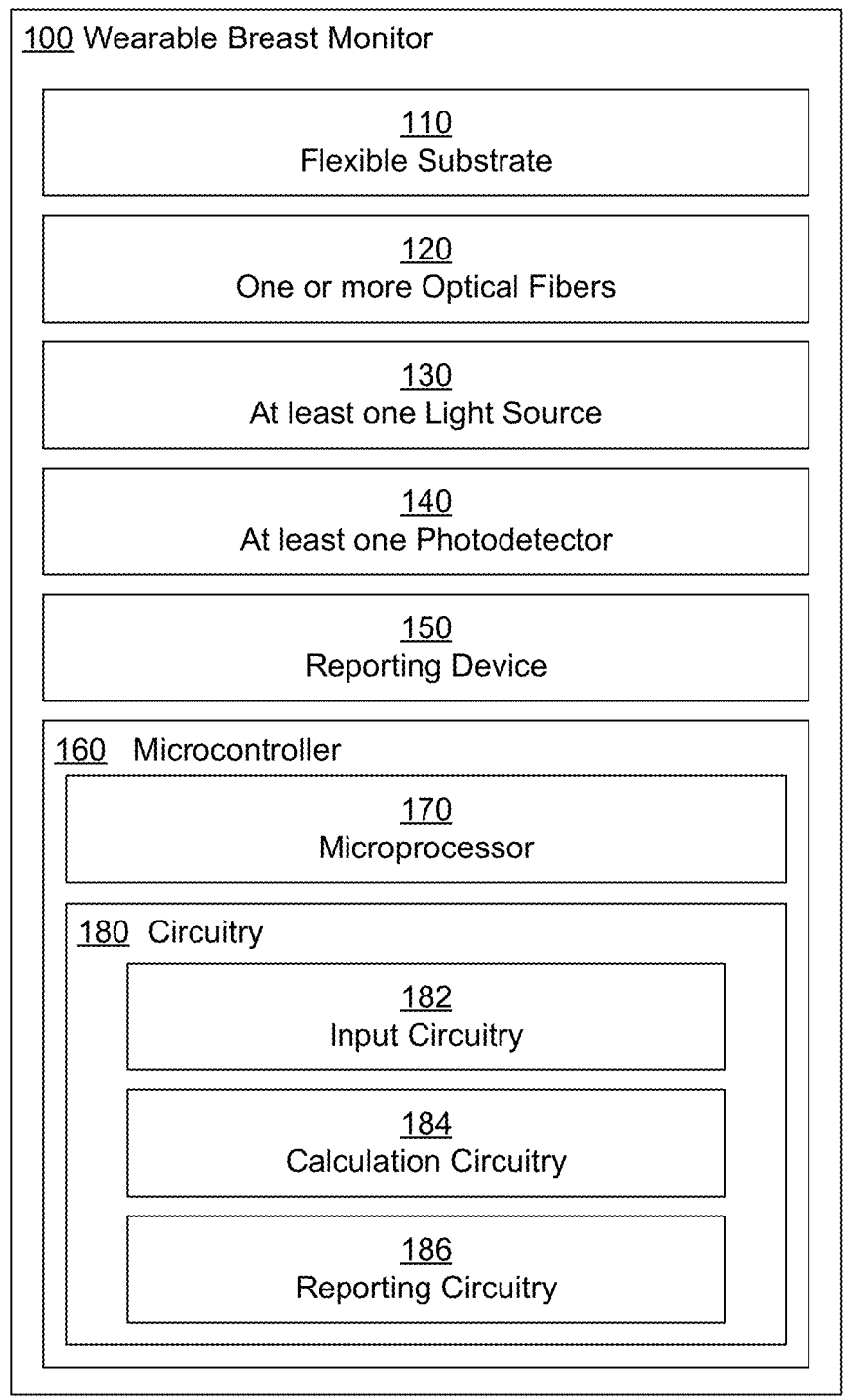
FIG. 1 is a block diagram of a wearable breast monitor.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Described herein are systems, devices, and methods for monitoring breastfeeding. In an aspect, the systems, devices, and methods for monitoring breastfeeding include a device intended for application to a mammalian breast and including one or more optical fibers for use in measuring changes in the curvature of the breast before, during, and/or after a breastfeeding event. The changes in curvature can be correlated with changes in breast volume to calculate a volume of milk expressed from the breast during the breastfeeding event.

An optical fiber can act as a waveguide or "light guide," guiding light introduced at one end of the guide through to the other end. The amount of light transmitted through the optical fiber is altered when the optical fiber is bent. For example, light rays entering the optical fiber within a cone defined by the numerical aperture correspond to rays that are incident at the core/cladding interface of a straight fiber at an angle larger than the critical angle and thus reflected, whereas rays having a smaller incident angle are refracted and escape from the fiber core. Fiber bending can cause a change in the incidence angle at the core-cladding interface, so even rays that are within the acceptance cone can be incident at the core/cladding interface with an angle smaller than the critical angle, and thus radiated with a reduction in the received power at the fiber end.

FIG. 1 shows a block diagram illustrating non-limiting aspects of a wearable breast monitor for calculating changes in breast volume during a breastfeeding event using optical fibers. Wearable breast monitor 100 includes flexible substrate 110. Flexible substrate 110 is fabricated to substantially conform to external contours of at least a portion of one or more breasts of a subject. For example, the flexible substrate can include a flexible strip, flexible sheet, or garment fabricated to substantially conform to the external contours, i.e., the skin surface, of at least a portion of one or more breasts of a nursing mother. Wearable breast monitor 100 further includes one or more optical fibers 120 associated with the flexible substrate 110. For example, the one or more optical fibers can be attached to, incorporated into, or woven into the flexible substrate of the wearable breast monitor. The one or more optical fibers 120 are dynamically bendable. For example, the one or more optical fibers are fabricated with materials that allow for dynamic bending and straightening as the volume and associated curvature of the breast changes during a breastfeeding event. Wearable breast monitor 100 further includes at least one light source 130 operably coupled to the one or more optical fibers 120. For example, a light emitting diode can be positioned to transmit light into one end of the one or more optical fibers. Wearable breast monitor 100 further includes at least one photodetector 140 positioned to detect light reception from the one or more optical fibers 120. In some embodiments, the at least one photodetector 140 is positioned at an end of the one or more optical fibers 120. In some embodiments, the at least one photodetector 140 is position along a length of the one or more optical fibers 120. In some embodiments, the at least one photodetector 140 is positioned to detect light transmitted through the one or more optical fibers 120. In some embodiments, the at least one photodetector 140 is positioned to detect light reflected from the one or more optical fibers 120. In some embodiments, the at least one photodetector 140 is positioned to detect light refracted from the one or more optical fibers 120. Wearable breast monitor 100 further includes reporting device 150. In some embodiments, reporting device 150 is configured to directly report information to a user, i.e., the subject wearing or using the wearable breast monitor. For example, an audio, haptic, or optical reporting device can be used to report information to a nursing mother before, during, or after a breastfeeding event. In an aspect, the user is an individual (e.g., a healthcare provider or lactation consultant) monitoring a nursing mother and/or a nursing infant during a breastfeeding event. In some embodiments, reporting device 150 is configured to report information to an external device. For example, the reporting device can include a transmission unit and antenna for transmitting information to an external device, e.g., a smart phone. Wearable breast monitor 100 further includes microcontroller 160 including microprocessor 170 and circuitry 180. Circuitry 180 includes input circuitry 182 configured to receive a first set of signals from the at least one photodetector 140, and receive at least one second set of signals from the at least photodetector 140. Circuitry 180 includes calculation circuitry 184 configured to calculate a curvature delta value based on a comparison of the received first set of signals and the received second set of signals from the at least one photodetector 140, and calculate a breast volume delta value from the calculated curvature delta value. Changes in breast volume during a breastfeeding event can be correlated with a volume or an amount of milk expressed during the breastfeeding event. Circuitry 180 further includes reporting circuitry 186 configured to transmit a signal to the reporting device 150 based on the calculated breast volume delta value.

FIG. 2 illustrates further aspects of a wearable breast monitor. Wearable breast monitor 100 includes a flexible substrate 110. The flexible substrate is fabricated to substantially conform to the external contours (e.g., the skin surface) of at least a portion of one or more breasts of a subject. In an aspect, the flexible substrate of the wearable breast monitor including the one or more optical fibers is sized to cover at least a portion of the superolateral, superomedial, inferolateral, and/or inferomedial quadrants of the breast. In an aspect, the flexible substrate of the wearable breast monitor is sized to cover at least a portion of the upper outer, upper inner, lower outer, and/or lower inner portions of the breast. In an aspect, the flexible substrate of the wearable breast monitor is sized to cover the entirety of the breast.

The flexible substrate of the wearable breast monitor can take any of a number of forms sized to substantially conform to external contours of at least a portion of one or more breasts of a subject. For example, the flexible substrate can take the form of one or more strips or patches having a rectangular, square, trapezoid, polygon, triangular, circular, or oval shape configured for placement on a skin surface of one or more breasts of a nursing mother. For example, the flexible substrate can take the form of a sleeve that fits over at least a portion of the breast. For example, the flexible substrate can take the form of a garment.

In some embodiments, flexible substrate 110 of wearable breast monitor 100 covers only a portion of the breast. In an embodiment, flexible substrate 110 is a flexible strip 200 fabricated to substantially conform to the external contours of at least a portion of at least one of the one or more breasts of the subject. For example, the flexible substrate of the wearable breast monitor can include a flexible strip formed from a flexible material and configured for placement on the skin surface of a breast of a nursing mother. The flexible strip can take the form of a rectangular, square, trapezoid, polygon, triangular, circular, or oval shape configured for placement on or adherence to a skin surface of a breast. For example, the flexible substrate of the wearable breast monitor can include a flexible strip sized for placement on at least a portion of the superolateral, superomedial, inferolateral, and/or inferomedial quadrants of the breast. The flexible substrate can include a series of interconnected flexible strips sized for placement on the skin surface of the breast. The flexible substrate can include a long strip of flexible material sized to span from a medial edge to a lateral edge of the breast or from an upper edge to a lower edge of the breast. In some embodiments, the flexible substrate can include a long strip of flexible material sized to encircle a portion of the breast. In some embodiments, the flexible strip 200 is adhered to the surface of the breast with, e.g., a biocompatible, pressure sensitive adhesive. In some embodiments, flexible strip 200 is sized for placement between the external contours of the at least a portion of at least one of the one or more breasts of the subject and a brassiere. In some embodiments, the flexible strip 200 is attached to an inner surface of the brassiere. For example, a wearable breast monitor can include a flexible substrate that is a flexible strip sized to be worn on the inside surface of a nursing bra.

In some embodiments, flexible substrate 110 of wearable breast monitor 100 is a flexible sleeve 202 fabricated to substantially conform to the external contours of at least a portion of at least one of the one or more breasts of the subject. For example, the flexible substrate can include a flexible material, e.g., a stretchable fabric, knit, or mesh, sized to fit over a breast. In some embodiments, the flexible sleeve 202 is adhered to the surface of the breast. For example, the flexible sleeve can include a biocompatible, pressure sensitive adhesive to adhere the flexible sleeve to the surface of the breast. In some embodiments, flexible sleeve 202 is sized for placement between the external contours of the at least a portion of at least one of the one or more breasts of the subject and a brassiere. In some embodiments, the flexible sleeve 202 is attached to an inner surface of the brassiere. For example, the flexible sleeve forming the flexible substrate of a wearable breast monitor can be sized to be worn on the inside surface of a brassiere or nursing bra.

In some embodiments, flexible substrate 110 is a flexible garment 204 fabricated to substantially conform to the external contours of at least a portion of the one or more breasts of the subject. In an aspect, flexible garment 204 is a brassiere. For example, the flexible garment can include a standard bra, sports bra, or other form-fitting undergarment. In an aspect, flexible garment 204 is a nursing bra. For example, the flexible substrate can be a nursing bra into which the optical fibers, photodetectors, reporting device, and microcontroller have been incorporated to form the wearable breast monitor. In some embodiments, the flexible garment is fabricated in a range of sizes to accommodate a variety of cup and chest sizes. In some embodiments, the flexible garment is fabricated in a limited number of sizes and is configured to stretch to accommodate a variety of cup and chest sizes. Other non-limiting examples of flexible garments include form-fitting shirts, bustiers, camisoles, tube tops, and the like.

The flexible substrate of the wearable breast monitor is at least one of bendable, stretchable, elastic, fitted, or form-fitting. In some embodiments, the flexible substrate is fabricated from a thin sheet of dynamically bendable material. For example, the flexible substrate can include a thin sheet of paper or other cellulose-based material. For example, the flexible substrate can include a metallic foil (e.g., stainless steel, molybdenum, or aluminum foils). For example, the flexible substrate can include a thin sheet of flexible plastic or polymer film formed from, for example, poly(ethylene terephthalate) (PET), poly(ethylene naphthalate) (PEN), or polyimide (PI).

In some embodiments, the flexible substrate is fabricated from a fabric. Non-limiting examples of fabric include natural fabrics, e.g., cotton or wool, and synthetic fabrics, e.g., nylon, rayon, or polyester. For example, a flexible strip, sleeve, or garment can be formed from one or more natural and/or synthetic fabrics. In some embodiments, the fabric is a woven fabric, e.g., a loom woven or knit fabric. In some embodiments, the fabric is a nonwoven fabric, e.g., fabric-like material formed from long fibers bonded together by chemical, mechanical, heat, or solvent treatment. Non-limiting examples include rayon, poly(ethylene terephthalate) (PET), and polypropylene.

In some embodiments, the flexible substrate is fabricated from a stretchable or elastomeric fabric. In some embodiments, the flexible substrate includes a stretchable fabric with 2-way stretch. In some embodiment, the flexible substrate includes a stretchable fabric with 4-way stretch. In some embodiments, the flexible substrate includes a material with stretch memory, e.g., a cotton, polyester, nylon blend. Non-limiting examples of stretchable fabric includes a knit fabric (e.g., cotton knit or cotton knit blend), synthetic polymer, spandex, elastane, lycra, nylon, polyester, polyurethane, or olefin fiber.

In some embodiments, the flexible substrate is fabricated from a form-fitting material that substantially conforms to the external contours of the at least one portion of the one or more breasts of the subject. For example, the flexible substrate can be formed from a form-fitting material that is a stretchable or elastomeric fabric, e.g., a knit fabric, synthetic polymer, spandex, elastane, lycra, nylon, polyester, polyurethane, or olefin fiber. For example, the flexible substrate can be formed from a form-fitting that conforms to the external contours of a breast, e.g., a "shrink-wrap" type material. In an aspect, only a portion of the flexible substrate includes a form-fitting material. For example, flexible garment, e.g., a brassiere, may include form-fitting material only in the cups of the brassiere.

In an aspect, at least a portion of the flexible substrate includes a soft fabric. In an aspect, at least one surface of the flexible substrate includes a soft fabric. For example, a portion of the flexible substrate intended to come in contact with a nursing infant (e.g., the nursing infant's cheek) can include a soft fabric or material compatible with the infant's skin. For example, the soft fabric can include a fleece, flannel, faux fur, soft cotton, satin, silk, and the like.

Figure 3:
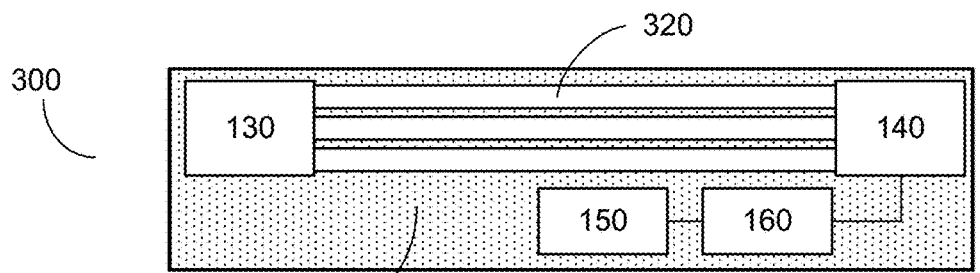
FIG. 3 shows an embodiment of a wearable breast monitor.

FIGS. 3, 4, 5A, 5B, 6A, and 6B show non-limiting examples of a wearable breast monitor having a flexible substrate that is a flexible strip. FIG. 3 shows a non-limiting example of a wearable breast monitor 300 including flexible strip 310. Wearable breast monitor 300 includes one or more optical fibers 320 associated with flexible strip 310. Optical fibers 320 are dynamically bendable. In this non-limiting example, the one or more optical fibers 320 are shown positioned parallel to one another. Wearable breast monitor 300 further includes at least one light source 130 operably coupled to the one or more optical fibers 320 and at least one photodetector 140 positioned to detect light reception from the one or more optical fibers 320. In this non-limiting example, the at least light source 130 is operably coupled at a first end of the one or more optical fibers and the at least one photodetector 140 is positioned to detect light reception at a second end of the one or more optical fibers 320. In some embodiments, the at least one photodetector 140 can be positioned somewhere along the length of the one or more optical fibers 320. Wearable breast monitor 300 further includes reporting device 150 and microcontroller 160 including a microprocessor and circuitry, wherein the circuitry includes input circuitry configured to receive a first set of signals from the at least one photodetector 140, and receive at least one second set of signals from the at least one photodetector 140; calculation circuitry configured to calculate a curvature delta value based on a comparison of the received first set of signals and the received at least one second set of signals from the at least one photodetector 140, and calculate a breast volume delta value from the calculated curvature delta value; and reporting circuitry configured to transmit a signal to the reporting device 150 based on the calculated breast volume delta value.

Figure 4:
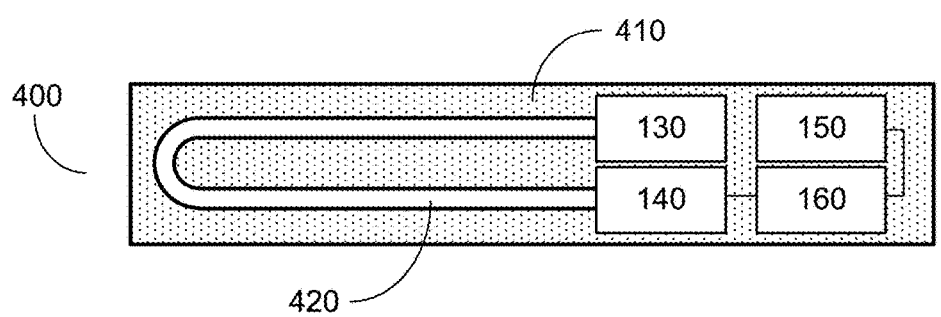
FIG. 4 shows an embodiment of a wearable breast monitor.

FIG. 4 shows an embodiment of a wearable breast monitor 400 including flexible substrate 410. Wearable breast monitor 400 includes one or more optical fibers 420 associated with flexible strip 410. Optical fibers 420 are dynamically bendable. In this non-limiting example, the one or more optical fibers are shown forming a U-shape. Wearable breast monitor 400 further includes at least one light source 130 operably coupled to the one or more optical fibers 420 and at least one photodetector 140 positioned to detect light reception from the one or more optical fibers 420. In this non-limiting example, the at least light source 130 is operably coupled at a first end of the one or more optical fibers 420 forming the U-shape and the at least one photodetector 140 is positioned to detect light transmission at a second end of the one or more optical fibers 420 forming the U-shape. In some embodiments, the at least one photodetector 140 can be positioned somewhere along the length of the one or more optical fibers 420. Wearable breast monitor 400 further includes reporting device 150 and microcontroller 160 including a microprocessor and circuitry, wherein the circuitry includes input circuitry, calculation circuitry, and reporting circuitry configured to receive and process information from the at least one photodetector 140 to calculate a breast volume delta value and to transmit information to reporting device 150 based on the breast volume delta value.

Figure 5A:
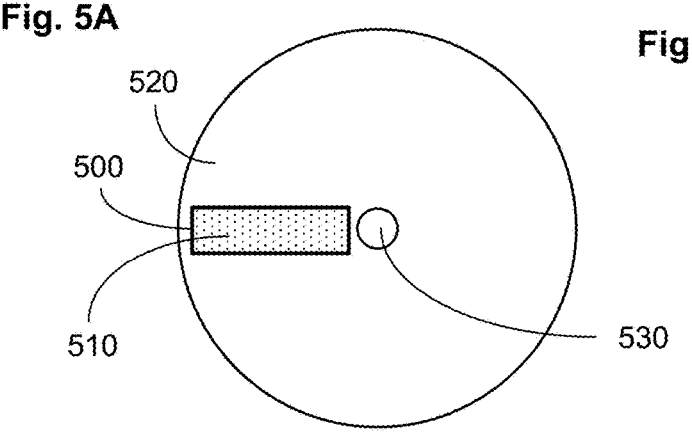
FIG. 5A is a frontal view of an embodiment of a wearable breast monitor on a breast.
Figure 5B:
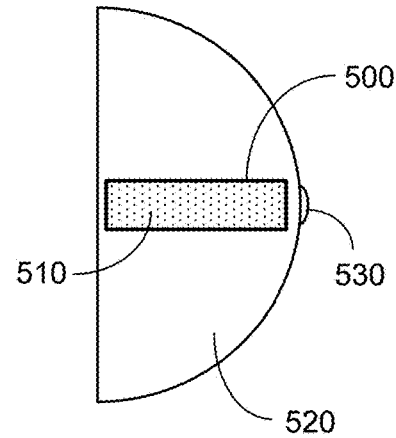
FIG. 5B is a side view of an embodiment of a wearable breast monitor on a breast.

FIGS. 5A and 5B show a non-limiting embodiment of a wearable breast monitor that includes a flexible substrate that is a single flexible strip. FIG. 5A shows a frontal view of wearable breast monitor 500 including flexible substrate 510 associated with a frontal view of a breast 520 including nipple 530. Wearable breast monitor 500 further includes one or more optical fibers, at least one light source, at least one photodetector, a reporting device and a microcontroller including a microprocessor and circuitry. In this non-limiting example, wearable breast monitor 500 has a flexible substrate 510 positioned on breast 520 with one end in proximity to nipple 530 and a second end of positioned towards the lateral side of breast 520. In some embodiments, wearable breast monitor 500 includes an adhesive on at least one surface configured to firmly adhere the device to the skin surface of breast 520. FIG. 5B shows a side view of breast 520 with nipple 530. Also shown is wearable breast monitor 500 including flexible substrate 510 positioned on the surface of breast 520.

Figure 6A:
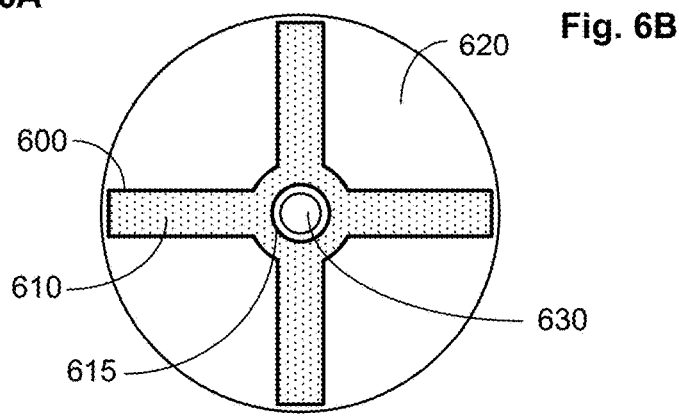
FIG. 6A is a frontal view of an embodiment of a wearable breast monitor on a breast.
Figure 6B:
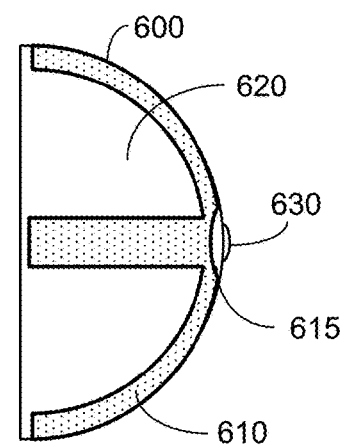
FIG. 6B is a side view of an embodiment of a wearable breast monitor on a breast.

FIGS. 6A and 6B show a non-limiting embodiment of a wearable breast monitor that includes a flexible substrate that includes a radial pattern of flexible strips. FIG. 6A shows wearable breast monitor 600 including flexible substrate 610 associated with a frontal view of a breast 620 including nipple 630. In this non-limiting example, wearable breast monitor 600 includes a cross-pattern of flexible strips that includes nipple access portion 615 defined by the flexible substrate 610 and includes an aperture sized to accommodate nipple 630 of breast 620. The flexible substrate 610 of wearable breast monitor 600 radiates out from the nipple in several directions to allow measurement of changes in breast curvature during a breastfeeding event. Wearable breast monitor 600 further includes one or more optical fibers, at least one light source, at least one photodetector, a reporting device and a microcontroller including a microprocessor and circuitry. In some embodiments, wearable breast monitor 600 includes an adhesive on at least one surface configured to firmly adhere the device to the skin surface of breast 620. FIG. 6B shows a side view of breast 620 with nipple 630. Also shown is wearable breast monitor 600 with flexible substrate 610 and nipple access portion 615 positioned on the surface of breast 620.

Figure 7A:
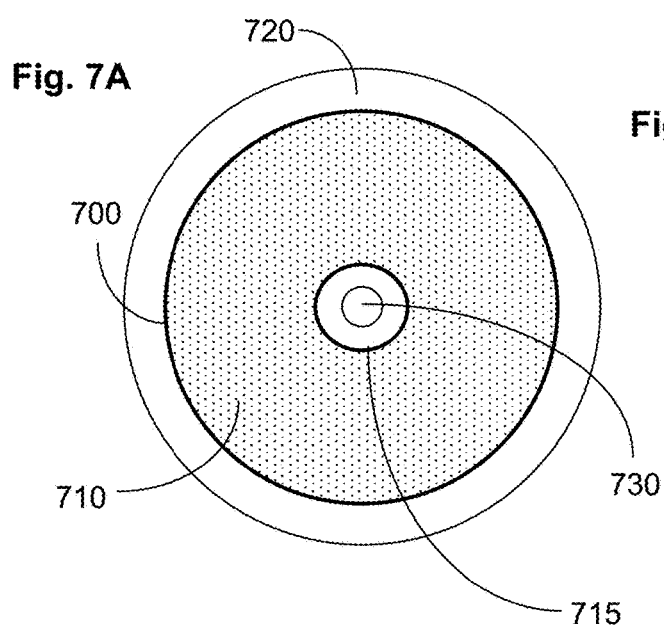
FIG. 7A is a frontal view of an embodiment of a wearable breast monitor on a breast.
Figure 7B:
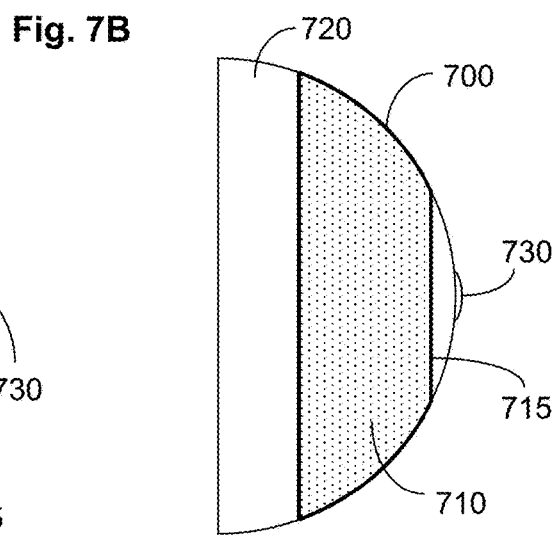
FIG. 7B is a side view of an embodiment of a wearable breast monitor on a breast.

In some embodiments, flexible substrate 110 is a flexible sleeve fabricated to substantially conform to the external contours of at least a portion of at least one of the one or more breasts of the subject. For example, the flexible substrate can include a sleeve fabricated from flexible form-fitting material, e.g., a stretchable fabric, sized to fit over a breast, e.g., slipped onto or over the breast region of the subject. FIGS. 7A, 7B, 8, and 9 show non-limiting embodiments of a wearable breast monitor. FIGS. 7A and 7B show a non-limiting example of a wearable breast monitor including a flexible substrate that is a flexible sleeve. FIG. 7A shows a frontal view of wearable breast monitor 700 including flexible substrate 710 associated with breast 720 including nipple 730. Wearable breast monitor 700 further includes nipple access portion 715 defined by flexible substrate 710 and including an aperture to accommodate nipple 730. Wearable breast monitor 700 further includes one or more optical fibers, at least one light source, at least one photodetector, a reporting device and a microcontroller including a microprocessor and circuitry. In this non-limiting example, wearable breast monitor 700 includes a flexible substrate 710 that is a flexible sleeve that fits snuggly around breast 720 and allows for access to nipple 730 through nipple access portion 715. FIG. 7B shows a side view of breast 720 including nipple 730 and wearable breast monitor 700 attached to the breast surface and including flexible substrate 710 and nipple access portion 715. In some embodiments, the flexible substrate 710 of wearable breast monitor 700 is adhered to the surface of breast 720. In some embodiments, the flexible substrate 710 of wearable breast monitor 700 is sized for placement between the external contours of the breast 720 and a brassiere. For example, the flexible sleeve can be sized to be worn on the inside surface of a nursing bra. In some embodiments, the flexible substrate 710 of wearable breast monitor 700 is attached to an inner surface of the brassiere.

Figure 8:
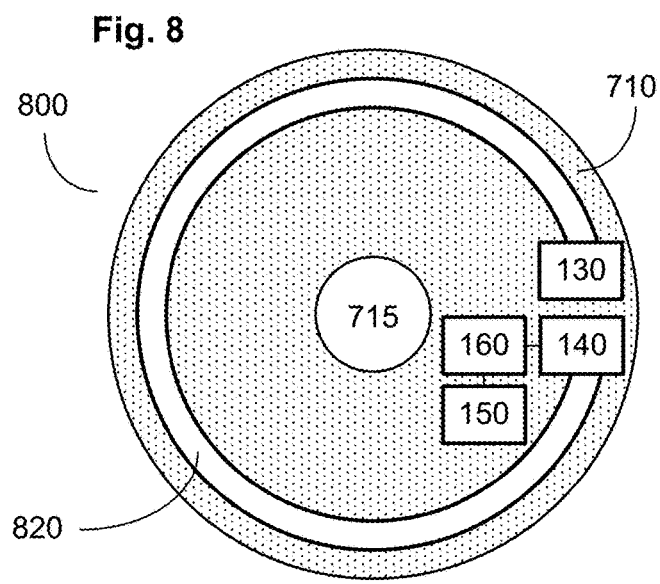
FIG. 8 shows an embodiment of a wearable breast monitor.

FIG. 8 shows an embodiment of a wearable breast monitor. In this non-limiting example, wearable breast monitor 800 includes flexible substrate 710 and nipple access portion 715. Wearable breast monitor 800 further includes one or more optical fibers 820 associated with flexible substrate 710, wherein the one or more optical fibers are dynamically bendable. In this non-limiting example, the one or more optical fibers 820 form a ring associated with the flexible substrate 710 with a first end operably coupled to at least one light source 130 and a second end in proximity to at least one photodetector 140 positioned to detect light reception from the one or more optical fibers 820. Wearable breast monitor 800 further includes reporting device 150 and microcontroller 160 including a microprocessor and circuitry, the circuitry including input circuitry configured to receive a first set of signals from the at least one photodetector 140, and receive at least one second set of signals from the at least one photodetector 140; calculation circuitry configured to calculate a curvature delta value based on the comparison of the received first set of signals and the received at least one second set of signals, and calculate a breast volume delta value from the calculated curvature delta value; and reporting circuitry configured to transmit a signal to the reporting device 150 based on the calculated breast volume delta value.

Figure 9:
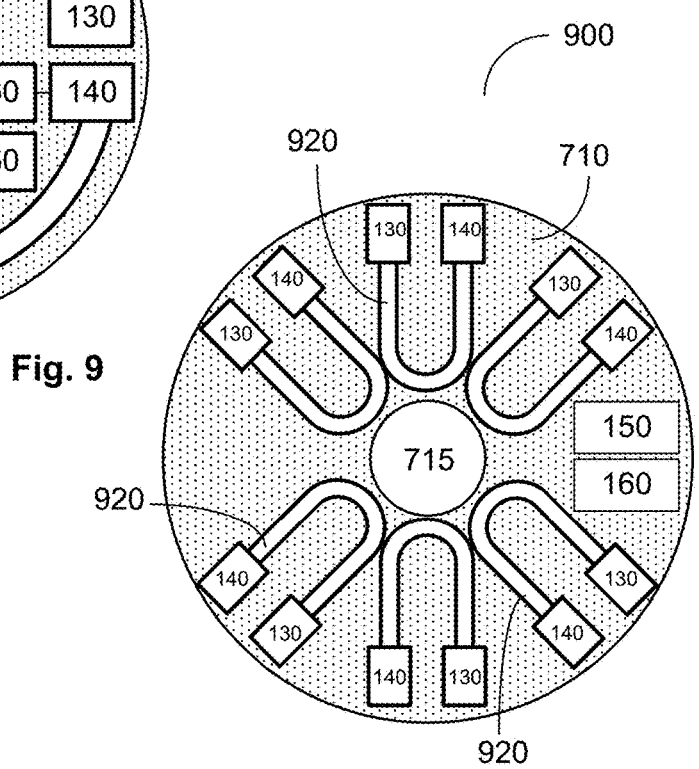
FIG. 9 shows an embodiment of a wearable breast monitor.

FIG. 9 shows an embodiment of a wearable breast monitor. Wearable breast monitor 900 includes flexible substrate 710 including nipple access portion 715. Wearable breast monitor 900 further includes one or more optical fibers 920 associated with flexible substrate 710. In this non-limiting example, the one or more optical fibers 920 form multiple U-shapes on the flexible substrate 710 in which the optical fibers 920 loop back on themselves. Wearable breast monitor 900 further includes at least one light source 130 operably coupled to the one or more optical fibers 920 and at least one photodetector 140 positioned to detect light reception from the one or more optical fibers 920. In this non-limiting example, each of the U-shaped configurations of optical fibers 920 includes at least one light source 130 and at least one photodetector 140. Wearable breast monitor 900 further includes reporting device 150 and microcontroller 160 including a microprocessor and circuitry, wherein the circuitry includes input circuitry, calculation circuitry, and reporting circuitry configured to receive and process information from the at least one photodetector 140 to calculate a breast volume delta value and to transmit information to reporting device 150 based on the breast volume delta value.

In an aspect, the flexible substrate of the wearable breast monitor includes an adhesive layer on at least one surface. In some embodiments, a wearable breast monitor having a flexible substrate in the form of a strip or a sleeve is configured for reversible attachment to the skin surface of the at least a portion of the one or more breasts of the subject. In some embodiments, the flexible substrate includes an adhesive layer on a surface of the flexible substrate intended to come in contact with the external contours of the at least a portion of the at least one of the one or more breasts of a subject. For example, the flexible substrate, e.g., a flexible strip, can include a biocompatible and reversible adhesive for temporarily adhering the flexible substrate to the surface of a breast of a nursing mother. In some embodiments, the flexible substrate includes an adhesive layer on a surface of the flexible substrate intended to come in contact with an inner surface of a brassiere. For example, the flexible substrate, e.g., a flexible sleeve, can include an adhesive for adhering the flexible substrate to the inner surface of a nursing bra. In an aspect, the adhesive is reusable. For example, the flexible substrate including the adhesive can be attached and removed from the surface of the breast of a nursing mother one or more times. For example, the flexible substrate including the adhesive can be attached and removed from the inner surface of a nursing bra one or more times. In an aspect, the flexible substrate includes an adhesive on a first surface of the flexible substrate intended to come in contact with the external contours of the at least a portion of the at least one of the one or more breasts of the subject and on a second surface of the flexible substrate intended to come in contact with an inner surface of a bra. In this way, the flexible substrate can be held in place during a breastfeeding event.

In an aspect, the adhesive layer includes, but is not limited to, an acrylic adhesive, a natural rubber adhesive, synthetic rubber adhesive, silicone adhesive, vinyl ester adhesive, vinyl ether adhesive, acrylic or vinyl water-containing adhesive and the like conventionally used for medical applications. The thickness of the adhesive layer is generally 5-2000 microns, preferably 10-1000 microns. In an aspect, at least one surface of the flexible substrate includes a reversible adhesive. In an aspect, the adhesive includes a pressure-sensitive adhesive. In an aspect, the pressure-sensitive adhesive includes a rubber based pressure-sensitive adhesive, an acrylic based pressure-sensitive adhesive, a silicone based pressure-sensitive adhesive, or the like. For example, a surface of the flexible substrate intended for placement on the breast region of the lactating female can include a pressure sensitive adhesive. In some embodiments, the reversible adhesive can be one or more pressure sensitive adhesives, e.g., adhesive tape, applicable for skin contact. For example, the wearable breast monitor can be adhered to the surface of a breast with one or more strips of medical-rated double-stick tape. As another example, the wearable breast monitor can be adhered to the surface of a breast with a coating of adhesive, e.g., URO-Bond® IV Silicone Skin Adhesive (from, UROCARE Products, Pomona, Calif.). Non-limiting examples of adhesives designed for healthcare use include any of a number of silicone-based pressure sensitive adhesives from, for example, Dow Corning, Midland, Mich. or 3M, St. Paul, Minn.

In an aspect, the adhesive layer on at least one surface of the flexible substrate includes a pressure-sensitive adhesive coating on the surface of a thin film. In an aspect, the pressure-sensitive adhesive coating covers at least a portion of at least one surface of the thin film. In an aspect, the one or more thin films are stackable. In an aspect, peeling away a thin film on the top of a stack of thin films reveals an underlying thin film including a pressure-sensitive adhesive coating. For example, the flexible substrate can include a stack of peelable thin films, each thin film including an adhesive (e.g., a pressure-sensitive adhesive coating) on a surface of the thin film intended to be in contact with the skin surface of the breast and/or the inner surface of a brassiere.

In some embodiments, a wearable breast monitor having a flexible substrate in the form of a strip or sleeve is configured for placement between the skin surface of the breast of the subject and a form-fitting garment. For example, the strip or sleeve forming the wearable breast monitor can be placed on the skin surface of the breast and held in place with a tight fitting shirt, tube-top, or undergarment. For example, the strip or sleeve forming the wearable breast monitor can be placed on the skin surface of the breast and held in place with a tight fitting brassiere or nursing bra.

In some embodiments, a wearable breast monitor having a flexible substrate in the form of a flexible strip or a flexible sleeve is configured for attachment to a garment. In an aspect, the garment is fabricated from a form-fitting material and the flexible strip or flexible sleeve forming the wearable breast monitor is attached to a surface of the garment. In an aspect, the garment includes a shirt, a tube top, or an undergarment. In some embodiments, the wearable breast monitor is attached to an outer surface of the garment. In some embodiments, the wearable breast monitor is attached to an inner surface of the garment. For example, the wearable breast monitor can be configured for attachment to an inner surface of a cup region of a nursing bra or similar garment. In an aspect, the flexible strip or flexible sleeve forming the wearable breast monitor is attached to an inner surface of a garment through one or more of an adhesive, snaps, VELCRO, or similar attachment means.

Figure 10:
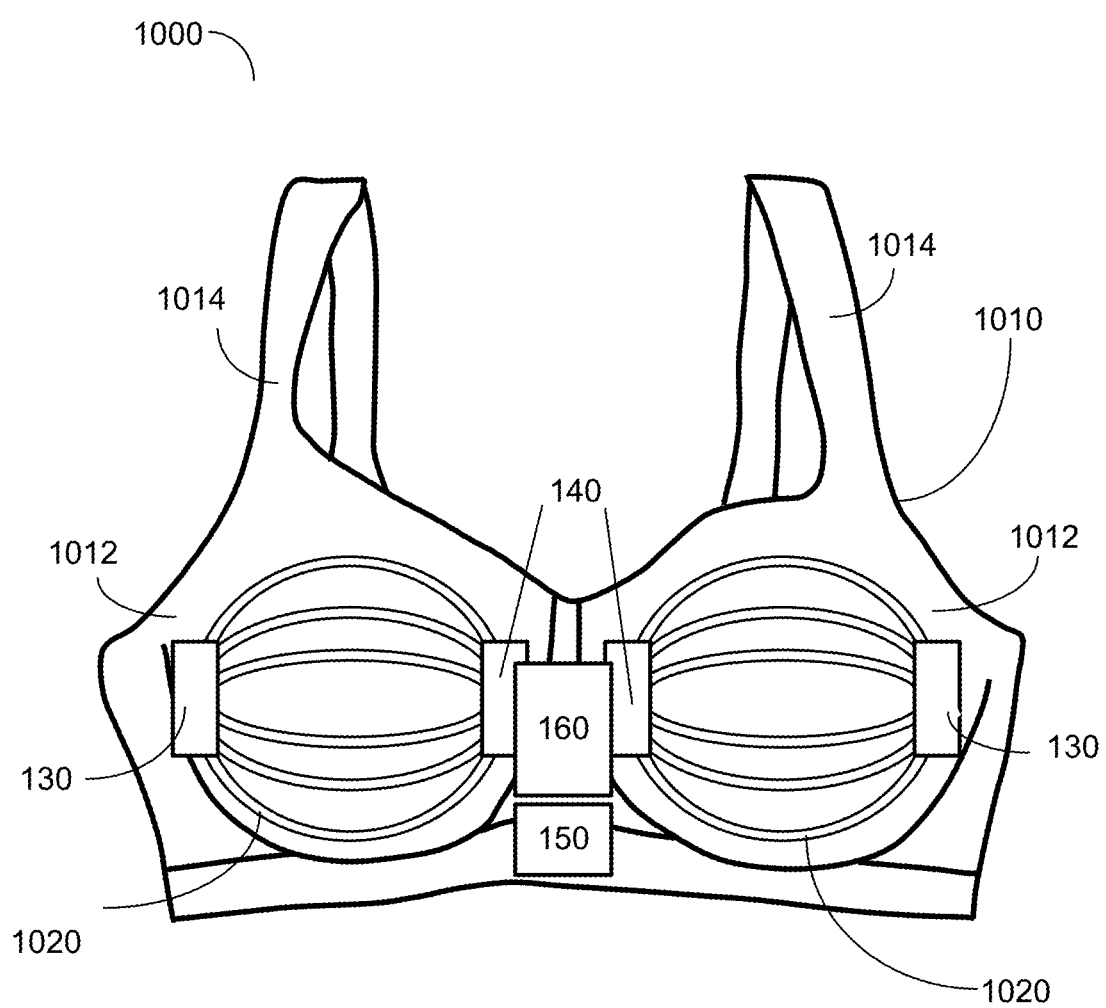
FIG. 10 shows an embodiment of a wearable breast monitor associated with a brassiere.

In some embodiments, the flexible substrate is a brassiere. FIG. 10 shows a non-limiting example of a wearable breast monitor incorporated into a brassiere. Wearable breast monitor 1000 includes flexible substrate 1010. In this non-limiting example, flexible substrate 1010 takes the form of a typical brassiere including cups 1012 intended to fit snuggly around each of the breasts and straps 1014 intended to support the breasts in cups 1012. In some embodiments, the flexible substrate can include a dedicated nursing bra. Wearable breast monitor 1000 further includes optical fibers 1020 arranged in a pattern on or in the cups 1012 of flexible substrate 1010. In this non-limiting example, the optical fibers 1020 span from the medial side to the lateral side of cups 1012. Also in this non-limiting example, at least one light source 130 is positioned on the lateral side of each cup 1012 while at least one photodetector 140 is position on the medial side of each cup 1012. Light source 130 is operably coupled to a first end of optical fibers 1020 and at least one photodetector 140 is operably coupled to a second end of optical fibers 1020. In some embodiments, at least one photodetector 140 is positioned along the length of optical fibers 1020. Wearable breast monitor 1000 further includes microcontroller 160 including a microprocessor and circuitry, wherein the circuitry includes input circuitry configured to receive a first set of signals from the at least one photodetector 140; and receive at least one second set of signals from the at least one photodetector 140; calculation circuitry configured to calculate a curvature delta value based on a comparison of the received first set of signals and the received at least one second set of signals from the at least one photodetector 140; and reporting circuitry configured to transmit a signal to the reporting device 150 based on the calculated breast volume delta value. Reporting device 150 can include a haptic reporting device, an audio reporting device, an optical reporting device and/or a transmission unit configured to transmit a signal including information regarding a calculated breast volume delta value.

In an aspect, a wearable breast monitor is incorporated into a nursing bra. In some embodiments, a wearable breast monitor includes a nipple access portion defined by the flexible substrate, wherein the nipple access portion includes an aperture sized to accommodate a nipple associated with the breast. In an aspect, the wearable breast monitor further includes a nipple access covering, wherein the nipple access covering is sized to cover at least a portion of the nipple access portion. In some embodiments, the nipple access covering is an extension of the flexible substrate sized to cover the nipple access portion and includes at least one fastener configured to reversibly attach the extension of the flexible substrate to the flexible substrate over the nipple access portion. In some embodiments, the nipple access covering is a separate piece of material sized to cover the nipple access portion and includes at least one fastener configured to reversibly attach the separate piece of material to the flexible substrate over the nipple access portion. For example, the nipple access covering can be formed from the same material as the flexible substrate. For example, the nipple access covering can be formed from a material that is different from the flexible substrate. In an aspect, the fastener includes at least one of a snap, a button, a zipper, a hook and loop fastener, VELCRO, or an adhesive. In an aspect, the nipple access covering is held on and/or over the nipple access portion by virtue of friction with the flexible substrate material.

Figure 11:
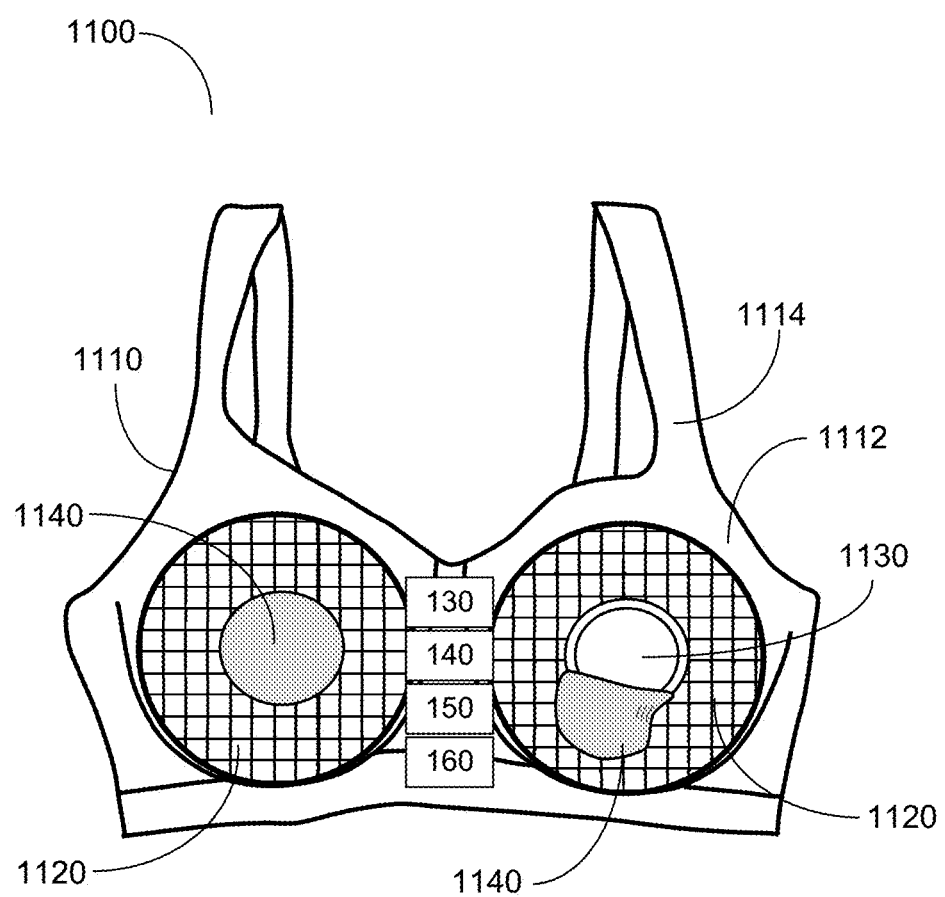
FIG. 11 shows an embodiment of a wearable breast monitor associated with a nursing bra.

FIG. 11 illustrates a non-limiting example of a wearable breast monitor including a nipple access portion and nipple access covering. Wearable breast monitor 1100 includes flexible substrate 1110. In this non-limiting example, flexible substrate 1110 takes the form of a nursing bra including cups 1112 intended to fit snuggly around each of the breasts and straps 1114 intended to support the breasts in cups 1112. Wearable breast monitor 1100 further includes nipple access portion 1130 defined by flexible substrate 1110, wherein nipple access portion 1130 includes an aperture sized to accommodate a nipple associated with a subject's breast (not shown). Wearable breast monitor 1100 further includes nipple access covering 1140 sized to cover at least a portion of nipple access portion 1130. In this non-limiting example, nipple access covering 1140 is a separate piece of material sized to cover the nipple access portion 1130 and including at least one fastener (not shown) configured to reversibly attach the separate piece of material to flexible substrate 1110 over nipple access portion 1130. Wearable breast monitor 1100 further includes optical fibers 1120 arranged in a pattern on or in the cups 1112 of flexible substrate 1110. In this non-limiting example, the optical fibers 1120 form a grid pattern on cups 1112. In this non-limiting example, wearable breast monitor 1100 includes at least one light source 130 and at least one photodetector 140 positioned in a central portion of the wearable breast monitor 1100 between cups 1112. It is contemplated that the light sources and the photodetectors can be located in other locations on the wearable breast monitor, depending upon the positioning of the optical fibers and what type of light reception is being measured from said optical fibers. Wearable breast monitor 1100 further includes microcontroller 160 including a microprocessor and circuitry, wherein the circuitry includes input circuitry configured to receive a first set of signals from the at least one photodetector 140; and receive at least one second set of signals from the at least one photodetector 140; calculation circuitry configured to calculate a curvature delta value based on a comparison of the received first set of signals and the received at least one second set of signals from the at least one photodetector 140; and reporting circuitry configured to transmit a signal to the reporting device 150 based on the calculated breast volume delta value. Reporting device 150 can include a haptic reporting device, an audio reporting device, an optical reporting device and/or a transmission unit configured to transmit a signal including information regarding a calculated breast volume delta value.

Returning to FIG. 2, wearable breast monitor 100 includes one or more optical fibers 120 associated with the flexible substrate 110. In an aspect, the optical fiber is a cylindrical dielectric waveguide that transmits light along its axis by a process of total internal reflection. In an aspect, the optical fiber includes a core surrounded by a cladding layer. In an aspect, both the core and the cladding layers are made of dielectric materials. In an aspect, the refractive index of the core is greater than the refractive index of the cladding. In an aspect, the optical fiber is a step-index fiber with an abrupt boundary between the core and the cladding. In an aspect, the optical fiber is a graded-index fiber with a gradual boundary between the core and the cladding. In an aspect, the one or more optical fibers are single mode fibers with a relatively narrow diameter through which only one mode will propagate. In an aspect, single mode fibers are coupled with a narrow spectral width light source. In an aspect, the one or more optical fibers are multimode fibers.

In an aspect, the one or more optical fibers 120 are one or more plastic optical fibers 206. In an aspect, the one or more optical fibers 120 are one or more polymer optical fibers 208. In an aspect, the one or more optical fibers 120 are one or more acrylic optical fibers 210. For example, the one or more optical fibers can include a core formed from acrylic polymer PMMA (polymethyl-methacrylate) or polystyrene and cladding formed from fluorinated polymers or silicone resin. In an aspect, the one or more optical fibers can include graded-index (GI-POF) fiber based on an amorphous fluoropolymer, e.g., poly(perfluoro-butenylvinyl ether) (CY-TOP). In some embodiments, the plastic or polymer optical fibers have a core/cladding interface that includes a step-index profile. In some embodiments, the plastic or polymer optical fibers have a core/cladding interface that includes a graded-index profile. In general, plastic or polymer optical fibers (POFs) are available from commercial sources, e.g., Edmund Optics, Inc., Barrington, N.J.

In an aspect, the one or more optical fibers 120 are one or more glass optical fibers 212. In an aspect, all or part of the one or more optical fibers are formed from silica glass. In an aspect, all or part of the one or more optical fibers are formed from silica glass doped with various materials to change the refractive index. For example, the silica glass can be doped with germanium dioxide or aluminum oxide to raise the refractive index. For example, the silica glass can be doped with fluorine or boron trioxide to lower the refractive index. Depending upon the desired refractive properties of the optical fiber, the core and/or the cladding can be doped. In an aspect, the one or more optical fibers are formed from aluminosilicate glass, germanosilicate glass, fluorosilicate glass, phosphosilicate glass, or borosilicate glass. Other non-limiting examples of glasses for use in forming optical fibers include fluorozirconate glass, fluoroaluminate glass, and chalcogenide glasses. Other crystalline materials can be used including, for example, sapphire. In an aspect, the one or more optical fibers are formed from fluoride glasses. For example, the one or more optical fibers can be formed from fluoride glass composed of fluorides of various metals, For example, the one or more optical fibers can be formed from heavy metal fluoride glasses. For example, the one or more glass fibers can be formed from the ZBLAN glass group including fluoride glass including zirconium, barium, lanthanum, aluminum, and sodium fluorides.

In an aspect, the one or more optical fibers 120 are formed from phosphate glass. For example, the one or more optical fibers can include a phosphate glass formed from metaphosphates of various metals. For example, the one or more optical fibers can include phosphorus pentoxide. In some embodiments, the one or more optical fibers are formed from a combination of fluoride and phosphate glass (e.g., fluorophosphate glass).

In an aspect, the one or more optical fibers 120 are formed from chalcogenide glass. For example, the one or more optical fibers are formed from a combination of chalcogens (elements in group 16 of the periodic table, e.g., sulfur, selenium, and tellurium) and more electropositive elements (e.g., silver).

In some embodiments, the one or more optical fibers 120 are photonic crystal fibers 214. In an aspect, the one or more optical fibers are microstructured or holey fibers that include photonic crystal to form the cladding around the core of the fiber. For example, the one or more optical fibers can include a central core and a cladding comprised of hexagonal air holes formed in silica. See, e.g., Roberts, et al. "Ultimate low loss of hollow-core photonic crystal fibres," Optics Express, 13:236-244, which is incorporated herein by reference. Photonic crystal fibers with a hollow core are available from commercial sources (from, e.g., NKT Photonics, Ontario, Canada). The photonic crystal fibers can include air guided, nonlinear, polarization maintaining, endlessly single mode, or large-mode-area fibers (see, e.g., Thorlabs, Inc., Newton, N.J.). In an aspect, the wearable breast monitor includes one or more photonic crystal fibers, wherein the calculation circuitry 184 is configured to calculate the curvature delta value based upon a difference in optical modal structure associated with a first set of signals and a second set of signals.

In an aspect, an optoelectronic instrument can be used to characterize a property of the one or more optical fibers. In an aspect, the optoelectronic instrument includes an optical time-domain reflectometer. In an aspect, the optical time-domain reflectometer injects a series of optical pulses into the fiber under tests and extracts, from the same end of the fiber, light that is scattered (Rayleigh backscatter) or reflected back from points along the fiber. The scattered or reflected light is used to characterize the optical fiber. The strength of the return pulses can be measured and integrated as a function of time, and plotted as a function of fiber length.

In some embodiments, one or more portions along the length of the one or more optical fibers 120 are rendered transmissive to light, and wherein the amount of light transmitted out is dependent on the curvature of the one or more optical fibers. In some embodiments, each of the one or more optical fibers 120 includes an inner core and an outer cladding, wherein a portion of a core/cladding interface is modified to alter light transmission, and wherein the amount of light transmitted out is dependent on the curvature of the one or more optical fibers.

In some embodiments, at least one of the one or more optical fibers 120 has a cladding component having a first optical absorption coefficient and a core component having a second optical absorption coefficient. In an aspect, at least one first photodetector 140 is configured to detect light reception from the core component and at least one second photodetector 140 is configured to detect light reception from the cladding component; and wherein the calculation circuitry 184 is configured to calculate positional information related to the curvature based upon a difference between signals from the at least one first photodetector 140 and signals from the at least one second photodetector 140.

In some embodiments, at least one of the one or more optical fibers 110 includes one or more fiber Bragg gratings. In an aspect, the fiber Bragg gratings include periodic or quasiperiodic orthogonal perturbations of the refractive index along the length of an optical fiber. The grating structure can be constructed in short segments along the length of the optical fiber to reflect particular wavelengths of light and transmits all others. For example, a periodic variation in the refractive index of the fiber core can be created to generate a wavelength-specific dielectric mirror. In an aspect, the fiber Bragg gratings are created by "inscribing" or "writing" systematic variation of refractive index into the core of an optical fiber using an intense ultraviolet source, such as an UV laser. The structure of the fiber Bragg grating can vary via the refractive index, or the grating period. Grating period can be uniform or graded, and either localized or distributed in a superstructure. The grating can be uniform, blazed, chirped, apodized, and/or superstructured.

In an aspect, the one or more optical fibers 120 are attached to the flexible substrate 110. For example, the one or more optical fibers can be adhered with an adhesive material to the flexible substrate. For example, the one or more optical fibers can be sewn onto the flexible substrate. In an aspect, the one or more optical fibers 120 are incorporated into the flexible substrate 110. For example, the one or more optical fibers can be embedded into an elastic fabric during a knit fabrication process. In some embodiments, the one or more optical fibers are at least one of attached, woven, incorporated, or embedded into an external surface of the flexible substrate. For example, the one or more optical fibers can be sewn into a flexible fabric, e.g., nylon, Lycra, or similar material. See, e.g., Ghosh et al (2005) "Development of a sensor-embedded flexible textile structure for apparel or large area applications," Indian J Fibre & Textile Res., 30:42-48; Krebber (2013) "Smart technical textiles based on fiber optic sensors" pp. 319-344 (INTECH; *Current Developments in Optical Fiber Technology*; dx.doi.org/10.5772/54244; accessed Nov. 17, 2016), which are incorporated herein by reference. In an aspect, the one or more optical fibers 120 are woven into the flexible substrate 110. For example, the optical fiber strands can be woven into a fabric-based flexible substrate. See, e.g., U.S. Pat. No. 7,630,591 titled "Optical fiber substrate useful as a sensor or illumination device component," to Allen et al., which is incorporated herein by reference.

In an aspect, the flexible substrate 110 includes a first layer and a second layer, and wherein the one or more optical fibers 120 are disposed between the first and the second layer of the flexible substrate. For example, the one or more optical fibers can be disposed between a first layer and a second layer of a cup portion of a brassiere or nursing bra. For example, the one or more optical fibers can be disposed between a first layer and a second layer forming a flexible strip or flexible sleeve. In an aspect, the first layer of the flexible substrate 110 and the second layer of the flexible substrate 110 are formed from a stretchable fabric. For example, the one or more optical fibers can be disposed between two layers of stretchable spandex or polyester fabric.

In some embodiments the wearable breast monitor includes one or more optical fibers arranged in a pattern on or in the flexible substrate. In some embodiments, the optical fibers are arranged on or in the flexible substrate in a linear pattern (see, e.g., FIG. 3, 320). For example, the optical fibers can be positioned linearly on a flexible strip or sleeve forming the base of the wearable breast monitor. In some embodiments, the optical fibers are arranged on or in the flexible substrate in a loop or U-shaped pattern (see, e.g., FIG. 4, 420; FIG. 9, 920). In some embodiments, the optical fibers are arranged on or in the flexible substrate in a curved pattern (see, e.g., FIG. 8, 820; FIG. 10, 1020). For example, the optical fibers can be arranged in a serpentine pattern on or in the flexible substrate. For example, the one or more optical fibers can span at least a portion of the distance around the base of the breast. For example, the one or more optical fibers can span a distance between the medial side and the lateral side of a breast in a curved configuration.

In an aspect, the one or more optical fibers are aligned with specific anatomical features of the breast. For example, the one or more optical fibers can span at least a portion of the distance between the clavicle and the nipple. For example, the one or more optical fibers can span at least a portion of the distance between the inframammary fold and the nipple. For example, the one or more optical fibers can span at least a portion of a circumference around a portion of the breast. For example, the one or more optical fibers can span at least a distance between the lateral breast crease and the nipple. For example, the one or more optical fibers can span at least a distance between the midline of the breast bone and the nipple.

FIGS. 12-16 illustrate additional non-limiting examples of patterns of optical fibers on or in the flexible substrate of a wearable breast monitor. In an aspect, the one or more optical fibers are arranged on or in the flexible substrate in a network. For example, the wearable breast monitor can include one or more optical fibers forming a network over at least a portion of the flexible substrate. In an aspect, the one or more optical fibers are arranged on or in the flexible substrate in a radial pattern. FIG. 12 shows a non-limiting example. In this case, wearable breast monitor 1200 includes flexible substrate 1210 including optical fibers 1220 shown radiating out from a nipple access portion 1215. In an aspect, the one or more optical fibers are arranged on or in the flexible substrate in a spiral pattern. FIG. 13 shows a non-limiting example. In this case, wearable breast monitor 1300 includes flexible substrate 1310 including optical fibers 1320 in a pattern spiraling out from nipple access portion 1315. In an aspect, at least two of the one or more optical fibers are arranged on or in the flexible substrate in concentric circles. FIG. 14 shows a non-limiting example. In this case, wearable breast monitor 1400 includes flexible substrate 1410 including optical fibers 1420 forming concentric circles centered around nipple access portion 1415. In an aspect, the one or more optical fibers are arranged on or in the flexible substrate in overlapping patterns. FIG. 15 shows a non-limiting example. In this case, wearable breast monitor 1500 includes flexible substrate 1510 including optical fibers 1520*a* radiating out from nipple access portion 1515 and overlapping optical fibers 1520*b* forming concentric circles centered around nipple access portion 1515. In an aspect, at least two of the one or more optical fibers are proximate and non-parallel. In an aspect, a first optical fiber overlays a second non-parallel optical fiber. In an aspect, a first portion of at least one of the one or more optical fibers overlays a second non-parallel portion of the at least one of the one or more optical fibers. In an aspect, the one or more optical fibers are arranged on or in the flexible substrate in a grid-like network. For example, the optical fibers can be arranged in a mesh configuration incorporated into the flexible substrate, e.g., stretchable fabric, of the wearable breast monitor. FIG. 16 shows a non-limiting example. In this case, wearable breast monitor 1600 includes flexible substrate 1610 including optical fibers 1620 forming a mesh or grid-like network or pattern.

Returning to FIG. 2, wearable breast monitor 100 includes at least one light source 130 operably coupled to the one or more optical fibers 120. The at least one light source provides light to the optical fiber wave guide. In an aspect, the at least one light source is optimized for suitable physical dimensions, suitable radiation pattern (beam width), linearity and large dynamic ranges (output power proportional to driving current), ability to be directly modulated at high speeds (fast response time), adequate output power to overcome channel losses, narrow spectral width, thermal stability, reliability, cost considerations, direct modulation considerations, driving circuit considerations, and conversion efficiency.

In an aspect, the at least one light source 130 provides at least one of ultraviolet, visible, and/or near infrared light to the one or more optical fibers. In an aspect, the at least one light source 130 provides visible light ranging from about 380 nm to about 800 nm. In some embodiments, the at least one light source 130 provides a broad spectrum of light. For example, the light source can provide white light to the one or more optical fibers. In some embodiments, the at least one light source 130 provides light of limited wavelength. For example, the light source can provide blue, green, yellow, orange, or red light to the one or more optical fibers. In an aspect, the at least one light source is configured to provide a continuous stream of photons. In an aspect, the at least one light source is configured to provide a pulse of photons.

In an aspect, the at least one light source 130 includes at least one light emitting diode (LED) 216. In an aspect, the wavelength of light emitted by the LED is a wavelength between 550 nm and 1670 nm. In an aspect, the wavelength emitted by the LED is near infrared. In an aspect, the LED is fabricated from one or more of gallium phosphide, aluminum arsenide, gallium arsenide, indium phosphide, aluminum-gallium arsenide, or indium-gallium-arsenide-phosphide. For example, gallium aluminum arsenide might be used for short-wavelength emissions (770-870) and indium gallium arsenide phosphide might be used for long-wavelength emissions (1100-1670 nm). Depending upon the composition of the LED, the emitting light can be shades of red, orange, yellow, green, and blue (e.g., gallium nitride (GaN) and indium gallium nitride (InGaN). Depending upon the application, the LED can be an edge-emitting LED (ELED) with high output power, narrow emission spectra, and narrow beam pattern or a surface emitting LED (SLED) with low-to-moderate output power and a broader beam pattern. In an aspect, the LED light source has a high radiance, fast response time, and high quantum efficiency.

In an aspect, the at least one light source 130 includes at least one laser diode 218. In an aspect, the at least one light source includes an electrically pumped semiconductor laser in which the active laser medium includes a p-n junction of a semiconductor diode. In an aspect, the at least one light source 130 includes an injection laser diode. In an aspect, the at least one light source includes a PIN diode. Laser diodes that emit at a variety of wavelengths are commercially available (from, e.g., Thorlabs, Inc., Newton, N.J.).

In an aspect, the at least one light source is configured to emit one or more pulses of light. For example, the light source can include a pulsed laser diode. In an aspect, the pulsed light source is at least one of Q-switched, gain-switched, mode-locked, superpulsed, and/or chopped or gated. In an aspect, the pulsed light source has a frequency in the 2.5 to 10,000 Hz ranges. In an aspect, the pulsed light source has pulse durations in the range of a few milliseconds. In some embodiments, pulsed light from the at least one light source is used to detect changes in curvature of the breast during a breastfeeding event. In an aspect, the at least one photodetector is configured to measure a time delta between its reception of light and emission of light by the at least one light source; and wherein the calculation circuitry is configured to calculate positional information related to the curvature based upon the time delta.

With reference to FIG. 2, wearable breast monitor 100 includes at least one photodetector 140 positioned to detect light reception from the one or more optical fibers 120. In an aspect, the at least one photodetector 140 is positioned along the one or more optical fibers to detect light transmission through the one or more optical fibers 120 from the at least one light source 130. In an aspect, the at least one photodetector 140 is at an end of the optical fiber opposite of the at least one light source 130. In an aspect, the at least one light source is positioned at a first end of the one or more optical fibers and the at least one photodetector is positioned at a second end of the one or more optical fibers. For example, the at least one photodetector can be positioned at the end of the one or more optical fibers to detect increase/decrease in light transmitted through the one or more optical fibers in response to changes in curvature of the breast during a breastfeeding event. In an aspect, the at least one photodetector 140 is positioned along the length of the one or more optical fibers 120 to detect light reflection from the one or more optical fibers 120. For example, the at least one photodetector can be positioned along a length of the optical fiber to detect an increase/decrease in photons escaping from the optical fiber in response to changes in curvature of the breast during a breastfeeding event. In an aspect, a plurality of photodetectors is positioned along a length of at least one of the one or more optical fibers.

In an aspect, a single photodetector is connected to the one or more optical fibers. For example, one or more optical fibers can be organized in a pattern such that the second ends of the optical fibers are operably coupled to the single photodetector. In an aspect, the optical fibers are connected to a light source at the first end and a photodetector at the second end. In between the light source and the photodetector the optical fibers may fan out in a pattern configured to cover the at least a portion of the breast. In an aspect, each of the optical fibers or bundles of optical fibers include a photodetector.

In some embodiments, the photodetector converts light signals from photons absorbed by the photodetector into voltage or current. In an aspect, the photodetector is a photodiode 220. For example, the photodetector can include a semiconductor photodiode that converts absorbed light, e.g., photons, into a current. In an aspect, photodiode 220 includes a p-n junction or PIN structure. In an aspect, photodiode 220 is a silicon, germanium, indium gallium arsenide, and/or mercury cadmium telluride based photodiode. In an aspect, photodiode 220 has a spectral response ranging from 190 nm to 1100 nm in wavelength. In some embodiments, photodiode 220 is response to longer wavelengths of electromagnetic energy.

In an aspect, the photodetector is a photoemission photodetector in which photons cause electrons to transition from a conduction band of material to free electrons in a vacuum or gas. For example, the photoemission photodetector can include a photomultiplier tube, photocathodes, and/or microchannel plate detectors. In an aspect, the photodetector is a photoelectric photodetector in which photons cause electrons to transition from a valence band to a conduction band of a semiconductor. For example, the photoelectric photodetector can include a complementary metal-oxide-semiconductor (CMOS) detector, charge-coupled devices (CCD), reverse-biased light emitting diodes, photoresistors, photodiodes, phototransistors, quantum dot photoconductors or photodiodes. Photoelectric photodetectors are available from commercial sources (from, e.g., OSRAM Opto Semiconductors, Regensburg, Germany). In an aspect the photodetector is a photovoltaic photodetector in which photons cause a voltage to develop across a depletion region of a photovoltaic cell. For example, the photovoltaic photodetector can include a type of solar cell. In some embodiments, the photodetector converts light signals from photons absorbed by the photodetector into heat. For example, the photodetector can be a thermal photodetector in which photons cause electrons to transition to mid-gap states then decay back to lower bands, inducing phonon generation and heat.

In some embodiments, the light signals from photons absorbed by the photodetector induce polarization effects. For example, the photodetector can be a polarization photodetector in which photons induce changes in polarization of suitable materials, which leads to a change in index of refraction or other polarization effects.

In some embodiments, the photodetector converts light signals from photons absorbed by the photodetector into a chemical reaction. For example, the photodetector can be a photochemical photodetector in which photons induce a chemical change in a material.

With reference to FIG. 2, wearable breast monitor 100 includes at least one reporting device 150. The reporting device 150 is operably coupled to the microcontroller 160 and configured to receive one or more signals transmitted from the reporting circuitry 186, the one or more signals including information regarding the calculated breast volume delta value. In turn, the reporting device 150 is configured to report information related to the calculated breast volume delta value. In some embodiments, the reporting device 150 is configured to provide a signal, e.g., a haptic, audio, or optical signal, to a nursing mother to indicate that sufficient breastmilk has been expressed during a particular breastfeeding event. Alternatively, the reporting device 150 is configured to provide a signal, e.g., a haptic, audio, and/or optical signal, designed to startle an infant into ceasing breastfeeding (i.e., disengaging from the nipple) if sufficient breastmilk has been expressed during a particular breastfeeding event.

In some embodiments, reporting device 150 includes a haptic reporting device 222. For example, the reporting device can include a haptic reporting device that emits a haptic signal, e.g., a vibrational signal, in response to the information regarding the calculated breast volume delta value. In an aspect, the haptic reporting device 222 is incorporated into or onto a surface of the flexible substrate that is in direct contact with a subject wearing the wearable breast monitor. For example, the haptic reporting device can be associated with an internal surface of a nursing bra. In an aspect, the haptic reporting device 222 is incorporated into or onto a surface of the flexible substrate that comes into direct contact with the nursing infant. In an aspect, the haptic reporting device 222 provides a haptic signal to startle an infant into ceasing breastfeeding if sufficient breast milk has been expressed during a breastfeeding event. For example, the haptic reporting device can be associated with an external surface of a nursing bra that comes into contact with a cheek or other portion of a nursing infant. For example, the haptic reporting device can include a vibrational motor (e.g., a coin or pancake vibration motor, from, e.g., Precision Microdrives Ltd, London, UK) that might be used to let the nursing mother know that sufficient breast milk has been expressed.

In some embodiments, the haptic reporting device 222 includes a device for inducing a mild electrical shock. For example, the haptic reporting device can emit a mild electric shock to let the nursing mother know that a sufficient volume of milk has been expressed. For example, the haptic reporting device can emit a mild electric shock to startle an infant into ceasing breastfeeding if sufficient breast milk has been expressed during a breastfeeding event.

In some embodiments, the reporting device 150 includes an audio reporting device 224. For example, the reporting device can include an audio reporting device including at least one speaker that emits an audible signal in response to the information regarding the calculated breast volume delta value. For example, the audio reporting device can emit a warning sound, e.g., a beeping sound, if the calculated breast volume delta value fails to fall within a range of acceptable breast volume delta values. For example, the audio reporting device can emit one or more spoken words indicating whether the calculated breast volume delta value falls within a range of acceptable breast volume delta values. In an aspect, audio reporting device 224 provides an audible signal to startle an infant into ceasing breastfeeding if sufficient breast milk has been expressed during a breastfeeding event. Electronic sound chips and/or sound cards for use as an audio reporting device are available from commercial sources (from, e.g., STMicroelectronics, Geneva, Switzerland).

In some embodiments, the reporting device 150 includes an optical reporting device 226. In an aspect, the optical reporting device includes one or more light indicators. For example, the reporting device can include one or more lights, e.g., light-emitting diodes (LEDs), configured to light up in response to the information regarding the calculated breast volume delta value. In an aspect, the optical reporting device includes one or more color-coded lights. For example, the reporting device can include LEDs of different colors and a coding system. For example, a signal from a green LED can indicate that the calculated breast volume delta value falls within a range of acceptable breast volume delta values while a red LED can indicate that the calculated breast volume delta value fails to fall within a range of acceptable breast volume delta values. In an aspect, optical reporting device 226 provides a visible single to startle an infant into ceasing breastfeeding if sufficient breast milk has been expressed during a breastfeeding event. As a non-limiting example, sewn-on washable LEDs designed for use with fabric are commercially available (from, e.g., SparkFun Electronics, Niwot, Colo.).

In an aspect, reporting device 150 includes transmission unit 228 including an antenna. A "transmission unit," as used herein, can be one or more of a variety of units that are configured to send and/or receive signals, such as signals carried as electromagnetic, radio, sonic, or optical waves. A transmission unit generally includes at least one antenna and associated circuitry. A transmission unit can be operably connected to the microcontroller and/or can include a processor and/or memory component. A transmission unit can be operably connected to an energy source, such as a battery. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. In an aspect, the transmission unit communicates within a wireless personal area network, e.g., Bluetooth, wireless USB, WiFi, or ZigBee.

In an aspect, the transmission unit 228 comprises a radiofrequency transmission unit. A transmission unit can include an oscillator and encoder configured to generate a programmable pulse position-modulated signal in the radio frequency range (see, e.g., U.S. Pat. No. 4,384,288, which is incorporated herein by reference). A transmission unit can include a radio frequency identification device (RFID), which can be a passive RFID device, a semi-passive RFID device, or an active RFID device, depending on the embodiment (see, e.g., Chawla & Ha, "An Overview of Passive RFID," *IEEE Applications and Practice*, 11-17 (September 2007), which is incorporated herein by reference). A transmission unit including an RFID device can be configured to transmit signals in the UHF standard range. A transmission unit can include a battery-assisted passive RFID device, such as sold by Alien Technology®, Morgan Hill, Calif. A transmission unit can include an optical transmission unit. For example, the optical transmission unit can include an infrared transmitting diode. A transmission unit can include a hybrid backscatter system configured to function in an RFID, IEEE 802.11x standard and Bluetooth system. A transmission unit can include a near field communication (NFC) device. A transmission unit can include a Wireless Identification and Sensing Platform (WISP) device. A transmission unit can be operably coupled to a data storage unit.

In an aspect, transmission unit 228 is configured to transmit the information regarding the calculated breast volume delta value to an external device. For example, the transmission unit can be configured to sync with an external device, e.g., a smart phone, to transfer information, e.g., data, regarding the calculated breast volume delta value. In an aspect, the transmission unit is configured to transmit the information regarding the calculated breast volume delta value to a dedicated handheld device. For example, the transmission unit can transmit information regarding the calculated breast volume delta value to a dedicated handheld device specifically designed for use with a wearable breast monitor or breast monitoring system. For example, a dedicated handheld device can include a transmission unit and antenna for communicating with the wearable breast monitor, a user interface, e.g., a display, microphone, or haptic interface, for displaying and/or notifying a user during a breastfeeding event, and a computing component to display and save information received from the wearable breast monitor. In an aspect, the transmission unit is configured to transmit the information regarding the calculated breast volume delta value to a mobile communication device. For example, the transmission unit can transmit the information related to the calculated breast volume delta value to a mobile communication device, e.g., a cellular or smart phone. For example, the transmission unit including the antenna can be connected through a wireless radiofrequency communication link, e.g., Bluetooth or WiFi, to a smart phone. In an aspect, the mobile communication device includes a program, set of instructions, and/or an application configured to receive information from the wearable breast monitor, process the received information, and display the received information for a user, e.g., a nursing mother. In an aspect, the transmission unit is configured to transmit the information regarding the calculated breast volume delta value to a computing device. For example, the transmission unit can transmit the information related to the calculated breast volume delta value to a computing device, e.g., a tablet, a laptop, or tabletop computing device.

In an aspect, the transmission unit is configured to communicate with a communication device, such as one or more of a mobile communication device and a computer system including, but not limited to, mobile computing devices (e.g., hand-held portable computers, Personal Digital Assistants (PDAs), laptop computers, netbook computers, tablet computers, and so forth), mobile telephone devices (e.g., cellular telephones and smartphones), devices that include functionalities associated with smartphones and tablet computers (e.g., phablets), portable game devices, portable media layers, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. In an aspect, the computing device is associated with another piece of equipment associated with a patient care room in a hospital or other medical facility or lactation clinic.

In an aspect, the transmission unit is configured to transmit the information regarding the calculated breast volume delta value to a network. In an aspect, the transmission unit is configured to communicate with a health provider network. For example, the reporting device can be configured to communicate directly with a network associated with a subject's healthcare provider, e.g., a hospital, a clinic, medical facility, or physician's office. For example, the reporting device can be configured to communicate directly with the subject's electronic medical file or health record.

In an aspect, the transmission unit is configured to transmit the information regarding the calculated breast volume delta value to a social media site. In some embodiments, the transmission unit is configured to directly transmit information to a social media site. Alternatively, the transmission unit is configured to transmit the information regarding the calculated breast volume delta value to an external device, e.g., a dedicated handheld device, mobile communication device, or other computing device, which in turn transmits the information regarding the calculated breast volume delta value to a social media site. For example, the transmission unit can be configured to post the information regarding the calculated breast volume delta value to Facebook, Google, Instagram, CafeMom, or similar social media site. For example, the transmission unit can be configured to post the information regarding the calculated breast volume delta to a website dedicated to a specific topic, e.g., lactation or other parenting/baby topics. For example, the transmission unit can be configured to post the information regarding the calculated breast volume delta to a website that allows the nursing mother to track breastfeeding events, compare data with other nursing mothers, get advice on nursing/breastfeeding issues, and the like.

Wearable breast monitor 100 includes microcontroller 160 including microprocessor 170 and circuitry 180. In an aspect, the microcontroller includes a microprocessor 170, e.g., a central processing unit, for controlling one or more functions of the wearable breast monitor. In an aspect, the microprocessor is incorporated into one or more integrated circuits. In an aspect, the microprocessor is programmable, capable of accepting input data, processes the input data according to instructions, and provides results as output. The control unit further includes a system memory and a system bus that couples various system components including the system memory to the microprocessor. The microprocessor can include a processing unit, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an aspect, the microcontroller includes one or more ASICs having a plurality of pre-defined logic components. In an aspect, the microcontroller includes one or more FPGA having a plurality of programmable logic commands. In an aspect, the microcontroller includes embedded software.

The microcontroller 160 includes circuitry 180. In an aspect, the circuitry includes input circuitry 182 configured to receive a first set of signals from the at least one photodetector 140; and receive at least one second set of signals from the at least one photodetector 140. In an aspect, the signals from the at least one photodetector are indicative of the amount of photons detected by the photodetector at the end of the optical fiber or along the length of the optical fiber. The signal received by the input circuitry from the photodetector is proportionally related to changes in the curvature of the optical fibers and dependent upon the placement of the photodetector. For example, a decreased signal from a photodetector at the end of the optical fiber may be correlated with an increase in bending, whereas a decreased signal from a photodetector along the length of the optical fiber may be correlated with a decrease in bending. Similarly, an increase in signal from a photodetector at the end of the optical fiber may be correlated with a decrease in bending, whereas an increased signal from a photodetector along the length of the optical fiber may be correlated with an increase in bending.

The input circuitry 182 is configured to receive a first set of signals from the at least one photodetector 140. In some embodiments, the first set of signals is sent as soon as the wearable breast monitor is switched on. In some embodiments, the first set of signals is sent once the wearable breast monitor has made contact with a skin surface. In some embodiments, the first set of signals is sent in response to input from the subject. For example, the wearable breast monitor can include a "start button" or similar user interface for activating the device. For example, the wearable breast monitor can be configured to receive a "start" signal from a remote device, e.g., a dedicated hand-held device, mobile communication device, and/or computing device.

The input circuitry 182 is configured to receive at least one second set of signals from the at least one photodetector 140. In some embodiments, the input circuitry is configured to receive the at least one second set of signals periodically during a breastfeeding event. Alternatively or in addition, the input circuitry can be configured to receive the at least one second set of signals from the at least one photodetector at the end of a breastfeeding event. In some embodiments, the frequency at which signals are received is modulated by the at least one photodetector in terms of how frequently the photodetector monitors light reception. In some embodiments, the frequency at which signals are received is modulated by the input circuitry in terms of how frequently the circuitry samples for signals from the photodetectors.

Circuitry 180 includes calculation circuitry 184 configured to calculate a curvature delta value based on a comparison of the received first set of signals and the received at least one second set of signals from the at least one photodetector. For example, the circuitry can be configured to calculate a curvature delta value based on changes in voltage output from a photodetector in response to a change in curvature, e.g., change in breast volume during a breastfeeding event. In some embodiments, the microcontroller includes a look-up table that includes correlation data between light transmission, reflection, or refraction by a particular type or orientation of optical fiber versus the curvature of the optical fiber. It is anticipated that as the optical fiber bends, more photons are potentially lost from the optical waveguide. This may be measured as a decrease in light transmitted through the optical fiber or may be measured as an increase in light escaping from the optical fiber along its path.

A wearable breast monitor such as described herein includes calculation circuitry configured to calculate a breast volume delta value from a calculated curvature delta value. In an aspect, the calculation circuitry of the microcontroller includes an algorithm for calculating the breast volume delta value from the calculated curvature delta value.

In some embodiments, the calculation circuitry calculates the breast volume delta value based on changes in the height of the breast from the chest. From a geometric perspective, the breast can be considered a cap section of a sphere obtained by slicing the sphere with a plane. As such, a spherical cap has a circular base and a dome that is flatter than a hemispherical dome, the latter of which is a spherical cap obtained by cutting the sphere in half. The volume of a spherical cap can be calculated from its height H and its radius at the base A. R is the radius of the sphere from which the spherical cap is "cut." As such, H, A, and R are related as follows:

$$A^2 = 2RH - H^2$$

To find the volume in terms of the radius of the base A of the spherical cap and the height H of the spherical cap, the following equation can be used:

$$V = (\pi/6)H(3A^2 + H^2)$$

To find the volume in terms of the radius of the sphere R and the height H, the following equation can be used:

$$V = (\pi/3)H^2(3R - H)$$

Figure 17:
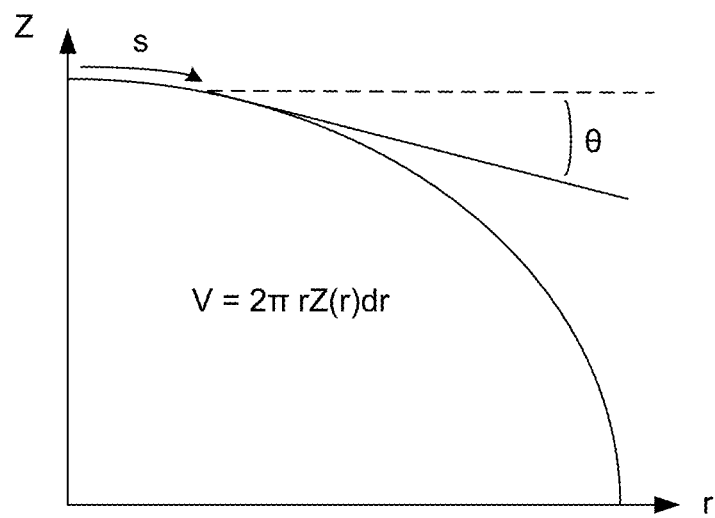
FIG. 17 shows calculations related to determining breast volume deltas from curvature deltas.

In some embodiments, for calculation purposes, the breast is treated as a rotationally symmetric breast. Said rotationally symmetric breast is raised above the chest by a height of $Z(r)$. The breast at the chest has a radius of r. FIG. 17 illustrates aspects of this scenario. In this case, the breast volume is given by the equation:

$$V = \int_0^R 2\pi r Z(r) dr$$

In some cases, the value of $Z(r)$ (the height of the breast above the chest) is not predefined. However, changes in this height during a breastfeeding event can be calculated based on changes in local curvature of the breast, as measured using the optical fibers of the wearable breast monitor. Let s be the arc-length along the surface of the curved breast and let $\mathcal{R}(s)$ be the inverse curvature, i.e., the radius of curvature. Let $\theta$ be the local slope angle. This is illustrated in FIG. 17. As such, $dr/ds = \cos\theta$; $dZ/dz = -\sin\theta$; and $ds/d\theta = \mathcal{R}$. Therefore, $dr/d\theta = \cos\theta$ and $dZ/d\theta = -\mathcal{R}\sin\theta$.

In some embodiments, the algorithm assumes a constant radius of curvature $\mathcal{R}$. As such the following it true:

$$r = \mathcal{R}\sin\theta$$

$$Z = Z_0 + \mathcal{R}(\cos\theta - 1)$$

$$s = \mathcal{R}\theta$$

Let R be the full radius of the breast and assume that $R < \mathcal{R}$. The maximum $\theta$ value is $\theta_*$, wherein $$\sin\theta_* = R/\mathcal{R}$$

Skin length $(s(\theta_*))$ along the curvature is equal to $$s_* = \mathcal{R}\theta_*$$

$Z_0$ is calculated by requiring that Z=0 at $\theta_*$. As such $$0 = Z_0 + \mathcal{R}(\cos\theta_* - 1)$$

$$Z_0 = \mathcal{R}(1 - \cos\theta_*)$$

$$Z = \mathcal{R}(\cos\theta - \cos\theta_*)$$

Based on these relationships, volume V can be calculated as follows:

$$V = 2\pi \int \mathcal{R}\sin\theta \, \mathcal{R}(\cos\theta - \cos\theta_*) \mathcal{R}\cos\theta \, d\theta$$

$$V = 2\pi \mathcal{R}^3 \int \cos\theta - \cos\theta_* \sin\theta \cos\theta \, d\theta$$

-continued
$$V = \pi \mathcal{R}^3/3 \, \{2 - 3\cos\theta_{\boxed{F}} + \cos 3\theta_{\boxed{F}}\}$$

where $\cos\theta_{\boxed{F}} = \sqrt{1 - R^2/\mathcal{R}^2}$.

In some embodiments, the radius of curvature $\mathcal{R}$ varies with the local slope angle θ. As such:

$$\mathcal{R}(\theta) = \mathcal{R}_0 - \mathcal{R}'\sin\theta$$

and:

$$s = \mathcal{R}_0\theta + \mathcal{R}'(\cos\theta - 1)$$

$$r = \mathcal{R}_0\sin\theta - \frac{1}{2}\mathcal{R}'\sin^2\theta$$

$$Z = Z_0 + \mathcal{R}_0(\cos\theta - 1) + \frac{\mathcal{R}'}{2}\theta - \frac{\mathcal{R}'}{4}\sin 2\theta$$

These variables can then be used to integrate to calculate a volume, where:

$$V = 2\pi \int_0^{\theta_F} \left[\mathcal{R}_0\sin\theta - \frac{1}{2}\mathcal{R}'\sin 2\theta\right]\left[Z_0 + \mathcal{R}_0(\cos\theta - 1) + \frac{\mathcal{R}'}{2}\theta - \frac{\mathcal{R}'}{4}\sin^2\theta\right]$$

$$[\mathcal{R}_0 - \mathcal{R}'\sin\theta]\cos\theta \, d\theta$$

$$V = 2\pi \int_0^{\theta_F} \left\{(Z_0 - \mathcal{R}_0) + \mathcal{R}_0\cos\theta - \frac{\mathcal{R}'}{2}\sin\theta\cos\theta + \frac{\mathcal{R}'}{2}\theta\right\}\left\{\mathcal{R}_0^2 - \frac{3}{2}\mathcal{R}_0\mathcal{R}'\sin\theta + \frac{1}{2}\mathcal{R}'^2\sin^2\theta\right\}\sin\theta\cos\theta \, d\theta \equiv \sum_{k=1}^{12} V_k$$

For other Z(r) shapes, r and Z can be numerically evaluated via $dr/d\theta = \mathcal{R}(\theta)\cos\theta$ and $dZ/d\theta = \mathcal{R}(\theta)\sin\theta$; and then numerically integrated $$V = 2\pi \int_0^{\theta} r(\varphi)Z(\varphi)\frac{dr}{d\varphi}d\varphi$$

For breasts which are not rotationally symmetric, Z(x,y) are found and then integrate for volume:

$$V = \iint Z(x,y)dxdy$$

Changes in the curvature of the breast as indicated by changes in the light emission properties of the optical fibers of the wearable breast monitor can be used to calculate a change in volume of the breast and by inference a volume of milk expressed during a breastfeeding event.

In some embodiments, the calculations assume that the mammalian breast is a dome shape with a flat circular bottom, rounded sides, and a rounded top. In an aspect, the calculations assume that the mammalian breast is a spherical cap. In an aspect, the calculations assume that the mammalian breast is an ellipsoid. In an aspect, the calculations assume that the mammalian breast is a paraboloid. In an aspect, the change in curvature is correlated with a change in surface area of at least a portion of the breast.

Figure 18:
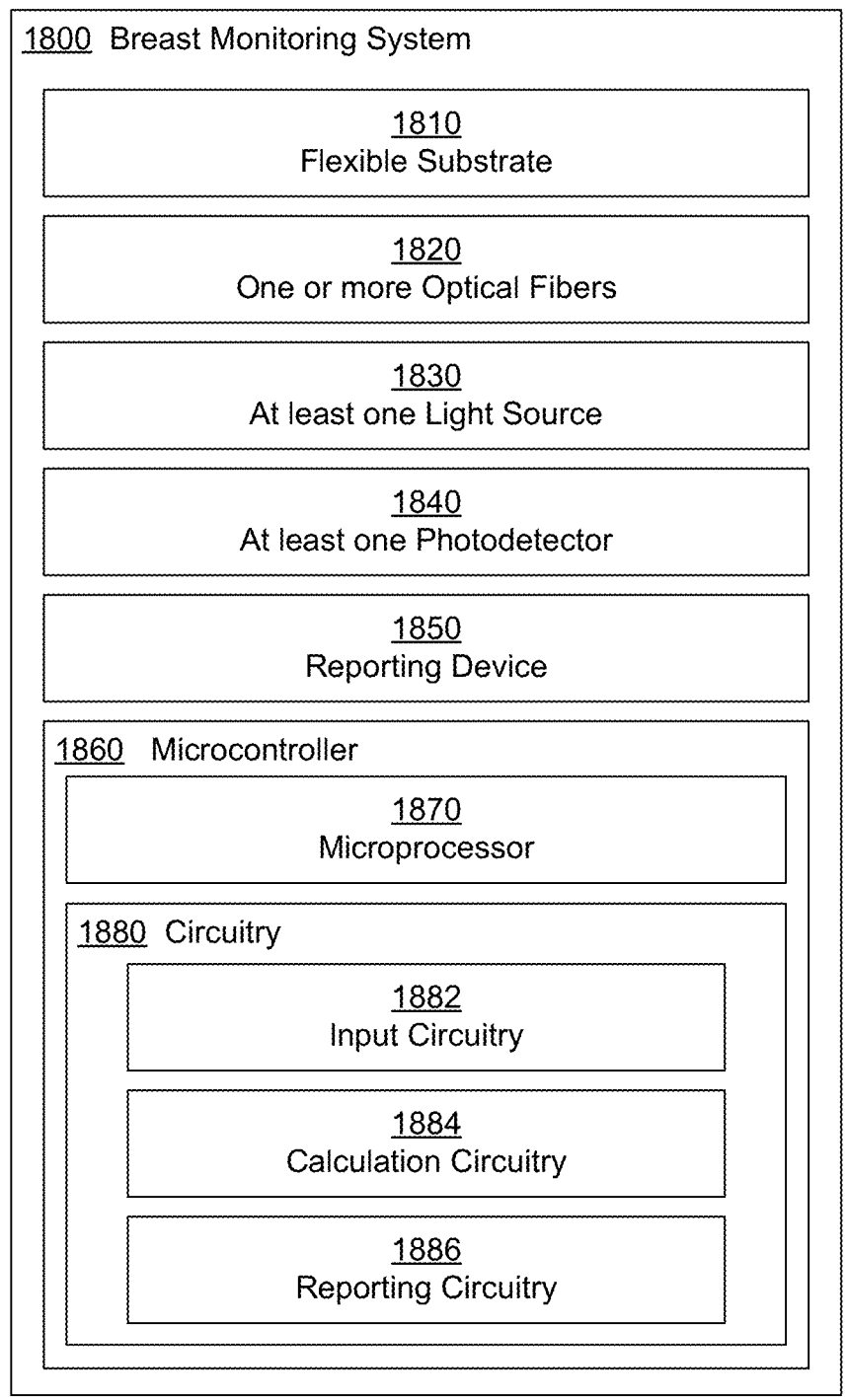
FIG. 18 is a block diagram of an embodiment of breast monitoring system.

Described herein are aspects of a breast monitoring system. FIG. 18 shows a non-limiting example of a breast monitoring system. Breast monitoring system 1800 includes a flexible substrate 1810 fabricated to substantially conform to external contours of at least a portion of one or more breasts of a subject; one or more optical fibers 1820 associated with the flexible substrate 1810, wherein the one or more optical fibers 1820 are dynamically bendable; at least one light source 1830 operably coupled to the one or more optical fibers 1820; at least one photodetector 1840 positioned to detect light reception from the one or more fibers 1820; a reporting device 1850; and a microcontroller 1860 including a microprocessor 1870 and circuitry 1880, wherein the circuitry includes input circuitry 1882 configured to receive a first set of signals from the at least one photodetector; and receive at least one second set of signals from the at least one photodetector; calculation circuitry 1884 configured to calculate a curvature delta value based on a comparison of the received first set of signals and the received at least one second set of signals from the at least one photodetector; and calculate a breast volume delta value from the calculated curvature delta value; and reporting circuitry 1886 configured to transmit a signal to the reporting device based on the calculated breast volume delta value.

In some embodiments, the components of breast monitoring system 1800 including one or more optical fibers 1820, at least one light source 1830, at least one photodetector 1840, reporting device 1850, and microcontroller 1860 including microprocessor 1870 and circuitry 1880 are all associated with and/or incorporated into flexible substrate 1810 to form a wearable breast monitoring system. In some embodiments, the breast monitoring system 1800 includes one or more optical fiber 1820, at least one light source 1820, at least one photodetector and the reporting device 1850 associated with the flexible substrate 1810, wherein the reporting device 1850 (e.g., a transmission unit) is in wireless communication with microcontroller 1860. Non-limiting aspects of flexible substrates, optical fibers, light sources, photodetectors, reporting devices, microcontrollers, and circuitry have been described above herein.

Described herein are aspects of a breast monitoring system. In an aspect, a breast monitoring system comprises a wearable breast monitor and a computing device, wherein the wearable breast monitor includes a flexible substrate fabricated to substantially conform to external contours of at least a portion of one or more breasts of a subject; one or more optical fibers associated with the flexible substrate, wherein the one or more optical fibers are dynamically bendable; at least one light source operably coupled to the one or more optical fibers; at least one photodetector positioned to detect light reception from the one or more optical fibers; and a transmission unit including an antenna and operably coupled to the at least one photodetector, the transmission unit configured to transmit signals, the transmitted signals including light reception information from the at least one photodetector; and the computing device including a receiver and a microprocessor with circuitry, the circuitry including input circuitry configured to receive a first set of transmitted signals from the transmission unit of the wearable breast monitor, and to receive at least one second set of transmitted signals from the transmission unit of the wearable breast monitor; calculation circuitry configured to calculate a curvature delta value based on a comparison of the received first set of transmitted signals and the received at least one second set of transmitted signals form the transmission unit of the wearable breast monitor, and calculate a breast volume delta value from the calculated curvature delta value; and reporting circuitry configured to report the calculated breast volume delta value.

Figure 19:
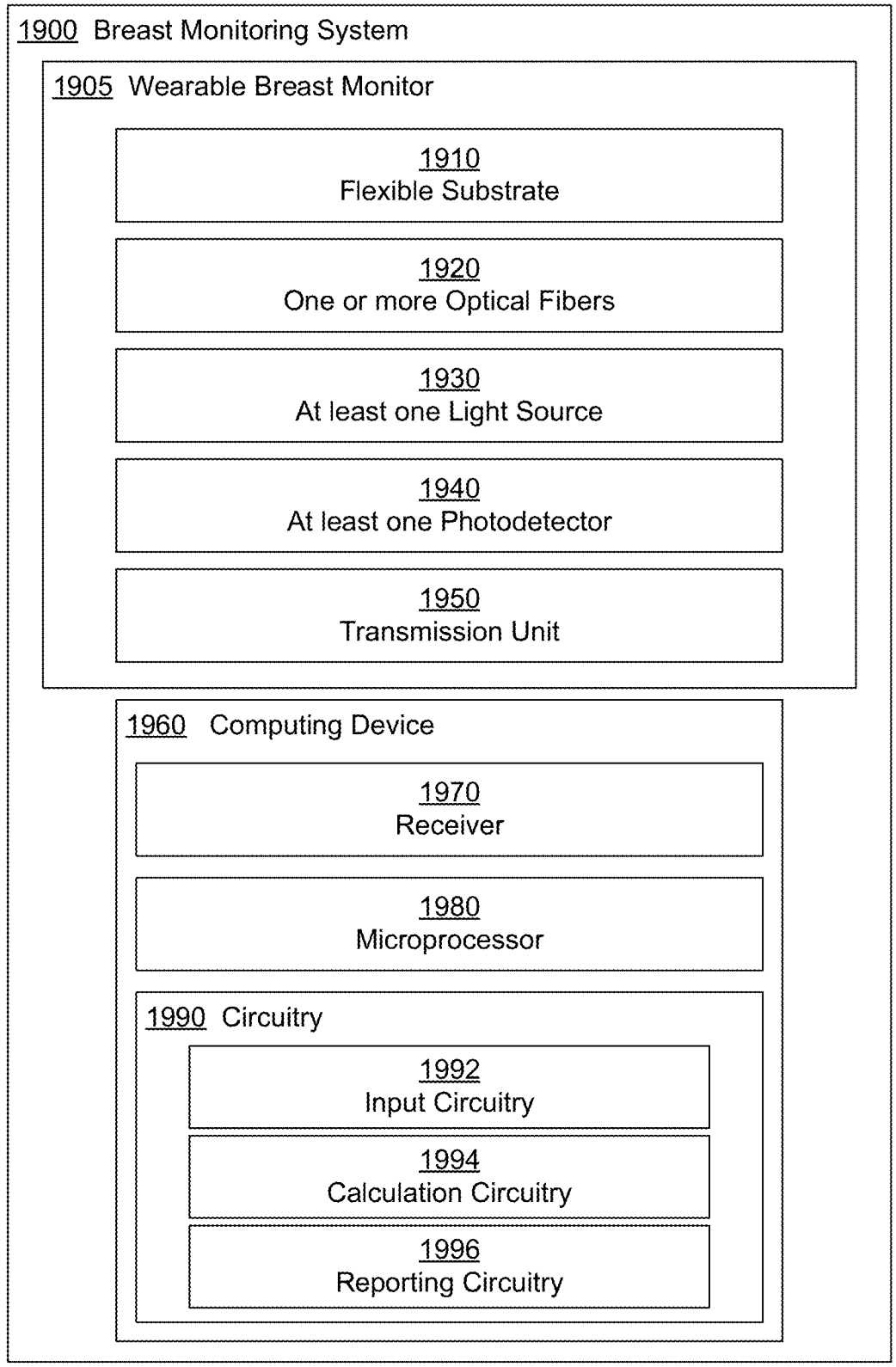
FIG. 19 is a block diagram of an embodiment of breast monitoring system.

FIG. 19 shows non-limiting aspects of a breast monitoring system. Breast monitoring system 1900 includes wearable breast monitor 1905 and computing device 1960. Wearable breast monitor 1905 of system 1900 includes flexible substrate 1910 fabricated to substantially conform to the external contours of at least a portion of one or more breasts of a subject. In an aspect, the flexible substrate 1910 of the wearable breast monitor 1905 is a flexible strip fabricated to substantially conform to the external contours of at least a portion of at least one of the one or more breasts of the subject. In an aspect, the flexible substrate 1910 of the wearable breast monitor 1905 is a flexible sleeve fabricated to substantially conform to the external contours of at least a portion of at least one of the one or more breasts of the subject. In an aspect, the flexible sleeve is sized for placement between the external contours of the at least a portion of at least one of the one or more breasts of the subject and a brassiere (e.g., a nursing bra). In an aspect, the flexible substrate 1910 of the wearable breast monitor 1905 includes an adhesive on at least one surface. In an aspect, the flexible substrate 1910 of the wearable breast monitor 1905 includes a stretchable fabric. In an aspect, the flexible substrate 1910 of the wearable breast monitor 1905 includes a form-fitting material that substantially conforms to the external contours of the at least one portion of the one or more breasts of the subject. Non-limiting aspects of flexible strips, flexible sleeves, and adhesives have been described above herein. In an aspect, at least one surface of the flexible substrate 1910 of the wearable breast monitor 1905 includes a soft fabric. For example, at least one surface of the wearable breast monitor can include a material (e.g., flannel or faux fur) that is soft to the touch and comfortable for the skin surface of a nursing infant.

In an aspect, the flexible substrate 1910 of the wearable breast monitor 1905 is a flexible garment fabricated to substantially conform to the external contours of at least a portion of the one or more breasts of the subject. In an aspect, the flexible garment is a brassiere. In an aspect, the flexible garment is a nursing bra.

In some embodiments, the wearable breast monitor 1905 includes a nipple access portion defined by the flexible substrate 1910, wherein the nipple access portion includes an aperture in the flexible substrate sized to accommodate a nipple associated with the breast of the subject. In an aspect, the wearable breast monitor 1905 includes a nipple access covering sized to cover at least a portion of the nipple access portion of the wearable breast monitor 1905. In an aspect, the nipple access covering is an extension of the flexible substrate sized to cover the nipple access portion and includes at least one fastener configured to reversibly attach the extension of the flexible substrate to the flexible substrate over the nipple access portion. In an aspect, the nipple access covering is a separate piece of material sized to cover the nipple access portion and includes at least one fastener configured to reversibly attach the separate piece of material to the flexible substrate over the nipple access portion. A fastener can include at least one of a snap, a button, a zipper, a hook and loop fastener, VELCRO, magnet, or the like.

Wearable breast monitor 1905 of system 1900 further includes one or more optical fibers 1920 associated with the flexible substrate 1910, wherein the one or more optical fibers 1920 are dynamically bendable. In an aspect, the one or more optical fibers 1920 are at least one of attached to the flexible substrate 1910, incorporated into the flexible substrate 1910, or woven into the flexible substrate 1910 of the wearable breast monitor 1805. In an aspect, the one or more optical fibers are arranged in at least one of a network, radial pattern, spiral pattern, concentric circles, or overlapping patterns on the flexible substrate 1910 of the wearable breast monitor 1905. In some embodiments, at least two of the one or more optical fibers 1920 are proximate and non-parallel. In some embodiments, a first optical fiber overlays a second, non-parallel, optical fiber. In some embodiments, a first portion of at least one of the one or more optical fibers 1920 overlays a second non-parallel portion of the at least one of the one or more optical fibers 1920. In an aspect, the one or more optical fibers 1920 are arranged in a grid-like network on the flexible substrate 1910 of the wearable breast monitor 1905. Non-limiting examples of arrangements or patterns of optical fibers associated with flexible substrates have been described above.

In some embodiments, the flexible substrate 1910 of the wearable breast monitor 1905 includes a first layer and a second layer, wherein the one or more optical fibers 1920 are disposed between the first layer and the second layer of the flexible substrate 1910. In an aspect, the first layer of the flexible substrate and second layer of the flexible substrate are formed from stretchable fabric.

In some embodiments, the one or more optical fibers 1920 associated with the flexible substrate 1910 of the wearable breast monitor 1905 are one or more glass optical fibers. In some embodiments, the one or more optical fibers 1920 associated with the flexible substrate 1910 of the wearable breast monitor 1905 are one or more plastic optical fibers, one or more polymer optical fibers, or one or more acrylic optical fibers. In an aspect, the one or more optical fibers 1920 associated with the flexible substrate 1910 of the wearable breast monitor 1905 are one or more photonic crystal fibers. In an aspect, at least one of the one or more optical fibers 1920 associated with the flexible substrate 1910 of the wearable breast monitor 1905 has a core including one or more fiber Bragg gratings. Non-limiting aspects of optical fibers have been described above herein.

Wearable breast monitor 1905 of breast monitoring system 1900 further includes at least one light source 1930 operably coupled to the one or more optical fibers 1920 and at least one photodetector 1940 positioned to detect light reception from the one or more optical fibers 1920. In an aspect, the at least one light source 1930 of wearable breast monitor 1905 includes a light emitting diode. In an aspect, the at least one light source 1930 of wearable breast monitor 1905 includes a laser diode. In some embodiments, the at least one light source 1930 of the wearable breast monitor 1905 is positioned at a first end of the one or more optical fibers 1920 associated with the flexible substrate 1910 and at least one photodetector 1940 of the wearable breast monitor 1905 is positioned at a second end of the one or more optical fibers 1920 associated with the flexible substrate 1910. In aspect, the at least one photodetector 1940 is positioned along the length of the one or more optical fibers 1920. In an aspect, the at least one photodetector 1940 includes at least one photodiode. In some embodiments, the wearable breast monitor 1905 includes a plurality of photodetectors positioned along a length of at least one of the one or more optical fibers. In some embodiments, the at least one photodetector 1940 is positioned along at least one of the one or more optical fibers 1920 to detect light transmission through the at least one of the one or more optical fibers from the at least one light source 1930. In some embodiments, the at least one photodetector 1940 is positioned along at least one of the one or more optical fibers 1920 to detect light reflected from the at least one of the one or more optical fibers 1920.

In some embodiments, the at least one light source 1930 is configured to emit one or more pulses of light. Under these conditions, the at least one photodetector 1940 is configured to measure a time delta between its reception of light and emission of light by the at least one light source 1930 and the calculation circuitry 1994 is configured to calculate positional information related to the curvature based upon the time delta.

In some embodiments, at least one of the one or more optical fibers 1920 has a cladding component having a first optical absorption coefficient and a core component having a second optical absorption coefficient. In an aspect, at least one first photodetector is configured to detect light reception from the core component and at least one second photodetector is configured to detect light reception from the cladding component; and wherein the calculation circuitry 1994 is configured to calculate positional information related to the curvature based upon a difference between a signal from the at least one first photodetector and a signal from the at least one second photodetector.

Wearable breast monitor 1905 of breast monitoring system 1900 further includes transmission unit 1950 including an antenna and operably coupled to the at least one photodetector 1940, the transmission unit configured to transmit signals, the transmitted signals including light reception information from the at least one photodetector 1940. In an aspect, transmission unit 1950 of the wearable breast monitor 1905 comprises a radiofrequency transmission unit and antenna. For example, the transmission unit can include Bluetooth or WiFi transmission capability. In an aspect, the transmission unit 1950 comprises an optical transmission unit. For example, the transmission unit can include an infrared optical transmitter. Non-limiting aspects of transmission units has been described above herein.

Breast monitoring system 1900 further includes a computing device 1960 including a receiver 1970, a microprocessor 1980, and circuitry 1990. In an aspect, the computing device 1960 is a dedicated handheld device. For example, the computing device can include a dedicated handheld device manufactured specifically for the purpose of working with the wearable breast monitor. Said dedicated handheld device can further include a receiver, a microprocessor, and circuitry including input circuitry, calculation circuitry and reporting circuitry. In an aspect, the computing device 1960 is a mobile communication device. For example, the computing device can include a smart phone, cell phone, or similar device that includes a receiver capable of communicating with the wearable breast monitor and circuitry configured to receive and process information from a wearable breast monitor to calculate changes in breast volume during a breastfeeding event. In an aspect, the computing device 1960 is a laptop or tablet computing device. In some embodiments, the computing device 1960 is connected to a network. For example, the computing device can be connected to or in communication with a network associated with a healthcare provider or lactation consultant. For example, the computing device can be connected to or in communication with a network that allows for sharing breastfeeding information to a website, e.g., a lactation tracking website or to a social media website.

In an aspect, the receiver 1970 is configured to receive transmitted signals from the transmission unit of the wearable breast monitor. In an aspect, the receiver is configured to receive radio, acoustic, electromagnetic, and/or optical transmissions. For example, the receiver can include a radiofrequency receiver for receiving radiofrequency signals from the wearable breast monitor. For example, the receiver can be configured to receive Bluetooth or WiFi transmissions. For example, the receiver can include an optical signal receiver configured to receive an optical transmission, e.g., an infrared transmission.

In an aspect, the computing device 1960 includes a transmission unit (e.g., infrared, Bluetooth or WiFi compatible systems) capable of transmitting signals to the wearable breast monitor 1905. For example, the computing device can included a transmission unit capable of transmitting signals to the wearable breast monitor to control operation of the wearable breast monitor, e.g., on/off signals. For example, the computing device can include a transmission unit capable of transmitting signals from the reporting circuitry back to the wearable breast monitor to activate an associated reporting device, e.g., an optical, audio, or haptic reporting device, associated with the wearable breast monitor to alert a nursing mother and/or infant as to the calculated breast volume delta value.

Circuitry 1990 of computing device 1960 includes input circuitry 1992 configured to receive a first set of transmitted signals from the transmission unit 1950 of the wearable breast monitor 1905, and to receive at least one second set of transmitted signals from the transmission unit 1950 of the wearable breast monitor 1905. Circuitry 1990 includes calculation circuitry 1994 configured to calculate a curvature delta value based on a comparison of the received first set of transmitted signals and the received at least one second set of transmitted signals from the transmission unit 1950 of the wearable breast monitor 1905, and to calculate a breast volume delta value from the calculated curvature delta value. In an aspect, calculation circuitry 1994 of the computing device 1960 includes an algorithm for calculating the breast volume delta value from the calculated curvature delta value. In an aspect, calculation circuitry 1994 of the computing device 1960 includes circuitry configured to calculate a volume of milk expressed during a breastfeeding event from the calculated breast volume delta value. In some embodiments, computing device 1960 includes compilation circuitry configured to compile calculated breast volume delta values over time and transmit a signal including information regarding the compilation to a reporting device.

Circuitry 1990 further includes reporting circuitry 1996 configured to report the calculated breast volume delta value. In an aspect, the reporting circuitry 1996 is configured to report the calculated breast volume delta value to a reporting device associated with the computing device 1960, wherein the reporting device includes at least one of a display, an optical reporting device, an audio reporting device, or a haptic reporting device associated with the computing device 1960. In some embodiments, the reporting circuitry 1996 of the computing device 1960 is configured to report the calculated breast volume delta value to a network. For example, the reporting circuitry can be configured to report the calculated breast volume delta value to a network associated with a healthcare provider and/or lactation consultant. In an aspect, the reporting circuitry 1996 of the computing device 1960 is configured to report the calculated breast volume delta value to a social media website. For example, the reporting circuitry can be configured to report the calculated breast volume delta value to Facebook or similar social media website. Additional non-limiting aspects of input circuitry, calculation circuitry, and reporting circuitry have been described above herein.

In an aspect, the input circuitry 1992, the calculation circuitry 1994, and the reporting circuitry 1996 are part of a breast monitoring application configured for implementation on the computing device. In some embodiments, system 1900 includes a breast monitoring application that includes non-transitory signal bearing medium including one or more instructions, the one or more instructions when implemented on the computing device 1960 include one or more instructions for receiving the first set of transmitted signals from the transmission unit 1950 of the wearable breast monitor 1905; one or more instructions for receiving the at least one second set of transmitted signals from the transmission unit 1950 of wearable breast monitor 1905; one or more instructions for calculating the curvature delta value based on the comparison of the received first set of transmitted signals and the received at least one second set of transmitted signals from the transmission unit 1950 of the wearable breast monitor 1905; one or more instructions for calculating the breast volume delta value from the calculated curvature delta value; and one or more instructions for reporting the calculated breast volume delta value.

A breast monitoring application that includes non-transitory signal bearing medium including one or more instructions, the one or more instructions when implemented on computing device including at least one or more of one or more instructions for transmitting one or more signals having information regarding the calculated breast volume delta value to at least one of a haptic reporting device, an audio reporting device, an optical reporting device, or a transmission unit; one or more instructions for transmitting one or more signals having information regarding the calculated breast volume delta value to a dedicated hand-held device, a mobile communication device, a portable computing device, a computing device, or a network; one or more instructions for compiling calculated breast volume delta values over time and for reporting the compilation; one or more instructions for calculating a volume of milk expressed during a breastfeeding event from the calculated curvature delta value; and one or more instructions for generating a graphic representation of the calculated volume of milk expressed during a first breastfeeding event and at least one second breastfeeding event.

Figure 20:
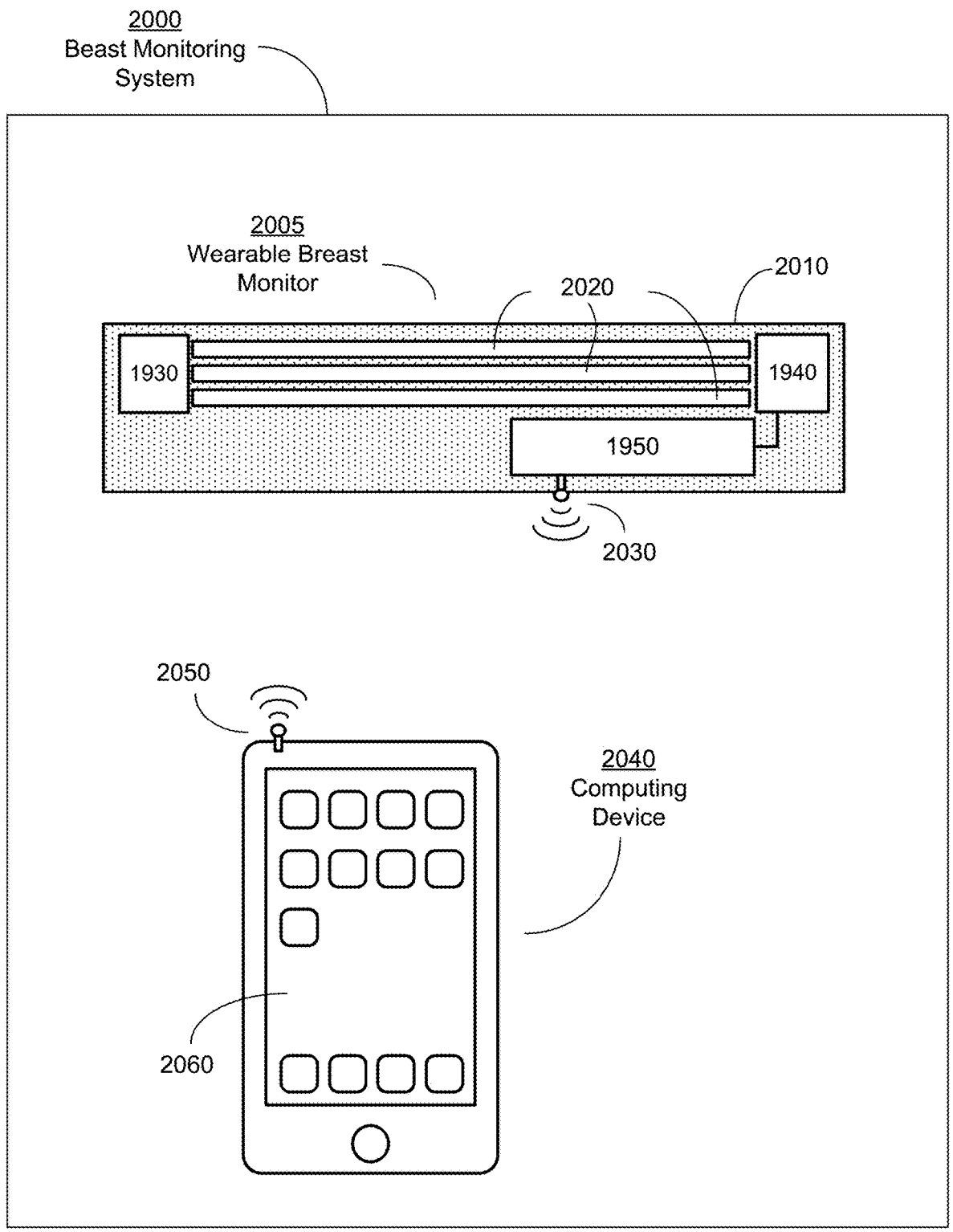
FIG. 20 illustrates an embodiment of a breast monitoring system.

FIG. 20 illustrates a non-limiting example of a breast monitoring system. Breast monitoring system 2000 includes wearable breast monitor 2005 and computing device 2040. Wearable breast monitor 2005 includes a flexible substrate 2010. In this non-limiting example, the substrate is shown as a flexible strip fabricated to substantially conform to the external contours of at least a portion of one or more breasts of a subject. Wearable breast monitor 2005 further includes one or more optical fibers 2020 associated with flexible substrate 2010 as well as at least one light source 1930 operably coupled at one end of optical fibers 2020 and at least one photodetector 1940 positioned to detect light reception at the other end of the optical fibers 2020. The at least one photodetector 1940 is further operably coupled to transmission unit 1950 which includes antenna 2030. Transmission unit 1950 is configured to transmit signals through antenna 2030, the transmitted signals including light reception information from the at least one photodetector 1940. Breast monitoring system 2000 further includes computing device 2040. In this non-limiting example, computing device 2040 is a mobile communication device, e.g., a smart phone. Computing device 2040 includes a receiver 2050 configured to communicate with the transmission unit 1950 of the wearable breast monitor 2005 to receive transmitted signals including light reception information from the at least one photodetector 1940. In some embodiments, transmission unit 1950 of wearable breast monitor 2005 can act as a receiver to receive signals (e.g., operational signals) from computing device 2040 (through, e.g., a transmission feature of receiver 2050). Computing device 2040 includes a microprocessor with circuitry, the circuitry including input circuitry, calculation circuitry, and reporting circuitry. In some embodiments, computing device 2040 includes an application (e.g., a software application) including one or more instructions implemented on the computing device. For example, the computing device, e.g., a smart phone, can include a downloadable application for use in calculating changes in breast volume during a breastfeeding event based on the signals received from the wearable breast monitor. Computing device further includes display 2060. Display 2060 can be operably coupled to reporting circuitry configured to report a calculated breast volume delta value to a user, e.g., the subject using the breast monitoring system during a breastfeeding event or a healthcare provider or lactation consultant monitoring said breastfeeding events. For example, the display can display a numerical representation of the calculated breast volume delta value. For example, the display can display a graphical representation of the calculated breast volume delta value. In some embodiments, the reporting circuitry can be configured to report the calculated breast volume delta value audibly to the user. For example, the computing device can include a sound card for transmitting an audible signal, e.g., beeps or spoken language, indicative of the calculated breast volume delta value. In some embodiments, the reporting circuitry can be configured to report the calculated breast volume delta value haptically to the user. For example, the computing device can include a vibrating component for transmitting a haptic signal, e.g., a vibration, to the subject indicative of the calculated breast volume delta value. In some embodiments, the optical, audible, and/or haptic signal is intended to startle a nursing infant such that he/she disengages from the nipple of the nursing mother when sufficient milk for any given breastfeeding event has been expressed.

Figure 21:
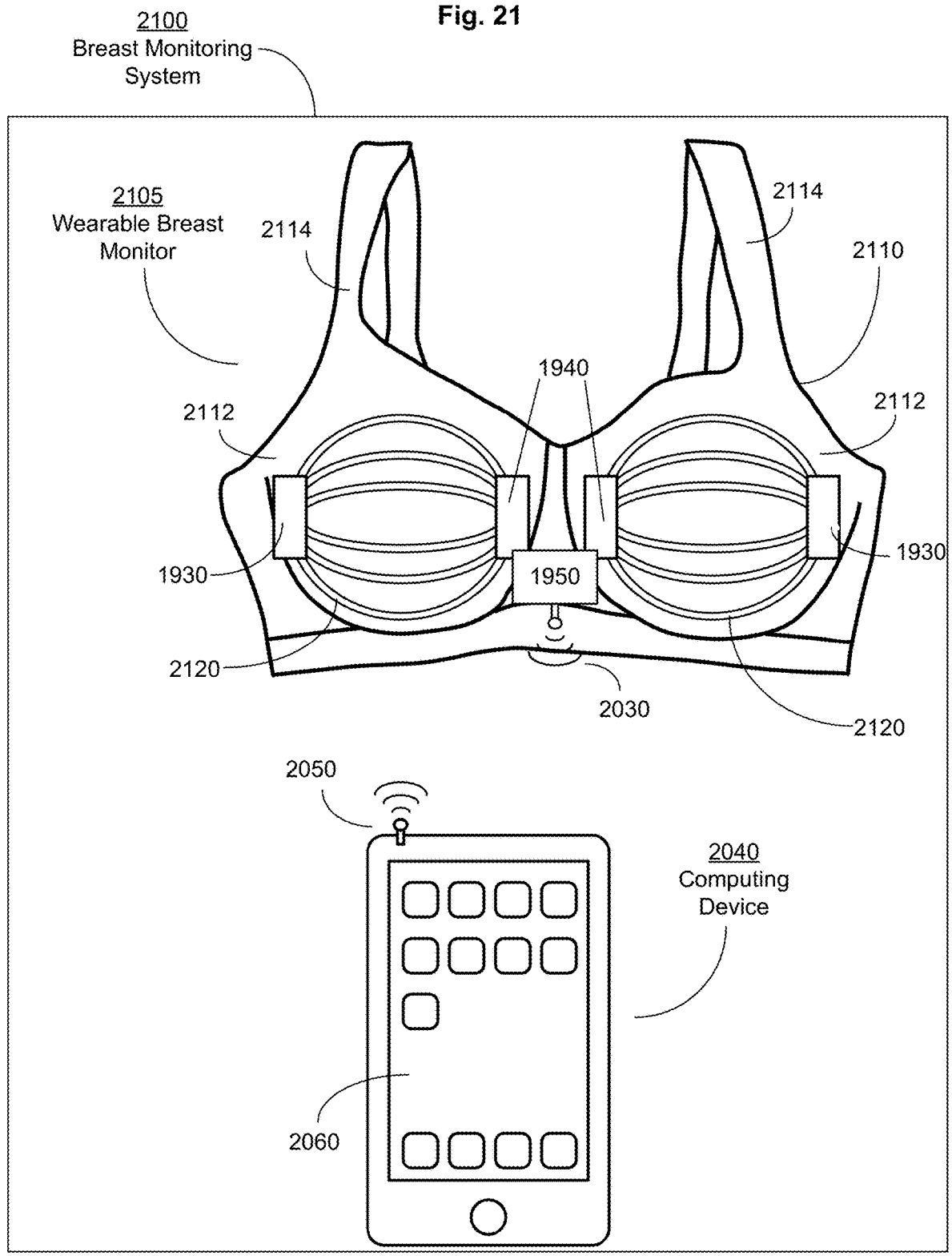
FIG. 21 illustrates an embodiment of a breast monitoring system.

FIG. 21 illustrates a non-limiting example of a breast monitoring system. Breast monitoring system 2100 includes wearable breast monitor 2105 and computing device 2040. Wearable breast monitor 2105 includes a flexible substrate 2110. In this non-limiting example, flexible substrate 2110 takes the form of a typical brassiere including cups 2112 intended to fit snuggly around each of the breasts and straps 2114 intended to support the breasts in cups 2112. In some embodiments, the flexible substrate can include a dedicated nursing bra. Wearable breast monitor 2105 further includes optical fibers 2120 arranged in a pattern on or in the cups 2112 of flexible substrate 2110. In this non-limiting example, the optical fibers 2120 span from the medial side to the lateral side of cups 2112. Also in this non-limiting example, at least one light source 1930 is positioned on the lateral side of each cup 2112 while at least one photodetector 1940 is position on the medial side of each cup 2112. Light source 1930 is operably coupled to a first end of optical fibers 2120 and at least one photodetector 1940 is operably coupled to a second end of optical fibers 2120. In some embodiments, at least one photodetector 1940 is positioned along the length of optical fibers 2120. The at least one photodetector 1940 is further operably coupled to transmission unit 1950 which includes antenna 2030. Transmission unit 1950 is configured to transmit signals through antenna 2030, the transmitted signals including light reception information from the at least one photodetector 1940.

In an aspect, wearable breast monitor 2105 is incorporated into a nursing bra. In some embodiments, a wearable breast monitor includes a nipple access portion defined by the flexible substrate, wherein the nipple access portion includes an aperture sized to accommodate a nipple associated with the breast. In an aspect, the wearable breast monitor further includes a nipple access covering, wherein the nipple access covering is sized to cover at least a portion of the nipple access portion. In some embodiments, the nipple access covering is an extension of the flexible substrate sized to cover the nipple access portion and includes at least one fastener configured to reversibly attach the extension of the flexible substrate to the flexible substrate over the nipple access portion. In some embodiments, the nipple access covering is a separate piece of material sized to cover the nipple access portion and includes at least one fastener configured to reversibly attach the separate piece of material to the flexible substrate over the nipple access portion. For example, the nipple access covering can be formed from the same material as the flexible substrate. For example, the nipple access covering can be formed from a material that is different from the flexible substrate. In an aspect, the fastener includes at least one of a snap, a button, a zipper, a hook and loop fastener, VELCRO, or an adhesive. In an aspect, the nipple access covering is held on and/or over the nipple access portion by virtue of friction with the flexible substrate material.

Breast monitoring system 2100 further includes computing device 2040. In this non-limiting example, computing device 2040 is a mobile communication device, e.g., a smart phone. Computing device 2040 includes a receiver 2050 configured to communicate with the transmission unit 1950 of the wearable breast monitor 2005 to receive transmitted signals including light reception information from the at least one photodetector 1940. Computing device 2040 includes a microprocessor with circuitry, the circuitry including input circuitry, calculation circuitry, and reporting circuitry. In some embodiments, computing device 2040 includes an application including one or more instructions implemented on the computing device. For example, the computing device, e.g., a smart phone, can include a downloadable application for use in calculating changes in breast volume during a breastfeeding event based on the signals received from the wearable breast monitor. Computing device further includes display 2060. Display 2060 can be operably coupled to reporting circuitry configured to report a calculated breast volume delta value to a user. For example, the display can display a numerical representation and/or a graphical representation of the calculated breast volume delta value. In some embodiments, the reporting circuitry can be configured to report the calculated breast volume delta value audibly (e.g., through beeps or spoken language) or haptically (e.g., through a vibration) to the user.

FIG. 22 shows a block diagram of a method for monitoring a breastfeeding event. Method 2200 includes in block 2210 receiving a first set of signals at a first time point from at least one photodetector positioned to detect light reception from one or more optical fibers associated with a flexible substrate of a wearable breast monitor. Method 2200 includes in block 2220 receiving at least one second set of signals at at least one second time point from the at least one photodetector positioned to detect light reception from the one or more optical fibers associated with the flexible substrate of the wearable breast monitor. Method 2200 includes in block 2230 calculating a curvature delta value based on comparing the received first set of signals and the received at least one second set of signals. Method 2200 includes in block 2240 calculating a breast volume delta value from the calculated curvature delta value. Method 2200 includes in block 2250 transmitting one or more signals having information regarding the calculated breast volume delta value to a reporting device.

Method 2200 includes receiving a first set of signals and at least one second set of signals from at least one photodetector. In some embodiments, the method includes receiving the first set of signals and the at least one second set of signals directly from the at least one photodetector. For example, the method can include a microcontroller associated with the wearable breast monitor directly receiving signals from photodetectors associated with the wearable breast monitor. In some embodiments, the method includes receiving the first set of signals and the at least one second set of signals indirectly from the at least one photodetector. For example, the method includes a computing device wirelessly receiving signals from a transmission unit operably coupled to the at least one photodetector of the wearable breast monitor.

Method 2200 includes calculating a curvature data value based on comparing the received first set of signals and the at least one second set of signals from the at least one photodetector. In some embodiments, the method includes accessing a database, look-up table, graph, or reference source including information regarding optical output for a given optical fiber type or configuration depending upon curvature of the optical fiber.

Method 2200 includes calculating a breast volume delta value from the calculated curvature delta value. The method can include using an algorithm to calculate the breast volume delta value. Non-limiting examples of algorithms from calculated breast volume have been described above herein.

Method 2200 includes transmitting one or more signals having information regarding the calculated breast volume delta value to a reporting device. For example, the method can include transmitting one or more signals having information regarding the calculated breast volume delta value to a reporting device associated with the wearable breast monitor. For example, the method can include transmitting the one or more signals having information regarding the calculated breast volume delta value to a reporting device associated with a computing device, e.g., a dedicated handheld device, a mobile communication device, or a laptop or tablet computer.

In some embodiments, the method includes transmitting the one or more signals having the information regarding the calculated breast volume delta value to at least one of a haptic reporting device, an audio reporting device, or an optical reporting device. In an aspect, the haptic reporting device, audio reporting device, or optical reporting device is incorporated into the wearable breast monitor. In an aspect, the haptic reporting device, audio reporting device, or optical reporting device is incorporated into a separate computing device, e.g., a dedicated handheld device, a mobile communication device, or a laptop or tablet computer.

In an aspect, the method includes transmitting the one or more signals having the information regarding the calculated breast volume delta value to a transmission unit including an antenna. In an aspect, the method includes transmitting the one or more signals having the information regarding the calculated breast volume delta value through the transmission unit to an external device. For example, the method can include transmitting one or more signals having information regarding the calculated breast volume delta value from a transmission unit associated with a wearable breast monitor to an external device, e.g., a computing device. In an aspect, the method includes transmitting the one or more signals having the information regarding the calculated breast volume delta value through the transmission unit to at least one of a dedicated hand-held device, a mobile communication device, a portable computing device, a computing device, or a network. For example, the method can include transmitting one or more signals having information regarding the calculated breast volume delta value from a transmission unit associated with a wearable breast monitor to an external device, e.g., a dedicated handheld device, a mobile communication device, or a laptop or tablet computer.

In an aspect, the method further includes calculating a volume of milk expressed during a breastfeeding event from the calculated curvature delta value; and transmitting one or more signals having information regarding the calculated volume of expressed milk to an external device. In an aspect, the method further includes tracking the calculated volume of milk expressed during a first breastfeeding event and at least one second breastfeeding event. For example, the method can include storing data including the calculated volume of milk expressed at a first breastfeeding event and at least one second breastfeeding event. In an aspect, the method further includes generating a graphic representation of the calculated volume of milk expressed during a first breastfeeding event and at least one second breastfeeding event. For example, the method can include generating a graph or chart including a date and/or time for each breastfeeding event and a calculated volume of milk expressed at each of the breastfeeding events. The graphical representation or chart can include a histogram, a bar chart, a pie chart, and/or a line chart. Alternatively or in addition, the graphical representation or chart can include a timeline chart. In some embodiments, the method can include generating a graph or chart including three variables. For example, the method can include generating a bubble chart or 3-D chart including a date correlated with an infant's age, volume of milk expressed, and a plurality of infants. In an aspect, the method includes generating a plot to track the calculated volume of milk expressed. For example, the method can include generating a box plot, dot plot, scatterplot, or the like. The graphical representation of the calculated volume of milk over time can be displayed on a display associated with a dedicated handheld device, a mobile communication device, a laptop or tablet computing device, or other computing device. In an aspect, the graphical representation is provided to the user, i.e., the nursing mother. In an aspect, the graphical representation is provided to a medical practitioner or lactation specialist.

A method is described for using a wearable breast monitor to measure changes in breast volume during a breastfeeding event. FIG. 23 shows a block diagram of a method for monitoring breastfeeding. Method 2300 includes in block 2310 measuring curvature of a breast during a breastfeeding event at a first time point and at at least one second time point with one or more optical fibers associated with a flexible substrate of a wearable breast monitor. Method 2300 includes in block 2320 calculating a change in curvature of the breast during the breastfeeding event between the first time point and the at least one second time point. Method 2300 includes in block 2330 correlating the calculated change in curvature of the breast during the breastfeeding event with a volume of milk expressed between the first time point and the at least one second time point. Method 2300 includes in block 2340 reporting the volume of milk expressed during the breastfeeding event between the first time point and the at least one second time point to a user. Methods including algorithms for calculating the change in volume of the breast based on the changes in curvature of the breast have been described above herein.

The method for monitoring breastfeeding includes measuring the curvature of the breast during a breastfeeding event at a first time point and at at least one second time point with the one or more optical fibers associated with the flexible substrate of the wearable breast monitor. In some embodiments, the method can include measuring the curvature of the breast at a time point prior to initiating a breastfeeding event and at a second time at the end of a breastfeeding event. In an aspect, the wearable breast monitor is worn throughout the breastfeeding event. In an aspect, the wearable breast monitor is applied prior to initiation of the breastfeeding event to measure curvature of the breast at the first time point, removed for the actual breastfeeding event, and reapplied after the end of the breastfeeding event to measure curvature of the breast at the second time point.

In some embodiments, the method can include wearing the wearable breast monitor throughout a breastfeeding event so as to measure the curvature of the breast at several time points before, during, and/or after the course of the breastfeeding event. For example, the method can include continuously measuring changes in curvature during a breastfeeding event and reporting the resulting changes in breast volume on a continuous basis.

The method further includes calculating a change in curvature of the breast during the breastfeeding event between the first time point and the at least one second time point. In an aspect, the method includes receiving a first set of signals from at least one photodetector positioned to detect light reception from the one or more optical fibers associated with the flexible substrate of the wearable breast monitor and receiving at least one second set of signals from the at least one photodetector. For example, the method can include calculating the change in curvature of the breast from the first time point and the at least one second time point based on changes in voltage received from the photodetector of the wearable breast monitor. The method further includes correlating the calculated change in curvature of the breast during the breastfeeding event with a volume of milk expressed between the first time point and the at least one second time point.

The method includes reporting the calculated volume of milk expressed during the breastfeeding event. The method can include reporting the calculated volume of milk expressed to a user through at least one of an optical reporting device, a haptic reporting device, or an audio reporting device. The method can include reporting the calculated volume of milk expressed to a user through a display as part of a numerical and/or graphical representation. The method can include reporting the calculated volume of milk expressed to the user on a dedicated handheld device, a mobile communication device, a portable computing device, or other similar computing device. The method can include reporting the calculated volume of milk expressed to the user through a network interface.

In an aspect, the method further includes tracking the calculated volume of milk expressed during a first breastfeeding event and at least one second breastfeeding event. For example, the method can include storing data including the calculated volume of milk expressed at a first breastfeeding event and at least one second breastfeeding event. In an aspect, the method further includes generating a graphic representation of the calculated volume of milk expressed during a first breastfeeding event and at least one second breastfeeding event. For example, the method can include generating a graph or chart including a date and/or time for each breastfeeding event and a calculated volume of milk expressed at each of the breastfeeding events. The graphical representation or chart can include a histogram, a bar chart, a pie chart, and/or a line chart. Alternatively or in addition, the graphical representation or chart can include a timeline chart. In some embodiments, the method can include generating a graph or chart including three variables. For example, the method can include generating a bubble chart or 3-D chart including a date correlated with an infant's age, volume of milk expressed, and a plurality of infants. In an aspect, the method includes generating a plot tracking the calculated volume of milk expressed. For example, the method can include generating a box plot, dot plot, scatterplot, or the like. The graphical representation of the calculated volume of milk over time can be displayed on a display associated with a dedicated handheld device, a mobile communication device, a laptop or tablet computing device, or other computing device. In an aspect, the graphical representation is provided to the user, i.e., the nursing mother. In an aspect, the graphical representation is provided to a medical practitioner or lactation specialist.

Described herein are aspects of a breast sensor device. In some embodiments, a breast sensor device includes a flexible substrate fabricated to substantially conform to external contours of at least a portion of one or more breasts of a subject; one or more optical fibers associated with the flexible substrate, wherein the one or more optical fibers are dynamically bendable; and at least one connector operably coupled to the one or more optical fibers. The at least one connector is configured to connect the breast sensor device to at least one light source and at least one photodetector.

Figure 24:
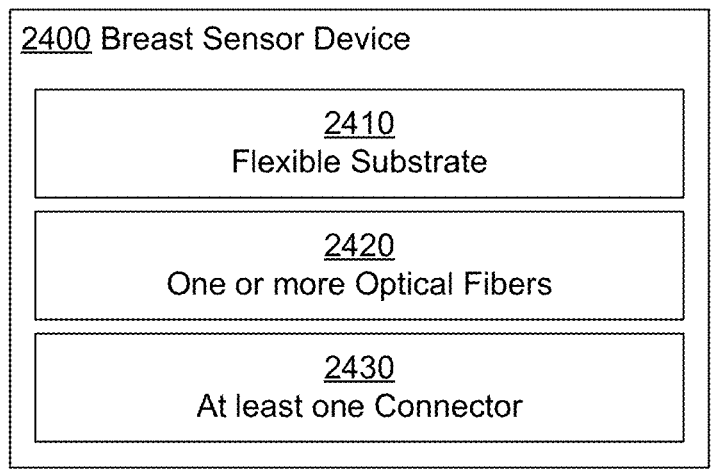
FIG. 24 shows a block diagram of an embodiment of a breast sensor device.
Figure 25:
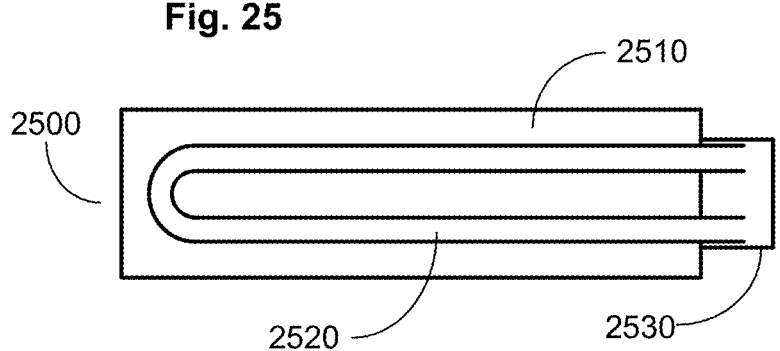
FIG. 25 illustrates an embodiment of a breast sensor device.
Figure 26:
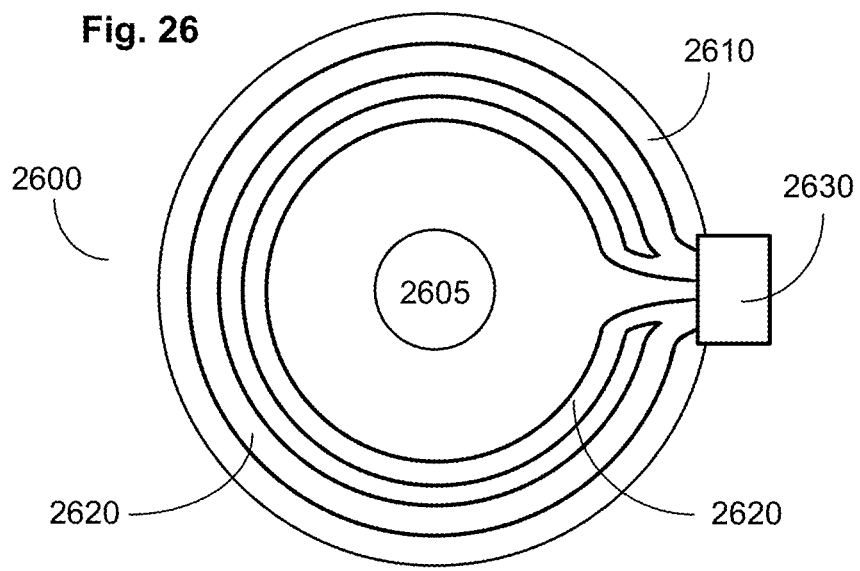
FIG. 26 illustrates an embodiment of a breast sensor device.

FIGS. 24-26 illustrate non-limiting aspects of breast sensor devices. FIG. 24 shows a block diagram of breast sensor device 2400 including flexible substrate 2410, one or more optical fibers 2420, and at least one connector 2430.

In an aspect, the flexible substrate 2410 is a flexible strip fabricated to substantially conform to the external contours of the at least a portion of the one or more breasts of the subject. In an aspect, the flexible substrate 2410 is a flexible sleeve fabricated to substantially conform to the external contours of the at least a portion of the one or more breasts of the subject. In some embodiments, the flexible sleeve is sized for placement between the external contours of the at least a portion of the one or more breasts of the subject and a garment. In some embodiments, the garment includes a nursing bra. Alternatively, the garment includes a brassiere, sports bra, or other tight or form-fitting undergarment. In an aspect, the flexible substrate 2410 includes a stretchable fabric. In an aspect, the flexible substrate 2410 includes a form-fitting material that substantially conforms to the external contours of the at least a portion of the one or more breasts of the subject. For example, the stretchable and/or form-fitting fabric can include a stretchable polyester fabric (e.g., LYCRA).

In an aspect, the breast sensor device 2400 includes an adhesive on at least one surface of the flexible substrate 2410. For example, at least one surface of the flexible substrate of the breast sensor device can include a biocompatible and reversible adhesive (e.g., a pressure sensitive adhesive) for adhering the breast sensor device to the skin surface of a subject. For example, at least one surface of the flexible substrate of the breast sensor device can include an adhesive for adhering the breast sensor device to a surface of a brassiere (e.g., a nursing bra).

In an aspect, the breast sensor device 2400 includes at least one fastener configured to attach the breast sensor device 2400 to a garment. In an aspect, the fastener is at least one of a snap, a button, a zipper, a hook and eye fastener, a hook and loop fastener, a magnetic fastener, or an adhesive. In an aspect, the at least one fastener is configured to attach the breast sensor device 2400 to a nursing bra. For example, the breast sensor device can include a hook and loop fastener (e.g., VELCRO) for attaching the breast sensor device into a cup region of a nursing bra.

Breast sensor device 2400 includes one or more optical fibers 2420 associated with the flexible substrate 2410. In an aspect, the one or more optical fibers 2420 are one or more glass optical fibers. In an aspect, the one or more optical fibers 2420 are one or more plastic optical fibers. In an aspect, the one or more optical fibers 2420 are one or more polymer optical fibers. In an aspect, the one or more optical fibers 2420 are one or more photonic crystal fibers. In an aspect, the one or more optical fibers 2420 are one or more acrylic optical fibers. In an aspect, each of the one or more optical fibers 2420 includes an inner core and an outer cladding, and wherein a portion of a core/cladding interface is modified to alter light transmission, wherein the amount of light transmitted out is dependent on the curvature of the one or more optical fibers 2420. In an aspect, one or more portions along the length of the one or more optical fibers 2420 are rendered transmissive to light, and the amount of light transmitted out is dependent on the curvature of the one or more optical fibers 2420. In an aspect, at least one of the one or more optical fibers 2420 includes one or more fiber Bragg gratings.

One or more optical fibers 2420 are associated with the flexible substrate 2410 of breast sensor device 2400. In an aspect, the one or more optical fibers 2420 are attached to the flexible substrate 2410. In an aspect, the one or more optical fibers 2420 are incorporated into the flexible substrate 2410. In an aspect, the one or more optical fibers 2420 are woven into the flexible substrate 2410.

In some embodiments, the flexible substrate 2410 includes a first layer and a second layer, and the one or more optical fibers 2420 are disposed between the first layer and the second layer of the flexible substrate. In an aspect, the first layer and the second layer of the flexible substrate 2410 are formed from a stretchable fabric. For example, the first and second layers of the flexible substrate can include a stretchable polyester fabric between which the one or more optical fibers are disposed. In some embodiments, at least one of the first layer or the second layer of the flexible substrate includes a soft fabric. For example, the first layer and/or the second layer of the flexible substrate can include a soft flannel or other fabric intended to be soft to the touch, and particularly soft to the touch of an infant's cheek while breastfeeding.

The one or more optical fibers 2420 are arranged in a pattern on a surface of the flexible substrate 2410 of breast sensor device 2400. In an aspect, the one or more optical fibers 2420 associated with the flexible substrate 2410 are arranged in a network. In an aspect, the one or more optical fibers 2420 associated with the flexible substrate 2410 are arranged in a radial pattern. In an aspect, the one or more optical fibers 2420 associated with the flexible substrate 2410 are arranged in a spiral pattern. In an aspect, the one or more optical fibers 2420 associated with the flexible substrate 2410 are arranged in concentric circles. In an aspect, the one or more optical fibers 2420 associated with the flexible substrate 2410 are arranged in overlapping patterns. In an aspect, the one or more optical fibers 2420 associated with the flexible substrate 2410 are proximate and non-parallel. In some embodiments, a first optical fiber overlays a second, non-parallel optical fiber. In some embodiments, a first portion of at least one of the one or more optical fibers 2420 overlays a second non-parallel portion of the at least one of the one or more optical fibers. In an aspect, the one or more optical fibers 2420 associated with the flexible substrate 2410 are arranged in a grid-like network.

Breast sensor device 2400 includes at least one connector 2430 operably coupled to the one or more optical fibers 2420. For example, a breast sensor device can include a plug operably coupled to the optical fibers and configured to connect the breast sensor device to at least one of a light source and/or a photodetector. For example, a breast sensor device can include a conduit operably coupled to the optical fibers and configured to connect the breast sensor device to at least one of a light source and/or a photodetector. The connector can include a connector, a plug, a conduit, an adapter, a coupling, a joint, or a linker operably coupled to the one or more optical fibers and configured to operably connect one or more optical fibers of the breast sensor device to at least one of a light source and/or a photodetector. In an aspect, the at least one connector 2430 includes a light input connector configured to operably connect the one or more optical fibers 2420 to a light source. In an aspect, the at least one connector 2430 includes a light output connector configured to operably connect the one or more optical fibers 2420 to a photodetector. In some embodiments, the at least one connector 2430 of the breast sensor device 2400 includes at least one light input connector and at least one light output connector. In some embodiments, the at least one connector 2430 includes a light input connector configured to operably connect a first end of the one or more optical fibers 2420 to a light source and a light output connector configured to operably connect a second end of the one or more optical fibers 2420 to a photodetector.

FIG. 25 shows a non-limiting embodiment of a breast sensor device. Breast sensor device 2500 includes a flexible substrate 2510. In this non-limiting example, flexible substrate 2510 is a flexible strip fabricated to substantially conform to the external contours of at least a portion of the one or more breasts of the subject. For example, a flexible strip including one or more optical fibers and a connector can be adhered to a surface of a subject's breast to monitor changes in breast curvature and breast volume during a breastfeeding event. Breast sensor 2500 includes optical fiber 2520 associated with flexible substrate 2510 (e.g., a flexible strip). In this non-limiting exampling, the optical fiber is curved such that a first end and a second end of the fiber are proximate to one another. Breast sensor 2500 further includes connector 2530. In this non-limiting example, connector 2530 is configured to connect the first end of the optical fiber 2520 to a light source and the second end of the optical fiber 2530 to a photodetector.

In some embodiments, the breast sensor device includes a nipple access portion defined by the flexible substrate, wherein the nipple access portion includes an aperture in the flexible substrate sized to accommodate a nipple associated with the breast of the subject. FIG. 26 shows a non-limiting example of a breast sensor device including a nipple access portion. Breast sensor device 2600 includes a flexible substrate 2610. In this non-limiting example, flexible substrate 2610 is a flexible sleeve fabricated to substantially conform to the external contours of at least a portion of at least one of the one or more breasts of the subject. Breast sensor device 2600 further includes nipple access portion 2605 defined by flexible substrate 2610, wherein nipple access portion 2605 includes an aperture in the flexible substrate 2610 sized to accommodate a nipple associated with the breast of the subject. Breast sensor device further includes one or more optical fibers 2620. In this non-limiting example, the one or more optical fibers 2620 are associated with the flexible substrate 2610 in concentric circles. The ends of the optical fibers meet at the connector 2630. Connector 2630 is configured to connect a first end of the one or more optical fibers 2620 to a light source and a second end of the one or more optical fibers 2620 to a photodetector.

In some embodiments, a breast sensor device is part of a breast monitoring system. In some embodiments, a breast monitoring system includes a breast sensor device including a flexible substrate fabricated to substantially conform to external contours of at least a portion of one or more breasts of a subject, one or more optical fibers associated with the flexible substrate, wherein the one or more optical fibers are dynamically bendable, and at least one connector operably coupled to the one or more optical fibers; at least one light source configured to operably couple with a first end of the one or more optical fibers of the breast sensor device through the at least one connector; at least one photodetector configured to operably couple with a second end of the one or more optical fibers of the breast sensor device through the at least one connector, the at least one photodetector positioned to detect light transmission through at least one of the one or more optical fibers from the at least one light source; a reporting device; and a microcontroller including a microprocessor and circuitry, wherein the circuitry includes input circuitry configured to receive a first set of signals from the at least one photodetector, and receive at least one second set of signals from the at least one photodetector; calculation circuitry configured to calculate a curvature delta value based on a comparison of the received first set of signals and the received at least one second set of signals from the at least one photodetector, and calculate a breast volume delta value from the calculated curvature delta value; and reporting circuitry configured to transmit a signal to the reporting device based on the calculated breast volume delta value.

Figure 27:
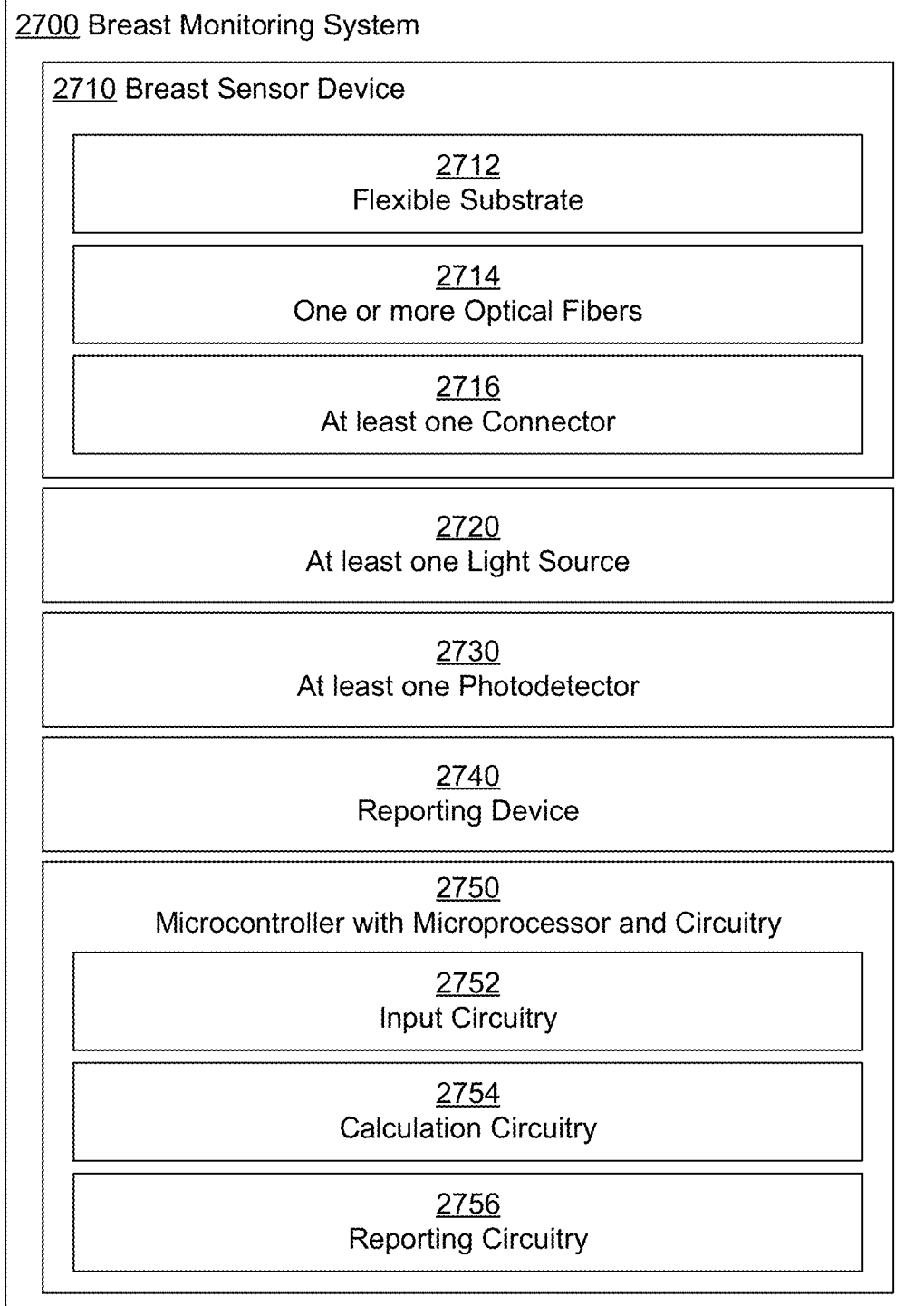
FIG. 27 shows a block diagram of an embodiment of a breast monitoring system including a breast sensor device.

FIG. 27 shows a block diagram illustrating non-limiting aspects of a breast monitoring system. Breast monitoring system 2700 includes breast sensor device 2710 including flexible substrate 2712, one or more optical fibers 2714, and at least one connector 2716. Non-limiting aspects of a breast sensor device including at least one connector have been described above herein in FIGS. 24-26 and associated text. System 2700 further includes at least one light source 2720, at least one photodetector 2730, reporting device 2740, and microcontroller 2750 including a microprocessor and circuitry. The circuitry includes input circuitry 2752, calculation circuitry 2754, and reporting circuitry 2756.

System 2700 includes at least one light source 2720 configured to operably couple with a first end of the one or more optical fibers 2714 of the breast sensor device 2710 through the at least one connector 2716. In an aspect, the at least one light source 2720 includes at least one light emitting diode. In an aspect, the at least one light source 2720 includes at least one laser diode.

System 2700 further includes at least one photodetector 2730 configured to operably couple with a second end of the one or more optical fibers 2714 of the breast sensor device 2710 through the at least one connector 2716, the at least one photodetector 2730 positioned to detect light transmission through at least one of the one or more optical fibers from the at least one light source. In some embodiments, the at least one photodetector 2730 is positioned to detect light transmission through at least one of the one or more optical fibers 2714 from the at least one light source 2720. In some embodiments, the at least one photodetector 2730 is positioned to detect light reflection from at least one of the one or more optical fibers 2714. In an aspect, the at least one photodetector includes at least one photodiode. Non-limiting aspects of photodetectors have been described above herein.

In some embodiments, at least one of the one or more optical fibers 2714 of the breast sensor device 2710 has a cladding component having a first optical absorption coefficient and a core component having a second optical absorption coefficient. In an aspect, at least one first photodetector is configured to detect light reception form the core component and at least one second photodetector is configured to detect light reception from the cladding component; and wherein the calculation circuitry is configured to calculate positional information related to the curvature based upon a difference between signals from the at least one first photodetector and signals from the at least one second photodetector.

In some embodiments, the at least one light source 2720 is configured to emit one or more pulses of light. The at least one photodetector 2730 is further configured to measure a time delta between its reception of light and emission of light by the at least one light source 2720. The calculation circuitry 2754 is configured to calculate positional information related to the curvature based upon the time delta.

In some embodiments, the one or more optical fibers 2714 of the breast sensor device are photonic crystal fibers; and wherein the calculation circuitry 2754 is configured to calculate the curvature delta value based upon a difference in optical modal structure associated with a first set of signals and a second set of signals.

Breast monitoring system 2700 further includes reporting device 2740. The reporting device is configured to report information regarding the calculated breast volume delta. In some embodiments, the reporting device provides a signal, e.g., a flashing light, an audible beep, or a haptic vibration, indicating that the calculated breast volume delta represents a sufficient amount of milk expressed during a given breastfeeding event. Alternatively, the reporting device provides more specificity in the form of text, graphics, or words indicating that the calculated breast volume delta represents a sufficient amount of milk expressed during the breastfeeding event.

In some embodiments, the reporting device 2740 includes a haptic reporting device. For example, the reporting device can include a vibrational device configured to provide haptic information to a user (e.g., the nursing mother) before, during, and/or after a breastfeeding event. In some embodiments, the reporting device 2740 includes an audio reporting device. For example, the reporting device can include an audio speaker and sound card configured to provide audio information to a user (e.g., the nursing mother, a healthcare provider, and/or a lactation consultant) before, during, and/or after a breastfeeding event. In some embodiments, the reporting device 2740 includes an optical reporting device. For example, the reporting device can include one or more lights configured to provide visual information to a user (e.g., the nursing mother, a healthcare provider, and/or a lactation consultant) before, during, and/or after a breastfeeding event. For example, the reporting device can include a display, e.g., an LCD display, configured to provided information in the form of text, tables, and/or graphs to a user before, during, and/or after a breastfeeding event.

In some embodiments, the reporting device includes a transmission unit including an antenna, the transmission unit configured to transmit the information regarding the calculated breast volume delta value to an external device. In an aspect, the transmission unit includes a radiofrequency transmission unit. For example, the transmission unit may be part of a Bluetooth system. In an aspect, the transmission unit includes an optical transmission unit. In an aspect, the transmission unit is configured to transmit the information regarding the calculated breast volume delta value to a dedicated handheld device. In an aspect, the transmission unit is configured to transmit the information regarding the calculated breast volume delta value to a mobile communication device. For example, the transmission unit can transmit the calculated breast volume delta value to a user's cell phone or smart phone. In an aspect, the transmission unit is configured to transmit the information regarding the calculated breast volume delta value to a computing device. For example, the transmission unit can transmit the calculated breast volume delta value to a lap top or tablet computing device. In some embodiments, computing device is associated with the nursing subject. Alternatively or in addition, the computing device is associated with a health care provider and/or lactation consultant. In some embodiments, the transmission unit is configured to transmit the information regarding the calculated breast volume delta value to a network. For example, the transmission unit can be configured to send the calculated breast volume delta value to an Internet site, e.g., a social media or healthcare provider site. In an aspect, the transmission unit is configured to transmit the calculated breast volume delta value to an Internet site specifically set up to collect and track said data over time.

The breast monitoring system 2700 further includes a microcontroller 2750 including a microprocessor and circuitry. In some embodiments, the microcontroller 2750 is configured to receive information from the at least one photodetector 2730 through a wired connection. In some embodiments, the microcontroller 2750 is configured to receive information from the at least one photodetector 2730 through a wireless connection. In some embodiments, the reporting device 2740 is a transmission unit configured to wirelessly transmit information from the at least one photodetector 2730 to the microcontroller 2730. In some embodiments, the microcontroller 2750 is incorporated into a garment, e.g., a nursing bra along with the at least one light source, the reporting device, and the at least one photodetector. In some embodiments, the microcontroller is associated with a dedicated hand-held device. For example, the microcontroller can include a dedicated hand-held device in with at least one photodetector associated with a nursing bra through a transmission unit. Alternatively, the microcontroller is associated with a mobile communication device, e.g., a cell phone or smart phone. In an aspect, the microcontroller is associated with a computing device, e.g., a laptop or tablet computing device.

Microcontroller 2750 includes circuitry configured to receive, process, and report data. The circuitry includes input circuitry 2752 configured to receive a first set of signals from the at least one photodetector 2730; and receive at least one second set of signals from the at least one photodetector 2730. The circuitry includes calculation circuitry 2754 configured to calculate a curvature delta value based on a comparison of the received first set of signals and the received at least one second set of signals from the at least one photodetector 2730. In some embodiments, the calculation circuitry 2754 of the microcontroller 2750 includes an algorithm for calculating the breast volume delta value from the calculated curvature delta value. Non-limiting aspects of algorithms for use in calculating the breast volume delta based on changes in breast curvature during a breastfeeding event have been described above. In an aspect, the calculation circuitry 2754 of the microcontroller is configured to calculate a volume of milk expressed during a breastfeeding event from the calculated breast volume delta value.

The microcontroller 2750 further includes reporting circuitry 2756 configured to transmit a signal to the reporting device 2740 based on the calculated breast volume delta value. In some embodiments, the reporting circuitry 2756 of the microcontroller 2750 is configured to transmit a signal to at least one of a haptic reporting device, an audio reporting device, a wirelessly coupled reporting device, or an optical reporting device. In an aspect, the reporting device is attached to a garment, e.g., a nursing bra. For example, the reporting circuitry can be configured to transmit a signal to a vibrating haptic device associate with the nursing bra to provide a haptic alert regarding the calculated breast volume delta value. For example, the reporting circuitry can be configured to transmit a signal to one or more indicator lights associated with the nursing bra to provide an optical alert regarding the calculated breast volume delta value. For example, the reporting circuitry can be configured to transmit a signal to a speaker associate with the nursing bra to provide an audio alert regarding the calculated breast volume delta value.

In some embodiments, the reporting circuitry 2756 of the microcontroller 2750 is configured to transmit a signal to a transmission unit including an antenna. In an aspect, the transmission unit is operable to transmit a signal to at least one of a dedicated hand-held device, a mobile communication device, and/or a laptop or tablet computing device. In an aspect, the transmission unit is operable to transmit a signal to a network, e.g., a healthcare provider network or a social media network.

In an aspect, the microcontroller further includes compilation circuitry configured to compile the calculated breast volume delta values over time and transmit a signal including information regarding the compilation to the reporting device. In an aspect, the compilation circuitry compiles the calculated breast volume delta values over the course of a single breastfeeding event. In an aspect, the compilation circuitry is configured to generate a graphic representation of cumulative breast volume delta values over the course of a single breastfeeding event. In an aspect, the compilation circuitry is configured to generate a graphic representation of total breast volume delta values at each of one or more breastfeeding events. The graphic representation can be reported via a display associated with a dedicated hand-held device, a mobile communication device, and/or a laptop or tablet computer.

Figure 28:
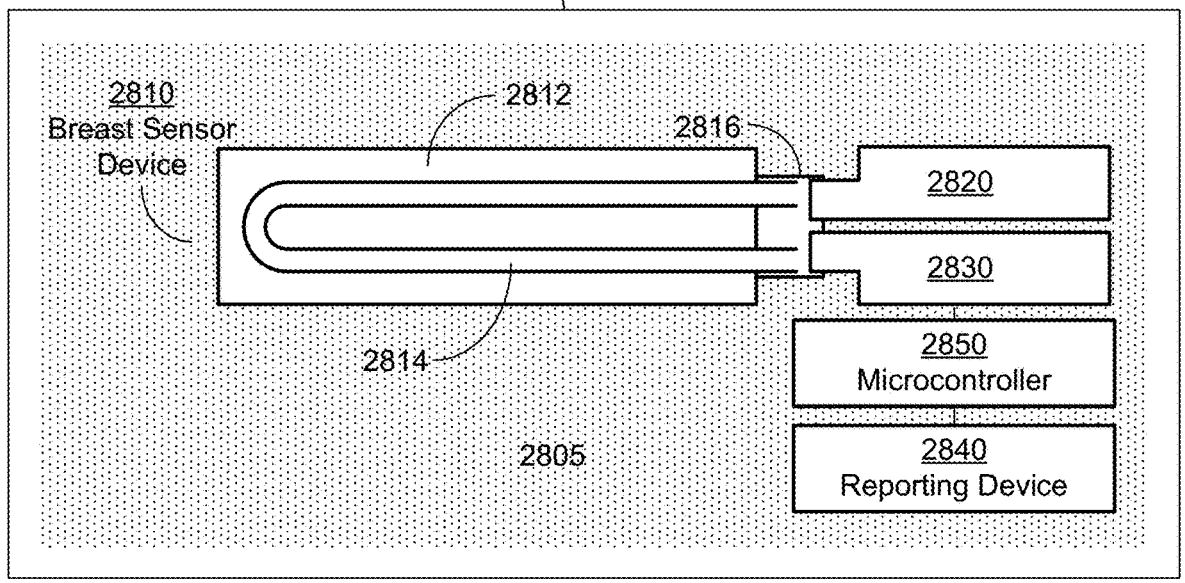
FIG. 28 illustrates an embodiment of a breast monitoring system including a breast sensor device.

In an aspect, a breast monitoring system such as described in FIG. 28 further includes a garment, wherein the garment includes a surface configured to accept the breast sensor device, and wherein the at least one light source, the at least one photodetector, the reporting device, and the microcontroller are associated with the garment. Breast monitoring system 2800 includes a breast sensor device 2810 including a flexible substrate 2812 associated with a surface 2805 of a garment, e.g., a nursing bra. For example, the breast sensor device 2810 can include an adhesive (e.g., a pressure sensitive adhesive) for adhering the sensor to the surface 2805 of the garment. For example, the breast sensor device 2810 can include a fastener of some sort (e.g., VELCRO or snaps) for attaching the sensor to the surface 2805 of the garment. The breast sensor device 2810 further includes one or more optical fibers 2814 associated with the flexible substrate 2812. In this non-limiting example, the one or more optical fibers 2814 are curved into a loop with each end associated with connector 2816.

Breast monitoring system 2800 further includes at least one light source 2820, at least one photodetector 2830, microcontroller 2850, and reporting device 2840. In this non-limiting example, the at least one light source 2820, the at least one photodetector 2830, the microcontroller 2850, and the reporting device 2840 are all associated with the surface 2805 of the garment. The at least one light source 2820 (e.g., a light emitting diode) and the at least one photodetector 2830 (e.g., a photodiode) are shown operably connected to the breast sensor device 2810 through the connector 2816. For example, the connector of the breast sensor device can be configured to "plug in" to the light source and photodetector. The microcontroller 2850 includes a microprocessor and circuitry including input circuitry, calculation circuitry, and reporting circuitry for receiving, processing, and reporting information associated with a breastfeeding event. The reporting device 2840 reports information regarding the breastfeeding event to a user and includes at least one of an optical, audio, or haptic reporting device, or a transmission unit.

In some embodiments, one or more of the light sources, photodetectors, microprocessor and reporting device are grouped together. For example, the light source and the photodetectors may be grouped together for ease in connecting with the connector of the breast sensor device. In some embodiments, all or part of the light sources, photodetectors, microprocessor and reporting device are resistant to an environment associated with cleaning a garment, e.g., a nursing bra. For example, all or part of the components are water resistant or are encased in a water resistant compartment. In some embodiments, the light sources, photodetectors, microprocessor and reporting device are combined in a single unit. A single unit including these components can be configured for easy attachment and removal from the garment so as to be able to clean the garment.

Figure 29:
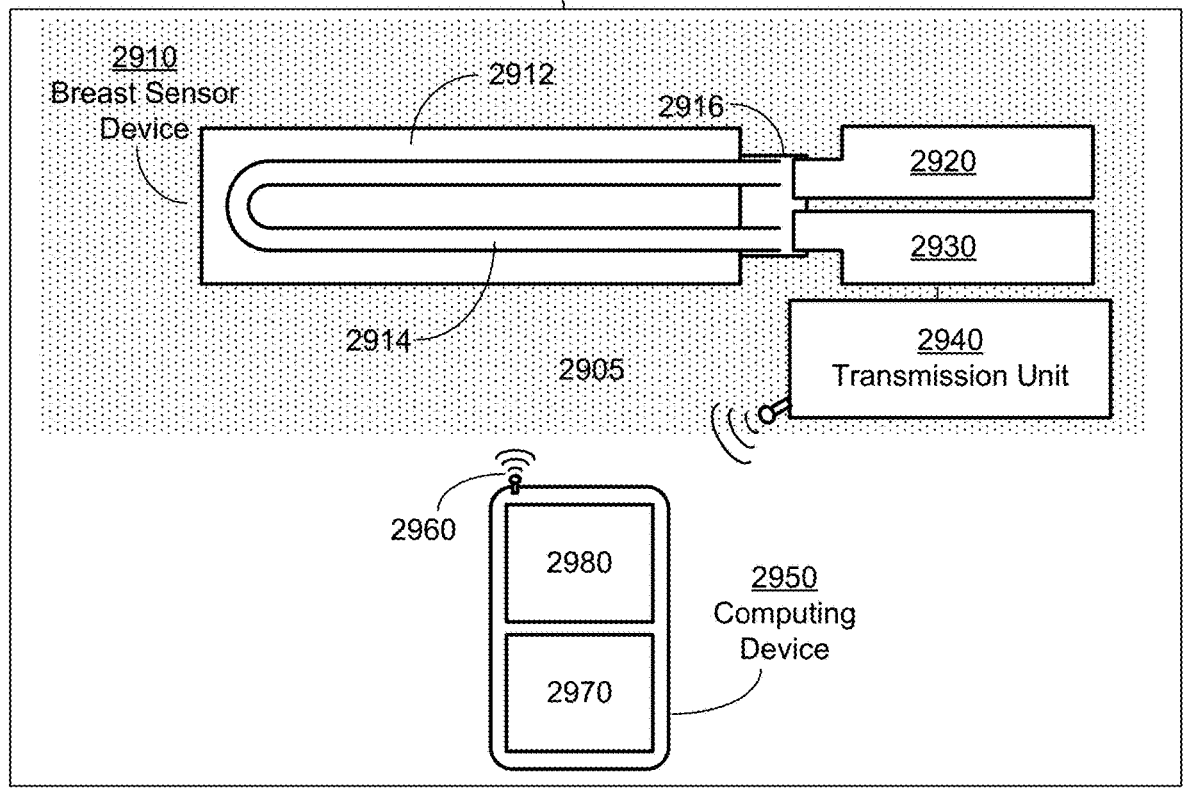
FIG. 29 illustrates an embodiment of a breast monitoring system including a breast sensor device.

In some embodiments, the microprocessor and/or the reporting device components of the breast monitoring system are not associated with the breastfeeding garment. For example, the microprocessor and/or the reporting device can be part of a separate computing device, e.g., a dedicated hand-held device, a mobile communication device, or a laptop or tablet computing device in communication with the other components of the system. FIG. 29 illustrates an example of a breast monitoring system including a computing device. Breast monitoring system 2900 includes breast sensor device 2910 associated with a surface 2905 of a garment, e.g., a nursing bra. Breast sensor device 2910 includes one or more optical fibers 2914 associated with (e.g., attached to) flexible substrate 2912. Breast sensor device 2910 is operably coupled (e.g., "plugged in") to at least one light source 2920 and at least one photodetector 2930 through connector 2916. The at least one light source 2920 and the at least one photodetector 2930 are associated with the surface 2905 of the garment. Breast monitoring system 2900 further includes a transmission unit 2940 operably coupled to at least the photodetector 2930. Transmission unit 2940 is configured to communicate with computing device 2950. Computing device 2950 includes an antenna 2960 configured to communicate with transmission unit 2940. Computing device 2950 further includes microprocessor 2970 including input circuitry, calculation circuitry, and reporting circuitry configured to receive, process, and report information associated with a breastfeeding event. The input circuitry, calculation circuitry, and reporting circuitry can be part of an application implemented on the mobile communication device. Computing device 2950 further includes reporting device 2980. In this non-limiting embodiment, the reporting device 2980 can include a user interface (e.g., a display and a keyboard or touchpad) for inputting and receiving information.

In some embodiments, a breast monitoring system includes a breast sensor device including a flexible substrate, one or more optical fibers associated with the flexible substrate, and at least one connector; at least one light source, at least one photodetector, and a transmission unit associated with a garment, e.g., a nursing bra; and a mobile communication device, in communication with the at least one photodetector through the transmission unit, the computing device including input circuitry, calculation circuitry, and reporting circuitry, wherein the reporting circuitry is configured to report the calculated breast volume delta value to a user through a display associated with the mobile communication device.

FIG. 30 illustrates a non-limiting embodiment of a breast monitoring system including a subset of the system components associated with a brassiere (e.g., a nursing bra) and configured for communication with a mobile communication device (e.g., a smart phone). Breast monitoring system 3000 includes brassiere 3005 including straps and cups. The brassiere can be configured for wear by a user during a breastfeeding event. Breast monitoring system 3000 includes breast sensor device 3010 including a flexible substrate associated with a surface of brassiere 3005. Breast sensor device 3010 includes one or more optical fibers 3012 associated with the flexible substrate and nipple access portion 3014. In this non-limiting example, the optical fibers form concentric circles around the nipple access portion 3014. Breast sensor device 3010 further includes connector 3016. Brassiere 3005 further has associated with it at least one light source 3020, at least one photodetector 3030, and a transmission unit 3040 including an antenna 3045. In this non-limiting example, these components are shown grouped together. In an alternative embodiment, each component may be separately associated with the brassiere.

Breast monitoring system 3000 further includes a mobile communication device 3050 including a transmission unit 3060 including a receiver and a user interface 3070. Mobile communication device 3050 can include a smart phone or cell phone or other mobile communication device. In some embodiments, the mobile communication device 3050 can include a tablet computer. The transmission unit 3060 includes a receiver configured to wirelessly receive signals from the transmission unit 3040 associated with the nursing bra 3005. Transmission unit 3060 can further include a transmitter configured to transmit signals to the transmission unit 3040 of the nursing bra 3005. In some embodiments, the transmission unit 3060 of the mobile communication device 3050 transmits signals carrying information for controlling one or more of the at least one light source 3020, the at least one photodetector 3030, or the transmission unit 3040 associated with the nursing bra 3005.

In some embodiments, a wearable breast monitor including one or more optical fibers can be used to measure a physiological parameter of a user. In an aspect, a wearable breast monitor comprises a flexible substrate fabricated to substantially conform to external contours of at least a portion of one or more breasts of a subject; one or more optical fibers associated with the flexible substrate, wherein the one or more optical fibers are dynamically bendable; at least one light source operably coupled to the one or more optical fibers; at least one photodetector positioned to detect light reception from the one or more optical fibers; a reporting device; and a microcontroller including a microprocessor and circuitry, wherein the circuitry includes input circuitry configured to receive a first set of signals from the at least one photodetector; and receive at least one second set of signals from the at least one photodetector; calculation circuitry configured to calculate a curvature delta value based on a comparison of the received first set of signals and the received at least one second set of signals from the at least one photodetector; and calculate a physiological parameter value from the calculated curvature delta value; and reporting circuitry configured to transmit a signal to the reporting device based on the calculated physiological parameter value.

In some embodiments, the physiological parameter value includes a step count. For example, the optical fibers associated with the wearable breast monitor can detect changes in breast curvature associated with a breast moving, e.g., bouncing up and down, with each step or footfall.

In some embodiments, the physiological parameter value includes a respiration rate. For example, the optical fibers associated with the wearable breast monitor can detect changes in breast curvature associated with movement of the chest and associated breasts during inhalation and exhalation.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

Prophetic Example 1: A Wearable Adhesive Strip Breastfeeding Monitor

A wearable breastfeeding monitor is fabricated to adhere to the breast and monitor the volume of milk in the breast before and after breastfeeding. A flexible strip of plastic is fabricated with flexible optical fibers, a light source and a photodetector which detects light transmitted through the optical fibers. The amount of light transmitted depends on the bend (or curvature) of the optical fibers. A microcontroller which includes a microprocessor and dedicated microcircuitry processes the light transmission data, calculates the volume of milk expressed during breastfeeding and reports to the mother via a haptic device.

The breastfeeding monitor is fabricated starting with a strip of poly(ethylene terephthalate)(PET) or polyester. Flexible polyester films and biomedical adhesives are available from Tekra, Division of EIS, Inc., New Berlin, Wis. For example, an adhesive-coated polyethylene tape that adheres well to the skin, and is conformable and hypoallergenic is suitable for fabricating the breastfeeding monitor as a strip which adheres and conforms to the external shape of the breast (see, e.g., FIGS. 5A and 5B).

Multimode silica optical fibers are attached to the strip in a linear arrangement spanning the adhesive strip (see, e.g., FIG. 3, 320). Standard glass-clad, silica core multimode fibers with a wavelength range of 400-2400 nm are available from ThorLabs Inc., Newton, N.J., and they may be attached to the polyethylene strip with epoxy that allows bending of the fibers/strip to conform with the shape of the breast. A white LED light source is connected to one end of the optical fibers (see, e.g., FIG. 3, 130). For example, a 0.3 W white LED with transmitter circuitry and optic connectors are available from Digi-Key Corporation, Thief River Falls, Minn. 56701 USA. A fiber optic receiver, photodetector (see e.g., FIG. 3, 140) is connected to the opposite end of the optical fibers. For example, a fiber optic receiver that includes a photodiode and output circuitry compatible with CMOS logic is available from Digi-Key Corporation, Thief River Falls, Minn. 56701 USA. The receiver detects light transmitted through the optical fibers and signals to a microcontroller (see FIG. 3, 160) which determines light intensities, calculates breast shapes and determines breast milk volumes.

A first pulse of light is transmitted prior to breastfeeding, and a second pulse of light is transmitted after breastfeeding. A differential in the amount of light received following the first and second pulses (i.e., delta in light intensity) results from bending in the optical fibers that accompanies the change of shape in the breast when milk is expressed. For example, a fiber optic system detects bending of optical fibers that results in attenuation of light transmitted through the optical fibers (see e.g., Fujiwara et al., *IEEE Sensors Journal* 14: 3631-3636, 2014 which is incorporated herein by reference). The delta in light detected by the fiber optic receiver before and after breastfeeding is signaled to the microcontroller where calculation circuitry calculates a delta in breast volume which corresponds to the amount of breast milk expressed during breastfeeding.

The wearable breast monitor includes a reporting device (see e.g., FIG. 3, 150) to alert the mother when a sufficient volume of milk has been consumed by her infant. For example, a haptic reporting device can include a vibrational motor (e.g., a coin or pancake vibration motor is available from Precision Microdrives Ltd, London, UK) that is used to alert the nursing mother when sufficient breast milk has been expressed. The haptic reporting device may be attached to the adhesive strip and signal by vibration on the breast when a sufficient volume of milk has been expressed. For example, when a predetermined minimum and/or maximum volume of milk has been expressed the mother may be alerted. The reporting device may include circuitry to signal wirelessly to the mother's cell phone and leave a record of the day, time and volume of milk expressed and consumed.

Prophetic Example 2: A Breastfeeding Monitor Nursing Bra

A breastfeeding monitor is incorporated in a nursing bra to detect and report the expression of breast milk during breast feeding. The nursing bra is constructed from a stretchable fabric that includes interwoven optical fibers in a spiral configuration in each cup. The bra cups fit snugly around each breast and conform to the breast shape. The optical fibers are inscribed with multiple Bragg gratings and connected to a light source and an optic receiver which detects light reflected through the optical fibers. A microcontroller, which includes a microprocessor and circuitry, processes light signals from the optical fibers and calculates changes in breast shape which are used to calculate breast milk consumption. A reporting device signals to the mother and an external device that a breastfeeding event has occurred and reports the volume of breast milk expressed.

The nursing bra is fabricated to incorporate all the elements of the breastfeeding monitor in a functional nursing bra. See, e.g., FIG. 11. The cups surrounding each breast are fabricated from a flexible fabric comprised of a thin woven polyester Spandex fabric with approximately 20% to 30% stretch in both width and length, so as to fit snugly and conform to the shape of the breast. Optical fibers are sewn in between the layers of polyester Spandex fabric in a spiral pattern (see FIG. 13, 1320) that is centered around the nipple access opening 1315. Single mode optical fibers with multiple Bragg gratings distributed over the fiber for multi-point distributed sensing are used to provide real time 3D sensing of the optical fiber. Optical fiber with Bragg gratings inscribed is available from Technica Optical Components, Atlanta, Ga. For example, see the Specification Sheet: T100/FBG Sensing Array which is incorporated herein by reference. Located between the bra cups on the bridge segment (see FIG. 11, 130), a laser diode source provides 980 nm light to the optical fibers on each breast. For example, a continuous wave laser diode which emits at 980 nm is available from Hamamatsu Photonics, San Jose, Calif. and a fiber Bragg grating (FBG) receiver 140 detects light reflected back through the optical fiber. FBG receivers are available from Redondo Optics, Redondo Beach, Calif. Changes in breast shape cause changes in shape (bends) of the optical fiber which in turn, cause changes in the light reflected from the Bragg gratings. Changes in reflected light detected by the receiver are processed by a centrally located microcontroller 160 which includes microprocessors and circuitry to process the photonic data and calculate changes in breast shape and breast volume. A reporting device 150 transmits breastfeeding data to an external device, (e.g., cell phone) and also alerts the mother directly with a haptic device or an audio signal. Expressed breast milk volumes determined periodically during breastfeeding are reported to a cell phone or laptop computer and when a preset minimum volume of milk is expressed the mother is alerted with a haptic or audio signal.

Prophetic Example 3: A Breastfeeding Monitor System for a Nursing Bra

A system to monitor breastfeeding is fabricated in a nursing bra with integrated optical fibers and connectors and a detachable module that includes a light emitting diode (LED) light source, a charge coupled device (CCD) photodetector, a microcontroller and a reporting device. The nursing bra cups are fabricated with polyester fabric which has interwoven optical fibers terminating in connectors that couple to the detachable module. The system detects change (delta) in breast shape to calculate change (delta) in breast volume following breastfeeding and reports the volume of milk expressed to the mother and to external devices, e.g., a cell phone or computer.

The system includes optical fibers associated with a flexible substrate of a nursing bra. Multimode silica optical fibers are interwoven with polyester fibers to create a flexible substrate including optical fibers that conforms to the external shape of the breast. Woven optical fiber substrates are described (see, e.g., U.S. Patent Appl. 2003/0044155 by Maiden, which is incorporated herein by reference). Polyester fabric with interwoven silica core multimode fibers is used to fabricate bra cups to hold the breasts and conform to their external shape. The optical fibers are interwoven in lateral patterns that span each breast cup. The ends of the interwoven optical fibers converge on connectors located in the bridge between the bra cups. Optical fiber couplers for coupling light into and out of optical fibers are available. See e.g., Achromatic FiberPorts that collimate over a range of wavelengths from ThorLabs Inc., Newton, N.J.

A detachable module for the breast monitoring system includes a LED light source, a CCD photodetector, a microcontroller and a reporting device which couples as a unit to the optical fiber connector on the nursing bra. A white LED light source is coupled to one end of the optical fibers. For example, a 0.3 W white LED with transmitter circuitry and optic connectors is available from Digi-Key Corporation, Thief River Falls, Minn. 56701 USA. A fiber optic receiver (i.e., photodetector) connects to the opposite end of the optical fibers. For example, a fiber optic receiver that includes a photodiode and output circuitry compatible with CMOS logic is available from Digi-Key Corporation, Thief River Falls, Minn. 56701 USA. The detachable module also includes a microcontroller with microprocessors and dedicated circuitry to process, and calculate data on changes in breast shape and breast volume. The microprocessor receives electronic signals from the photodetector corresponding to light transmitted through the optical fibers. For example, prior to breastfeeding, the white LED source transmits a constant light intensity through the optical fiber which is detected by the photodetector and processed by the microcontroller as light intensity at time zero. After breastfeeding, (e.g., for 10 minutes) the LED continues to transmits light through the optical fiber which is detected and processed as light intensity at time 10 minutes. However, bending of the optical fibers lowers the light intensity detected by the photodetector. For example, a fiber optic system that detects bending of optical fibers by measuring attenuation of light transmitted through optical fibers is described (see e.g., Fujiwara et al., *IEEE Sensors Journal* 14: 3631-3636, 2014, which is incorporated herein by reference). Circuitry in the microcontroller calculates a difference (i.e., delta) in light intensity which corresponds to a delta in the shape or bends of the optical fiber and a delta in the shape of the breast. Calculation circuitry converts changes in bending of the bra cup optical fibers to changes in shape of the breasts and finally to changes in volume of the breast. An exemplary volume calculation for a model breast with radius of curvature R (s) is shown in FIG. 17. Data on the volume of breast milk expressed is transmitted by the reporting device which may report to the mother with an audible or vibrating alarm when a minimum volume of breast milk has been expressed to nourish the infant. In addition, the reporting device may wirelessly transmit the volume of breast milk expressed, the time and the date to a mobile computing device, e.g., mobile phone to create a record of breastfeeding events for review by the mother and healthcare workers. The detachable module including the microcontroller, photodetector, LED and reporter may be disconnected at the coupler and removed in order to launder the nursing bra, or the module may be coupled with another nursing bra with different dimensions and different bra cups.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A breast monitoring system, comprising:
 a breast sensor device including
  a flexible substrate fabricated to substantially conform to external contours of at least a portion of one or more breasts of a subject;
  one or more optical fibers associated with the flexible substrate, wherein the one or more optical fibers are dynamically bendable; and
  at least one connector operably coupled to the one or more optical fibers;
 at least one light source configured to operably couple with a first end of the one or more optical fibers of the breast sensor device through the at least one connector;
 at least one photodetector configured to operably couple with a second end of the one or more optical fibers of the breast sensor device through the at least one connector, the at least one photodetector positioned to detect light transmission through at least one of the one or more optical fibers from the at least one light source;
 a reporting device; and
 a microcontroller including a microprocessor and circuitry, wherein the circuitry includes input circuitry configured to receive a first set of signals from the at least one photodetector, and receive at least one second set of signals from the at least one photodetector;

calculation circuitry including an algorithm configured to calculate a curvature delta value based on a comparison of the received first set of signals and the received at least one second set of signals from the at least one photodetector, and calculate a breast volume delta value from the calculated curvature delta value; and reporting circuitry configured to transmit a signal to the reporting device based on the calculated breast volume delta value.

2. The system of claim 1, further comprising a garment, wherein the garment includes a surface configured to accept the breast sensor device, and wherein the at least one light source, the at least one photodetector, the reporting device, and the microcontroller are associated with the garment.

3. The system of claim 1, wherein the at least one light source, the at least one photodetector, the reporting device, and the microcontroller are part of a detachable unit sized for attachment to a garment.

4. The system of claim 1, wherein each of the one or more optical fibers of the breast sensor device includes an inner core and an outer cladding, and wherein a portion of a core/cladding interface is modified to alter light transmission, wherein the amount of light transmitted out is dependent on the curvature of the one or more optical fibers.

5. The system of claim 1, wherein at least one of the one or more optical fibers of the breast sensor device includes one or more fiber Bragg gratings.

6. The system of claim 1, wherein the flexible substrate of the breast sensor device is a flexible strip or a flexible sleeve fabricated to substantially conform to the external contours of the at least a portion of the one or more breasts of the subject.

7. The system of claim 6, wherein the flexible strip or the flexible sleeve is sized for placement between the external contours of the at least a portion of the one or more breasts of the subject and a brassiere.

8. The system of claim 1, wherein the breast sensor device includes an adhesive on at least one surface of the flexible substrate.

9. The system of claim 1, wherein the breast sensor device includes at least one fastener configured to attach the breast sensor device to a garment, wherein the fastener is at least one of a snap, a button, a zipper, a hook and eye fastener, a hook and loop fastener, or a magnetic fastener.

10. The system of claim 1, wherein the breast sensor device includes a nipple access portion defined by the flexible substrate, wherein the nipple access portion includes an aperture in the flexible substrate sized to accommodate a nipple associated with the breast of the subject.

11. The system of claim 1, wherein the at least one connector of the breast sensor device is configured to operably connect the one or more optical fibers of the breast sensor device to at least one of the at least one light source and the at least one photodetector.

12. The system of claim 1, wherein the at least one connector of the breast sensor device includes at least one light input connector and at least one light output connector.

13. The system of claim 1, wherein the one or more optical fibers are attached to the flexible substrate of the breast sensor device.

14. The system of claim 1, wherein the one or more optical fibers are woven into the flexible substrate of the breast sensor device.

15. The system of claim 1, wherein the flexible substrate of the breast sensor device includes a first layer and a second layer, and wherein the one or more optical fibers are disposed between the first layer and the second layer of the flexible substrate.

16. The system of claim 1, wherein the one or more optical fibers are arranged in a pattern on the flexible substrate of the breast sensor device.

17. The system of claim 1, wherein the one or more optical fibers are arranged in at least one of a radial pattern, a spiral pattern, or concentric circles on the flexible substrate of the breast sensor device.

18. The system of claim 1, wherein the one or more optical fibers are arranged in overlapping patterns on the flexible substrate of the breast sensor device.

19. The system of claim 1, wherein the one or more optical fibers are arranged in a grid-like network on the flexible substrate of the breast sensor device.

20. The system of claim 1, wherein the at least one light source comprises at least one of a light emitting diode or a laser diode.

21. The system of claim 1, wherein the at least one photodetector includes at least one photodiode.

22. The system of claim 1, wherein the at least one light source is configured to emit one or more pulses of light, and wherein the at least one photodetector is configured to measure a time delta between its reception of light and emission of light by the at least one light source; and
wherein the calculation circuitry is configured to calculate positional information related to the curvature based upon the time delta.

23. The system of claim 1, wherein the at least one photodetector detects light transmission, light reflection, or a combination thereof through at least one of the one or more optical fibers associated with the breast sensor device.

24. The system of claim 1, wherein at least one of the one or more optical fibers has a cladding component having a first optical absorption coefficient and a core component having a second optical absorption coefficient, wherein at least one first photodetector is configured to detect light reception from the core component and at least one second photodetector is configured to detect light reception from the cladding component; and wherein the calculation circuitry is configured to calculate positional information related to the curvature based upon a difference between signals from the at least one first photodetector and signals from the at least one second photodetector.

25. The system of claim 1, wherein the reporting device comprises at least one of a haptic reporting device, an audio reporting device, or an optical reporting device.

26. The system of claim 1, wherein the reporting device comprises a transmission unit including an antenna, the transmission unit configured to transmit the information regarding the calculated breast volume delta value to an external device.

27. The system of claim 26, wherein the transmission unit is configured to transmit the information regarding the calculated breast volume delta value to at least one of a dedicated handheld device, a mobile communication device, a computing device, or a network.

28. The system of claim 1, wherein the calculation circuitry of the microcontroller is configured to calculate a volume of milk expressed during a breastfeeding event from the calculated breast volume delta value.

29. The system of claim 1, wherein the microcontroller further includes compilation circuitry configured to compile the calculated breast volume delta values over time and transmit a signal including information regarding the compilation to the reporting device.

30. A breast sensor device, comprising:
- a flexible substrate fabricated to substantially conform to external contours of at least a portion of one or more breasts of a subject;
- one or more optical fibers associated with the flexible substrate, wherein the one or more optical fibers are dynamically bendable; and
- at least one connector operably coupled to the one or more optical fibers, wherein the at least one connector is configured to operably connect the one or more optical fibers to at least one of a light source and a photodetector.

31. The device of claim 30, wherein each of the one or more optical fibers includes an inner core and an outer cladding, and wherein a portion of a core/cladding interface is modified to alter light transmission, wherein the amount of light transmitted out is dependent on the curvature of the one or more optical fibers.

32. The device of claim 30, wherein the at least one connector includes a light input connector configured to operably connect a first end of the one or more optical fibers to the light source and a light output connector configured to operably connect a second end of the one or more optical fibers to the photodetector.

33. The device of claim 30, wherein the flexible substrate is a flexible strip or flexible sleeve fabricated to substantially conform to the external contours of the at least a portion of the one or more breasts of the subject.

34. The device of claim 33, wherein the flexible strip or the flexible sleeve is sized for placement between the external contours of the at least a portion of the one or more breasts of the subject and a garment.

35. The device of claim 30, wherein at least one surface of the flexible substrate includes an adhesive.

36. The device of claim 30, wherein the flexible substrate includes a fastener configured to attach the flexible substrate to a garment, wherein the fastener is at least one of a snap, a button, a zipper, a hook and eye fastener, a hook and loop fastener, or a magnetic fastener.

37. The device of claim 30, further comprising a nipple access portion defined by the flexible substrate, wherein the nipple access portion includes an aperture in the flexible substrate sized to accommodate a nipple associated with the breast of the subject.

38. The device of claim 30, wherein the one or more optical fibers are woven into the flexible substrate.

39. The device of claim 30, wherein the flexible substrate includes a first layer and a second layer, and wherein the one or more optical fibers are disposed between the first layer and the second layer of the flexible substrate.

40. The device of claim 30, wherein the one or more optical fibers are one or more glass optical fibers.

41. The device of claim 30, wherein the one or more optical fibers are one or more plastic or polymer optical fibers.

42. The device of claim 30, wherein the one or more optical fibers are one or more photonic crystal fibers.

43. The device of claim 30, wherein the one or more optical fibers associated with the flexible substrate are arranged in a pattern.

44. The device of claim 30, wherein the one or more optical fibers associated with the flexible substrate are arranged in a radial pattern, a spiral pattern, concentric circles, or a grid-like network.

* * * * *